US008585751B2

(12) United States Patent
Drasler et al.

(10) Patent No.: US 8,585,751 B2
(45) Date of Patent: Nov. 19, 2013

(54) INTRAVASCULAR HINGE STENT

(76) Inventors: William Joseph Drasler, Minnetonka, MN (US); Joseph Michael Thielen, Buffalo, MN (US)

(*) Notice: Subject to any disclaimer, the term of this patent is extended or adjusted under 35 U.S.C. 154(b) by 0 days.

(21) Appl. No.: 13/199,796

(22) Filed: Sep. 10, 2011

(65) Prior Publication Data
US 2012/0065723 A1    Mar. 15, 2012

Related U.S. Application Data

(63) Continuation of application No. 10/236,846, filed on Sep. 6, 2002, now Pat. No. 8,016,873, which is a continuation of application No. 09/924,715, filed on Aug. 8, 2001, now Pat. No. 6,475,237, which is a continuation of application No. 09/780,145, filed on Feb. 9, 2001, now Pat. No. 6,312,460, which is a continuation of application No. 09/304,310, filed on May 3, 1999, now Pat. No. 6,245,101.

(51) Int. Cl.
*A61F 2/06* (2013.01)
(52) U.S. Cl.
USPC .......................................... 623/1.15; 623/1.16
(58) Field of Classification Search
USPC ............... 623/1.12, 1.15, 1.17, 1.1, 1.3, 1.32, 623/1.34
See application file for complete search history.

(56) References Cited

U.S. PATENT DOCUMENTS 6,241,762 B1 *    6/2001    Shanley ...................... 623/1.17

FOREIGN PATENT DOCUMENTS

WO    WO 9858600 A1 *    12/1998

* cited by examiner

*Primary Examiner* — Thomas J Sweet
*Assistant Examiner* — Christopher D Prone

(57) ABSTRACT

A balloon or self expandable endoprosthesis formed of a single or multiple joined stent sections. Each section has a node and strut structure extending throughout in order to uncouple expansion forces of the stent to hold a blood vessel outward from crush forces that resist the formation of an oval shape during crush deformation. The hinge can bend in the direction of a uniformly curved surface of the stent but not in the radial direction. The strut can bend in the radial direction but not in the uniformly curved surface of the stent. The widths, lengths, and radial dimensions of the hinges and struts provide a balloon-expandable hinge stent that is non-crushable. For a self-expanding stent the hinge and strut dimensions provide expansion forces that are controlled independently from crush forces. Expansion properties are determined by the hinge dimensions and crush properties are determined independently by strut dimensions.

8 Claims, 35 Drawing Sheets

INTRAVASCULAR HINGE STENT

This is a continuation of application Ser. No. 10/236,846 filed 6 Sep. 2002 and is now issued U.S. Pat. No. 8,016,873, which is a continuation of application Ser. No. 09/924,715 filed 8 Aug. 2001 and is now issued U.S. Pat. No. 6,475,237, which is a continuation of application Ser. No. 09/780,145 filed 9 Feb. 2001 and is now issued U.S. Pat. No. 6,312,460, which is a continuation of application Ser. No. 09/304,310 filed 3 May 1999 and is now issued U.S. Pat. No. 6,245,101.

BACKGROUND OF THE INVENTION

1. Field of Invention

The present invention relates to an expandable endoprosthesis that is placed within a tubular member of the human body to treat a region that is pathologically affected by supporting it or holding the tubular member outwards. More specifically the invention relates to an intravascular endoprosthesis placed within a blood vessel of the body generally at the site of a vessel lesion in order to provide a more widely open lumen and enhance patency of the vessel. The present invention further relates to a stent that can be used in blood vessels and tubular vessels of the body that have become stenotic or blocked by tissue or other material and require reestablishment of a lumen and maintenance of the lumen.

2. Description of Prior Art

Stents used to internally support tubular vessels of the body can generally be categorized into two groups, those that are mechanically expanded by an external device such as a balloon dilitation catheter, and those that are self-expandable. Advantages of the balloon expandable stents lies in part in the ability of these stents to be delivered accurately to the site of a stenotic lesion. The location of the stent prior to deployment or expansion can be visualized under flouroscopy and deployment of the stent is generally made by inflation of a dilitation balloon which expands the stent radially into contact with the inner surface of the vessel wall. After the dilitation balloon has been deflated and the dilitation catheter removed, the stent is left in place to balance radial forces applied by the vessel wall and ensure that the vessel lumen is maintained in a widely patent conformation.

Some difficulties associated with balloon expandable stents can be related to their lack of flexibility and their inability to withstand external forces that can lead to irreversible crushing of the stent. Several stents exhibit a structure that will not easily bend around tortuous pathways found in the human vasculature to reach the site of the lesion in their nondeployed state. Other stents have a structure that is made more flexible but are not appropriately capable of supporting or balancing the radial forces applied by the vessel acting to compress the stent. A stent with a low radial balancing force characteristics may be expected to undergo an irreversible crushing action if exposed to an externally applied force. Arteries of the neck and leg region can sometimes be exposed to such external forces resulting in permanent deformation of the stent and loss of vessel patency. This has been the case for some balloon expandable stents that have been placed in the carotid artery and exposed to digital or other external forces that have led to collapse of the stent.

In the balloon expandable stents currently found in the prior art one cannot adjust the amount of force required to expand the stent independently from the force required to crush the stent. As a result, a stent design that resists crushing action will generally be too stiff and require too much force to accomplish its deployment.

Self-expandable stents overcome some of the problems associated with the crushability of balloon expanded stents. These stents are typically made of Nitinol, a stainless steel with high yield strength, or some other material that can store energy elastically. Self-expandable stents can be delivered within a sheath to the site of the lesion. There the sheath can be removed and the stent can be deployed as it expands out to a larger diameter associated with its equilibrium diameter.

Some problems associated with self-expandable stents include the inability of the physician delivering the stent to define precisely the location of both ends of the stent. Oftentimes the stent can undergo significant changes in it axial length in going from an nondeployed state to a deployed state. Such length changes can result in inaccuracies in defining a precise placement for the stent. This disadvantage can be somewhat offset by the ability of some self-expandable stents to resist crushing deformation associated with an external force directed toward the side of the stent. Self-expandable stents also do not generally allow the radial expansion force to be adjusted independently from the stent forces that are directed to resist crushing forces. A self-expandable stent with an appropriate elastic balancing force to hold the vessel open may have a weak crush balancing force to resist crushing deformation due to externally applied crushing forces.

Palmaz discloses in U.S. Pat. No. 4,733,665 a balloon-expandable stent that is formed by machining slots into a metal tube forming a series of elongate members and bars. The stent is mounted in its nondeployed state onto the balloon portion of a balloon dilitation catheter and delivered to the site of a lesion that has been previously dilated to allow passage of the stent mounted balloon catheter. Dilation of the balloon causes the balloon-expandable stent to plastically deform at the junction of the elongate members and bars of the stent. For the stent to undergo an expansional deformation the balloon must supply an expansion applied force that exceeds the expansion yield force associated with the junction of the elongate members and the bars. Typically a balloon dilitation catheter used to dilate a coronary lesion found in a three millimeter diameter coronary artery can be dilated at a balloon pressure ranging from one to fifteen atmospheres. With the stent mounted on the balloon, the balloon must be capable of radially expanding the stent and holding the vessel in a widely patent conformation. Upon removal of the balloon catheter, the stent must continue to supply a compression balancing force to balance the compression applied force of the vessel acting inward on the stent. If an externally placed side force is imposed onto the side of the stent, the stent can deform into an oval or flattened shape representative of a crushing deformation. This deformation can involve an elongate member or it can occur at a junction of an elongate member with a bar. The elongate member can be formed such that it resists plastic deformation associated with crushing deformation. The junction of the elongate member with the bar cannot be adjusted to resist crushing deformation without also affecting the force required to expand the stent from its nondeployed state to its deployed state; additionally, the compression balancing force would also be affected. The Palmaz stent disclosed herein therefore can be susceptible to crush deformation in order to maintain appropriate characteristics for an expansion yield force during deployment and a compression yield force to hold the vessel in an open conformation.

A stent is required to have axial flexibility in order to negotiate the tortuous turns found in the coronary vasculature. Palmaz describes in U.S. Pat. No. 5,102,417 connector members that connect between small cylindrical stent segments. Although the connector members provide an enhanced axial flexibility, this stent is still subject to crush deformation. The compression yield force that is capable of holding the vessel outward with the stent in a deployed state is coupled to the crush yield force that prevents the stent from crush deformation.

Fischell describes in U.S. Pat. No. 5,695,516 a balloon-expandable stent formed from a metal tube and having circumferential arcs and diagonal struts. When this stent is expanded to a deployed state the junctions of the arcs and struts undergo plastic deformation and the deployed stent takes on a honeycomb shape. The expansion yield force of this stent describes the force required to plastically deform an arc with respect to a strut at a junction during stent expansion. The compression yield force describes the force required to plastically deform an arc with respect to a strut when exposed to a compression applied force by the blood vessel. Deformation due to crushing would also occur at the junction of the arc with the strut. The crush yield force of this stent is therefore directly coupled to the expansion yield force and the compression yield force. If this stent were designed to expand upon exposure to a dilitation balloon with a nominal expansion applied force, it would not be able to resist crushing deformation when exposed to an external side force that can be encountered in a carotid or femoral artery position.

Fischell describes in U.S. Pat. No. 5,679,971 a balloon-expandable stent that has two different types of cells, one for radial rigidity and one for axial flexibility. Neither one of these cells addresses the need to provide an anti-crush characteristic to the stent. One cannot adjust the crush yield strength of this stent independently of the expansion yield strength.

Lam (U.S. Pat. No. 5,649,952), Anderson (U.S. Pat. No. 5,800,526), Frantzen (U.S. Pat. No. 5,843,164), and Orth (U.S. Pat. No. 5,681,346) each describe balloon-expandable stents formed from metal cylinders and having serpentine wave patterns connected by interconnecting members. In each of these stent disclosures the stent has a crush yield force that is coupled to the expansion and compression yield force. These stents would be susceptible to irreversible crush deformation if exposed to an external force to the side of the stent.

Gianturco discloses in U.S. Pat. No. 4,800,882 a balloon-expandable stent constructed from a metal wire and discloses in U.S. Pat. No. 5,041,126 a method of insertion for a balloon-expandable stent. The wire stent disclosed by Gianturco has adjacent curved sections or loops joined by a bend or cusp. During stent expansion by a balloon the loops diverge as the metal wire irreversibly and plastically deforms. The deformation of the metal wire that occurs during expansion has a similar yield force as the deformation of the metal wire that can occur during compression of the stent if the compression applied force of the vessel exceeds the compression yield strength of the stent. If this stent is exposed to an external side force that could lead to a crush deformation, this stent can undergo plastic deformation that is irreversible and can occur with a similar yield force as the compression yield force. This stent is not well suited to provide independent adjustment of compression yield force with respect to crush yield force. As a result, this stent can be subject to crushing deformation even though the expansion and compression yield force are appropriate for allowing balloon expansion and support of the blood vessel.

Hillstead (U.S. Pat. No. 4,856,516), Wiktor (U.S. Pat. Nos. 5,133,732 and 4,886,062), Globerman (U.S. Pat. No. 5,776,161), Fontaine (U.S. Pat. No. 5,527,354), Horn (U.S. Pat. No. 5,591,230), Boyle (U.S. Pat. Nos. 5,613,981 and 5,591,198), and Hillstead (U.S. Pat. No. 5,116,365) each describe balloon-expandable wire stents made from loops, zig zags, helical wires, curved rings, sinusoidal waves, or other similar form of construction. All of the stents described in these disclosures are expandable by the expansion applied forces of a balloon of a balloon dilitation catheter or other similar catheter. During the expansion of the stents, the wires or each stent undergoes a plastic deformation once the expansion yield force has been exceeded. A plastic deformation would also be required for any of these stents to compress under the compression applied force applied by the vessel wall; this could occur once the compression yield force of the stent has been exceeded. Exposure of any of these stents to an external side force could lead to a crush deformation. It is not possible for any of these stents to enhance the crush yield force without altering the expansion or compression yield force of the stent.

Cox (U.S. Pat. No. 5,733,330) and Wall (U.S. Pat. No. 5,192,307) each describe balloon-expandable stents with ratchet mechanisms. The stents can be formed out of an elastic metal that will not allow for stent crushing and the ratchet mechanism can prevent the stents from collapsing under the force of compression applied by the blood vessel. Each one of these disclosures describes a separate latching or ratcheting mechanism that is required to provide the properties of balloon-expandable and non-crushability. The latching or ratcheting mechanism adds to the size and the complexity of the device.

Wallsten describes in U.S. Pat. Nos. 4,655,771 and 5,061,275 self-expandable stents formed from helically wound braided flexible thread elements or wires. The metal wires are elastic or resilient in nature with a high energy storage capacity. The stents can be delivered to the site of the lesion by an external sheath that applies a constraining force upon the stent to hold it in an nondeployed state of a smaller diameter. Upon release of the stent within the blood vessel, the stent undergoes a radial expansion to a larger predetermined diameter. The vessel provides a compression applied force due to vessel elasticity and collagenous scarring and contraction that can occur during vessel healing; this compression applied force acts inward on the stent. The stent in its deployed state provides an expansion elastic balancing force outward against the vessel wall to balance the compression applied force. If the stents described by these disclosures are acted upon by an external crush applied force delivered to the side of the stent, the stents can undergo an crush deformation forming an oval or flattened shape. The stents can provide a crush elastic balancing force to balance the crush applied force and limit the amount of crush deformation. The degree of crush deformation that can occur for a specific crush applied force is directly related to the size and number of flexible thread elements or wires used in the formation of the stents. The size and number of wires has a direct bearing on the expansion elastic balancing force provided by the stents. Therefore an increase in the crush balancing force will generally be associated with a corresponding increase in elastic balancing force. It can be desirable to adjust the crush balancing force independently of the elastic balancing force. The stents disclosed by Wallsten are not well suited to independent adjustment of the crush and the expansion elastic balancing force. Similarly, the crush balancing force is directly coupled to the expansion elastic balancing force.

Gianturco describes in U.S. Pat. Nos. 4,580,568 and 5,035,706 self-expandable stents formed from metal wire in a zig-zag pattern. These stents are elastically compressed to a smaller diameter for delivery within a blood vessel and undergo an elastic expansional deformation during delivery at the lesion site. The stents provide a deployed expansion elastic balancing force outward against the vessel wall to maintain the diameter of the vessel in an open and widely patent conformation. If exposed to an external crush applied force the stents will deform elastically and provide a crush elastic balancing force. The expansion and crush elastic balancing force are directly coupled and are not easily varied with respect to one another. Such stents with appropriate expansion characteristics are not easily adjusted to provide altered crush characteristics independently of one another.

Lauterjung (U.S. Pat. No. 5,630,829) and An (U.S. Pat. No. 5,545,211) describe self-expandable stents formed from metal wire. Lauterjung provides a high hoop strength stent due to the angle of the wire in the expanded state. An describes a zig-zag pattern that is spiraled into turns and is cross-linked with each other at adjacent turns. Each of these stents has an expansion and a crush elastic balancing force that is coupled directly to each other. One can not appropriately adjust the expansion characteristics with respect to the crush characteristics.

Carpenter describes in U.S. Pat. No. 5,643,314 made of a series of elastic metal bands or loops interconnected along a backbone. A lock is used to hold the loops in a contracted configuration around a balloon portion of a delivery catheter during delivery to the lesion site. Once expanded by the balloon, a lock is used to hold the loops outward in their expanded configuration. The strength of the lock provides the balancing force of the stent to hold the vessel in an open widely patent configuration. The dimensions of the metal loops determines the crush balancing force for a specific crush deformation. This stent is cumbersome to use with sliding required between metal and a locking mechanism that occupies areal space and volume.

McIntyre (U.S. Pat. No. 5,833,707) and McDonald (U.S. Pat. No. 5,728,150) each describe a stent formed from a flexible elastic metal sheet that has been coiled into a small diameter for delivery to a blood vessel. Upon release of the coiled stent, it springs out to form a larger deployed diameter and hold the vessel with an expansion elastic balancing force. The crush balancing force of these stents involves a similar defomation of the metal sheet as the expansion or compression deformation involved with the expansion delivery of the stents or collapse of the stents due to vessel compression applied forces. These stents do not provide for adjustment of the crush balancing force with respect to the expansion or compression balancing force.

Dotter (U.S. Pat. No. 4,503,569), Alfidi (U.S. Pat. No. 3,868,956), and Froix (U.S. Pat. No. 5,607,467) describe coiled stents constructed out of plastic or metal that can change in shape from a small diameter to a large diameter due to the application of heat, or application of another external condition. Most plastic stents are not acceptable due to the inadequate strength per volume of material in comparison to a metal stent. As a result, plastic stents require excessive areal space or volume which can be very undesirable in a small diameter blood vessel. Metal stents with a coiled shape have a similar mode of deformation in providing an expansion or compression balancing force in comparison to providing a crush balancing force. These stents do not allow the crush balancing force to be adjusted with respect to the expansion or compression balancing force.

Roubin discloses in U.S. Pat. No. 5,827,321 a stent that is radially expandable by balloon or self-expandable and designed to maintain its axial length upon expansion. The stent has annular elements connected by connecting members. The connecting members are formed from Nitinol and have a desire to lengthen upon deployment of the stent. The expansion or compression balancing force against the vessel wall is provided by the annular elements which have a curved or zig-zag structure. Upon exposure to a crush deformation it is the annular elements that provide the crush balancing force. The crush balancing force is coupled to the expansion or compression balancing force; the stent does not provide for independent adjustment of the balancing forces.

Williams (U.S. Pat. No. 5,827,322) describes a balloon-expandable or self-expandable stent formed from Nitinol flat metal sheet and having a ratchet mechanism to hold the stent in an expanded state. This stent is not flexible in the axial direction and the ratchet mechanism requires additional areal space and volume. This stent does not allow independent adjustment of crush balancing force without also significantly impacting the expansion elastic balancing force provided by the stent.

Hilaire describes in International Application with International Publication Number WO 98/58600 an expandable stent with variable thickness. The variable thickness is intended to allow the balloon expandable stent to expand more evenly along its perimeter. The stent is formed from a plurality of tubular elements with a zig zag shape that are joined together by linking members. This device does not teach or describe a stent that provides independent adjustment of stent expansion forces with respect to stent crush forces.

SUMMARY OF THE INVENTION

The present radially expandable intravascular stent overcomes the disadvantages described for other prior art balloon-expandable and self-expandable stents. The stent of the present invention has nodes that are attached to two or more struts. Each node has a hinge that focuses the deformation associated with expansion of the stent from its nondeployed or insertion state with a smaller diameter to its deployed or implanted state with a larger diameter. The radially expandable stent of this invention exerts forces against its environment and is exposed to applied forces from the environment. These forces will be described by the element generating the force, the direction of the force in either expansion or compression, and the type of force being exerted. For a balloon-expandable stent the hinge allows an inserted stent compression yield force and an implanted stent expansion yield force to be decoupled from an implanted stent crush elastic force thereby providing a stent that can be balloon expandable but noncrushable based on strut and hinge dimensions. This can be extremely valuable for applications such as carotid stenting where exact placement of a balloon-expandable stent is critical and the ability of the stent to resist crushing is a necessity. For a self-expandable stent, decoupling an implanted stent crush elastic force from an implanted stent expansion elastic force provides a stent that can be soft in crush deformation but provide adequate expansion elastic force to hold the vessel open. This type of stent may be advantageous in specific coronary artery stenting applications. Alternately, a self-expandable stent can be formed under the present disclosure that provides a large implanted stent crush elastic force but with a small or modest implanted stent expansion elastic force. This type of device may be useful in a situation where scar tissue may be contracting down on a vessel lumen. The stent of the present invention can be applied to any tubular vessel or passage found in the human body. Application of the hinge stent of the present invention can be made in particular to treatment of arterial blood vessels of the body. Such arterial blood vessels that can be treated with the present invention include small arteries such as coronary arteries and carotid arteries, middle size arteries such as femoral arteries and other vessels of the leg, and larger vessels including the aorta.

For a radially expandable balloon-expandable stent, a balloon expansion applied force is applied to the inside surface of the stent by a balloon of a balloon dilitation catheter or a similar catheter. Dilation of the balloon causes the stent to undergo a radial expansion that requires a plastic deformation such that the stent exceeds its elastic limit and exceeds the inserted stent compression yield force. A typical balloon dilitation pressure for a three millimeter diameter balloon is about 5-10 atmospheres. Balloon pressures can range from one atmosphere to dilate a very soft lesion to over 15 atmospheres to dilate a heavily calcified lesion. The stent will retain its expanded or deployed diameter and a tissue compression applied force applied by the blood vessel would have to exceed the implanted stent expansion yield force for the stent to collapse. The force exerted by the stent on the vessel wall is an implanted stent expansion holding force that must be large enough to hold the vessel at the deployed or implanted diameter of the stent and resist any diameter changes due to external forces or scarring. The inserted stent compression yield force cannot be so high that the balloon catheter is unable to expand the stent to the appropriate diameter. During this radial expansion of the stent the most significant plastic deformation occurs as an expansion deformation in an axial or circumferential direction within the uniformly curved surface of the stent, and relatively little crush deformation occurs with respect to the radius of curvature of the stent within a cross section. If a deployed stent is exposed to an external tissue crush applied force from one side it tends to form an oval shape representative of a crush deformation. If the tissue crush applied force exceeds the implanted stent crush yield force, the oval shape becomes extreme and can flatten as the stent can exceed its elastic limit in a crush deformation. During the crush deformation the wall of the stent is formed into an oval shape that is not the same as the expansion deformation encountered during the radial expansion.

The stent of the present invention allows a balloon-expandable and noncrushable stent to be formed from a metal that has a relatively high yield strength or high expansion yield force. The yield strength for the metal of the stent can be high enough such that when the stent is formed into an oval or flattened shape such as that found during crush deformation, the struts do not surpass their elastic limit and hence remain elastic. Each strut can be connected to two nodes through a hinge. The hinge is configured to provide plastic expansion deformation to the stent as it extends from a nondeployed insertion diameter to a deployed implantation diameter. The expansion deformation is focused in the hinge region such that localized plastic deformation occurs in the hinge. The hinge resists bending in the radial direction such as that deformation produced during a crush deformation. The result is a stent with appropriate inserted stent compression yield force that can be properly overcome by the balloon expansion applied force from the balloon dilitation catheter and strength to support the blood vessel and resist vessel contraction, and further provide the stent with non-crush characteristics.

A balloon-expandable stent of one embodiment of the present invention can be modified to provide modified stent expansion and compression yield force characteristics or modified implanted stent crush yield force characteristics independent of one another. This is accomplished by altering a radial dimension for the hinge and changing its width and length perpendicular to the radial dimension. For example, to increase the implanted stent crush yield force while maintaining the inserted stent compression yield force constant, the struts can be first enlarged in their sectional area to provide the desired crush yield force, or the material of the stent can be changed to attain a higher yield strength material. The struts can be formed of appropriate material and thickness to ensure that they remain elastic for any reasonable crush deformation encountered during normal use. The radial dimension of the hinge can be increased to provide an accompanying similar increase in crush yield force to the node. The width of the hinge in a direction perpendicular to the radial dimension and lying in the uniformly curved surface of the stent can be decreased such that the inserted stent compression yield force will remain constant. The hinge length can be decreased to further focus the expansion deformation in the hinge and ensure that plastic deformation will occur in consideration of the narrowing of the hinge width. If the hinge length is maintained in a longer configuration, the hinge can be configured to remain in an elastic state and not undergo a plastic deformation during expansion deformation; this node and hinge design of the present stent thus allows the formation of a self-expandable stent to also be accommodated.

A self-expandable stent generally has an equilibrium diameter wherein it is not applying any radial forces; this equilibrium diameter is somewhat larger than or approximately equal to the diameter of the vessel in which it is deployed or its implantation diameter. For a radially expandable self-expandable stent, the stent can be held and delivered to the blood vessel in a nondeployed state of smaller insertion diameter with a sheath compression applied force applied by some external holding means such as a sheath. The self-expandable stent exerts an inserted stent expansion elastic force upon the external holding means. Upon release from the holding means within a blood vessel, the self-expandable stent expands, and once fully deployed exerts an outwardly directed implanted stent expansion elastic force upon the walls of the blood vessel that is dependent upon the equilibrium diameter of the stent. If the implanted stent expansion elastic force is too large when the self-expandable stent comes into contact with the blood vessel, the blood vessel wall can begin to dilate and the stent can travel into the vessel wall causing trauma. If the implanted stent expansion elastic force is too low, vessel scarring and retraction of the vessel wall can apply a tissue compression applied force on the stent causing the stent to reduce in diameter to a value smaller than desired.

As the self-expandable stent undergoes an expansion from an nondeployed or insertion diameter to a deployed or implantation diameter an elastic expansion deformation occurs within the stent. This elastic expansion deformation occurs in the axial and circumferential direction of the stent wall and is not the same as the curvature change which occurs with respect to the radius of curvature of the stent in a radial direction during stent crushing. This elastic expansion deformation is very different from the deformation that would occur if the stent were exposed to a force along its side that would cause it to form an oval sectional shape associated with a crush deformation.

The stent of the present invention allows a self-expandable stent to be formed out of an elastic metal that will not plastically deform during normal use involving elastic expansion deformation or during exposure to a crush deformation. The struts could be formed with a sectional dimension that provides the self-expandable stent with an elastic crush deformation when exposed to an external tissue crush applied force to form an oval shape due to a crush deformation. The implanted stent crush elastic force of the stent can be high or low depending upon the desired properties of the stent. The struts are connected to one or more nodes through a hinge. The hinge has a greater radial dimension than the struts to resist the formation of an oval cross section associated with crush deformation. The hinge has a width that can be adjusted to provide an implanted stent expansion elastic force that is appropriate to resist the tissue compression applied force of the blood vessel. The hinge length can further be adjusted to alter the implanted stent expansion elastic force. The result is a self-expandable stent with appropriate expansion elastic force properties and a soft feel in a crush deformation. Similarly, the stent can have appropriate or nominal expansion elastic force properties and a very rigid, difficult to crush characteristic associated with a large implanted stent crush elastic force.

A self-expandable stent of the present invention can be modified to alter the inserted stent and the implanted stent expansion elastic force or implanted stent crush elastic force independent of one another. For example, to increase the crush elastic force while maintaining the inserted or implanted expansion elastic force, the struts can be enlarged in sectional area to provide the desired crush elastic force. The radial dimension of the hinge can be increased to provide an accompanying similar increase in crush elastic force in the node region. The width of the hinge in the uniformly curved surface of the stent can be decreased such that the expansion elastic force will remain constant. The hinge length can be decreased to provide a more focused bending of the hinge through a smaller radius of curvature to generate the appropriate expansion elastic force.

In an embodiment of the present invention a metal tube constructed of stainless steel, Nitinol, titanium, tantalum, or other metal used in constructing stents is machined using laser machining, mechanical machining, chemical etching or other machining process to form raised areas in the outside surface of the metal tube. These raised areas have a greater radial dimension than the rest of the tube and will later be formed into the hinges of the stent. It is important to note that the raised areas can be formed such that their radial dimension is as thin as any normal or standard balloon-expandable or self-expandable stent. The strut region can be formed such that the radial dimension is thinner than the strut region of a standard stent. The design of the present invention allows a material of greater elastic modulus to be chosen for stent formation thereby providing appropriate expansion force characteristics based on the design of nodes and struts utilizing a thinner strut dimension than could be used with other prior art stents. Slots are then formed into the metal tube using laser, mechanical, or chemical machining methods. The slots can be any combination of straight slots or curved slots at any combination of parallel, perpendicular, or at an oblique angle with respect to the axis of the tube. The metal tube is thereby formed into a repeating array of struts and nodes with each node generally connected to at least two struts through a hinge. Each strut has a radial dimension, a width, and a length and it extends between two nodes. The nodes have a greater radial dimension than the struts. Each node can include a hub which has a radial dimension that is greater than the strut radial dimension. The hub is connected to or contiguous with at least two hinges which have a width that is narrower than the width of the struts. The node can be a single long hinge if it is connected to only two struts. Each hinge has a transition region which serves to join and provide a uniform transition between a hinge and a strut. Each transition region expandable is formed of the same metal as the hinge and the strut and is therefore contiguous with the hinge and the strut.

In one embodiment of a balloon-expandable stent the node is connected to four struts. As the slotted tubular stent is expanded from an nondeployed or insertion diameter to a deployed or implanted diameter an array of diamond shaped spacings is formed between the struts and the nodes. Upon exposure of the stent to expansion deformation, plastic deformation occurs in the hinges located between the struts and the hubs. The struts move with respect to the hub during expansion deformation of the stent such that the stent is capable of supporting a blood vessel in an expanded or deployed state. Exposure of this expanded stent to a side force tends to create a crush deformation. The entire stent and the struts are formed of a metal with a high yield strength and hence the struts will bend elastically when exposed to such a crush deformation. The node, including the hub, the hinge, and the transition region have a greater radial dimension and hence will not deform significantly under the crush deformation. Thus the stent undergoes plastic expansion deformation in a localized region of the hinge but remains elastic in all other areas to resist irreversible plastic crush deformation.

In another embodiment a self-expandable stent has each node connected to four struts and has an equilibrium diameter approximately equal to its deployed diameter. Diamond shaped spacings are found between the struts and the nodes in a deployed state. This stent can either be machined in the deployed diameter or it can be machined in the nondeployed diameter or in an intermediate diameter between the deployed diameter and the nondeployed diameter and work hardened to form an elastic self-expandable stent with an equilibrium diameter approximately equal to the deployed diameter. Prior to delivery the stent is collapsed down to a nondeployed diameter and delivered through a constraining sheath or other delivery system to the blood vessel. The nondeployed self-expandable stent exerts an inserted stent expansion elastic force outward against the sheath. Upon delivery to the blood vessel and removal of the constraining sheath the self-expandable stent attempts to assume its equilibrium diameter and hold the blood vessel in an expanded state with an implanted stent expansion elastic force. The inserted and implanted stent elastic force for a particular metal of construction is determined primarily by the length, width, and radial dimension of the hinge. Exposure of this stent to a crush deformation causes the struts to reversibly bend in the shape of the oval cross section. The strut has been designed to deform elastically when exposed to a crush deformation. The strut can either provide a large implanted stent crush elastic force when deformed to a particular degree of deformation or a small implanted stent crush elastic force dependent upon the width, length, and radial dimension of the strut. The magnitude of the implanted stent crush elastic force is independent of the expansion elastic force which is determined by the hinge width, length, and radial dimension. The self-expandable stent of this invention allows the implanted and inserted expansion elastic force to be altered independently from the implanted stent crush elastic force. The stent of the present invention can be formed of a single cylindrical stent segment or section or it can be formed of two or more stent sections joined together by a connecting means.

In further embodiments of the present invention, one or more cylindrical stent sections of either the self-expandable stent or the balloon-expandable stent formed with an array of nodes and struts can be connected together with one or more flexible connecting means. The connecting means can be a hinged interconnector formed of nodes and struts similar to those of the stent section structure or it can be a connecting element formed of a straight or curved connecting leg without nodes or hinges. Two or more stent sections can be connected together with hinged interconnectors or connecting elements to provide the stent with additional axial flexibility around a bend in a blood vessel. Axial flexibility is particularly important in allowing a stent to be deliverable to very tortuous vessels such as are often found in the heart. The connecting means can attach from a node of one cylindrical segment of stent to a node of another cylindrical segment. The hinged interconnctor or the connecting element will allow the stent wall that is on the inside radius of curvature through a tortuous or bent path to compress or contract as the connecting means is deformed to a shorter axial length. The hinge of the hinged interconnector can undergo a plastic deformation or an elastic deformation as the stent passes along a tortuous path. The struts of the hinged interconnector remain elastic during passage along a tortuous path. The connecting means located on the outside of the radius of curvature of a bend is able to extend to a larger length. The connecting means can be formed of the same material as the struts and nodes of the stent and can be machined into the stent structure in a manner similar to the forming of the slots. The radial dimension of the hinged interconnectors can be equal to or smaller than the radial dimension of the struts and can have an equal or smaller width than the struts. The hinged interconnectors and connecting elements are generally designed to remain elastic during the extensional deformation encountered as the stent extends and contracts while extending along a bend in a blood vessel. As the stent in its nondeployed state is bent around a tortuous path the hinged interconnectors and connecting elements provide the stent with a flexible characteristic. After the stent is deployed, the hinged interconnectors also provide the stent with an ability to conform with a tortuous vessel wall without trying to exert forces that could undesirably try to straighten the vessel.

In still another embodiment the stent is formed in an array of nodes and struts wherein each node is connected to three struts. The configuration of nodes and struts can be used for either a balloon-expandable stent or a self-expandable stent. The presence of hinges with a greater radial dimension and a smaller width that the struts provides this embodiment with the advantage of decoupling the inserted stent compression yield force and the implanted stent expansion yield force from the implanted stent crush yield force, and decoupling the implanted and inserted stent expansion elastic force from the implanted stent crush elastic force. In addition, axial flexibility can be provided directly from the array of nodes and struts without the need for connecting means.

In one more embodiment of the present invention the metal tube can be formed into a stent with an array of nodes and struts that have each node connected to two struts. The node can be a single hinge that connects two struts. The hinges and struts can be formed in any combination of straight or curved shape along with any combination of axial, circumferential, or oblique orientation for either the hinges or struts. This stent can be formed into a balloon-expandable stent or a self-expandable stent. In a balloon-expandable stent the hinge uncouples the inserted stent compression yield force and the implanted stent expansion yield force from the implanted stent crush yield force. The strut portion is constructed such that crush deformation will not result in plastic deformation; the strut will remain elastic. This allows the balloon-expandable stent to be balloon-expandable and noncrushable. In a self-expandable stent the hinge uncouples the inserted and implanted stent expansion elastic force from the implanted stent crush elastic force. The strut portion is similarly constructed such that crush deformation will not result in plastic deformation of the strut which will remain elastic. This allows the self-expandable stent to have independent design of inserted and implanted stent expansion elastic force with respect to implanted stent crush elastic force.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

The present invention is a hinge stent that is formed of a plurality of nodes and struts that are arranged to provide enhanced properties over stents identified in the prior art. A balloon-expandable hinge stent is balloon-expandable and noncrushable to provide the accurate placement associated with some balloon-expandable stents and not be susceptible to plastic crush deformation from externally applied forces. A self-expandable hinge stent can provide a large outward expansion elastic force and yet be soft in a crush deformation while remaining elastic in this crush deformation.

Figure 1A:
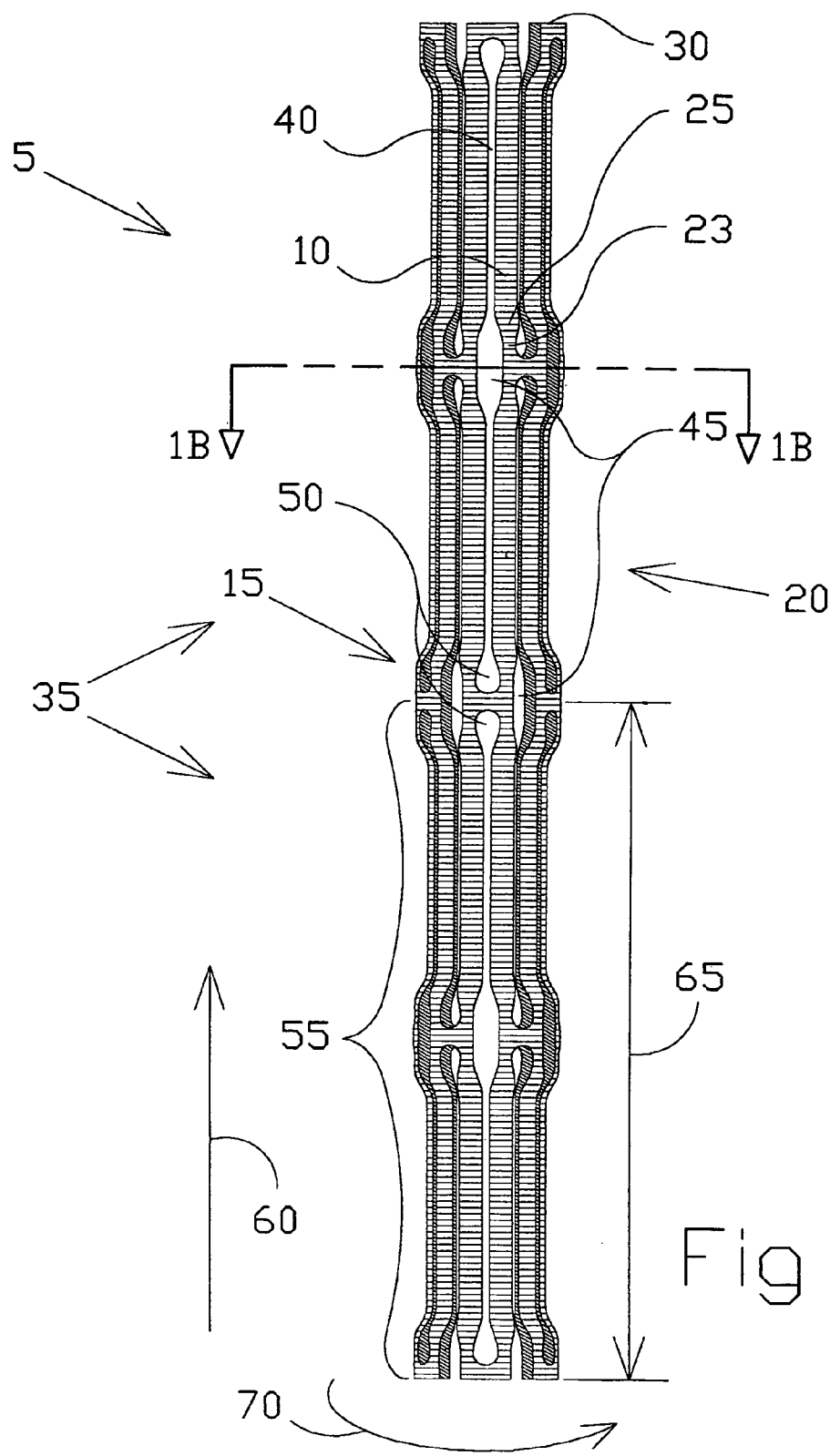
FIG. 1A is an isometric view of a hinge stent having a four strut per node stent body in a nondeployed state.
Figure 1B:
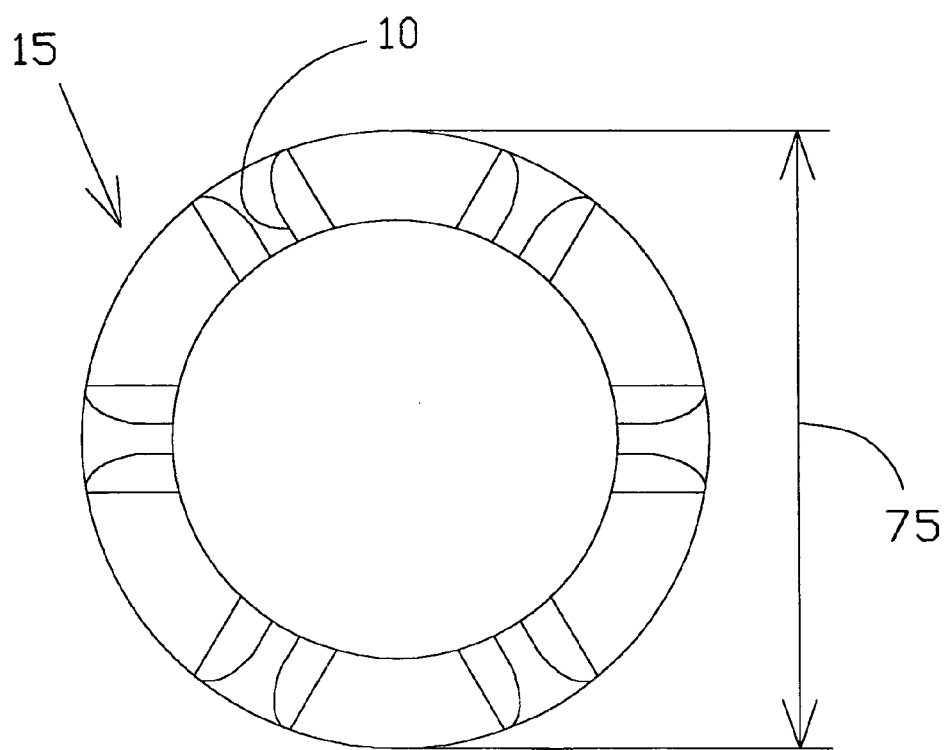
FIG. 1B is a sectional view of the hinge stent of FIG. 1A.

FIG. 1A shows one embodiment of a hinge stent 5 of the present invention in a nondeployed state or inserted state with struts 10 and nodes 15 joined together to form a stent section 20. A stent section 20 is made up entirely of nodes 15 and struts 10 extending throughout the stent section. Each node 15 of the hinge stent 5 includes at least one hinge 23 and at least two transition regions 25; each transition region 25 connects a node with a strut; and each strut extends between two nodes 15. At each stent end 30 of the hinge stent 5 the pattern of nodes 15 and struts 10 can differ from the general structure found throughout the stent section body 35. In this embodiment each node has four struts 10 joined contiguously to it throughout the hinge stent section body 35 and two struts 10 per node at each end of the hinge stent 5. The metal forming each of the struts 10 flows contiguously, from the same metal or material of construction, into the node to which it is joined without an attachment site. The hinge stent 5 has a generally cylindrical shape wherein the struts 10 are separated by interstrut openings 40 and nodes 15 are separated by internodal openings 45. Intranodal openings 50 are found within the nodes 15 and are connected to the interstrut openings 40. The hinge stent 5 of this embodiment is formed of a stent section 20 that extends with a single common pattern of nodes 15 and struts 10 throughout its length. The stent section 20 is made up of more than one repeat unit 55 of the same type or configuration that are joined contiguously together and are formed entirely of nodes and struts. A repeat unit is the smallest repeating portion of the stent structure which when combined with another repeat unit allows the stent section to extend in the axial direction 60 and consisting entirely of nodes and struts. A repeat unit repeats itself at least twice to form at least two repeat units along the length of a stent section. The stent section has a substantially continuous structure throughout its perimeter along the entire length of the stent section. This continuous structure provides the stent section with an outer surface that cannot form an abrupt transition in diameter that can cause a stress riser or stress concentration region to form in the vessel wall being treated. Such stress risers can lead to adverse healing of the treated vessel. The hinge stent 5 of this embodiment has a nondeployed repeat unit length 65 in the axial direction 60 that repeats more than one time to form the stent section 20. The repeat unit for this embodiment has a closed structure with four struts 10 joined to four nodes 15 forming an enclosed space. The closed structure or closed configuration provides structural integrity to the stent in an expanded or deployed state in both the axial and circumferential direction 70. The closed configuration of the present embodiment provides nodes and struts that extend in both the circumferential and the axial direction to form a continuous structure of nodes and struts extending continuously throughout the stent section. This continuous configuration of nodes and struts provides the hinge stent with a coupling or sharing of forces exerted in the axial direction with those exerted in the circumferential direction. The circumferential strength to hold the vessel outward is also supported throughout the entire stent section. A partial expansion of a portion of the stent section will result in at least a partial expansion of an axially adjacent portion of the stent section forming a smooth tapering of the stent section along its axial length rather than an abrupt change in stent diameter. FIG. 1B shows a sectional view with a noninserted diameter, a nonexpanded, or a nondeployed diameter 75 of the hinge stent 5.

Figure 2A:
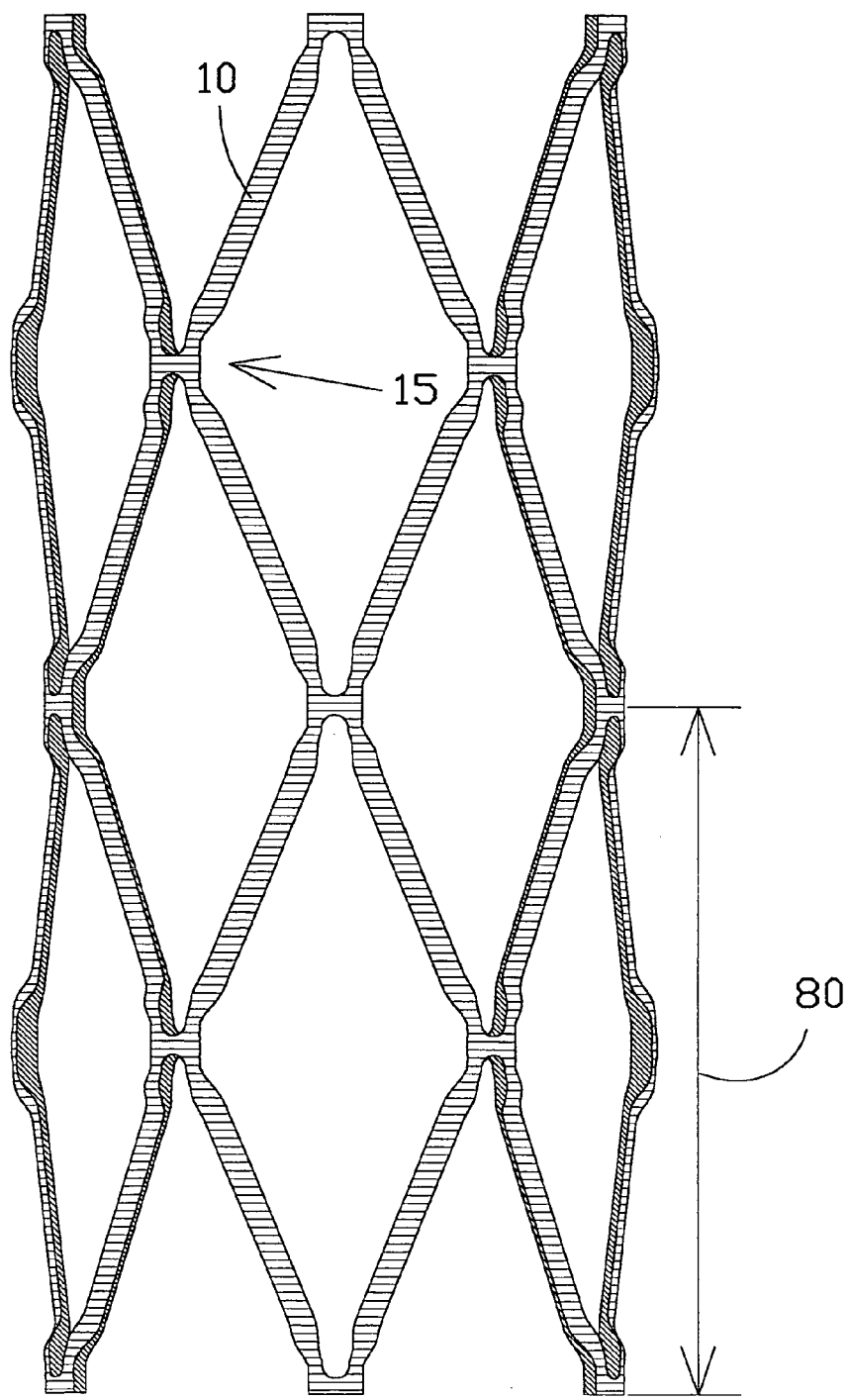
FIG. 2A is an isometric view of a hinge stent having a four strut per node stent body in a deployed state.
Figure 2B:
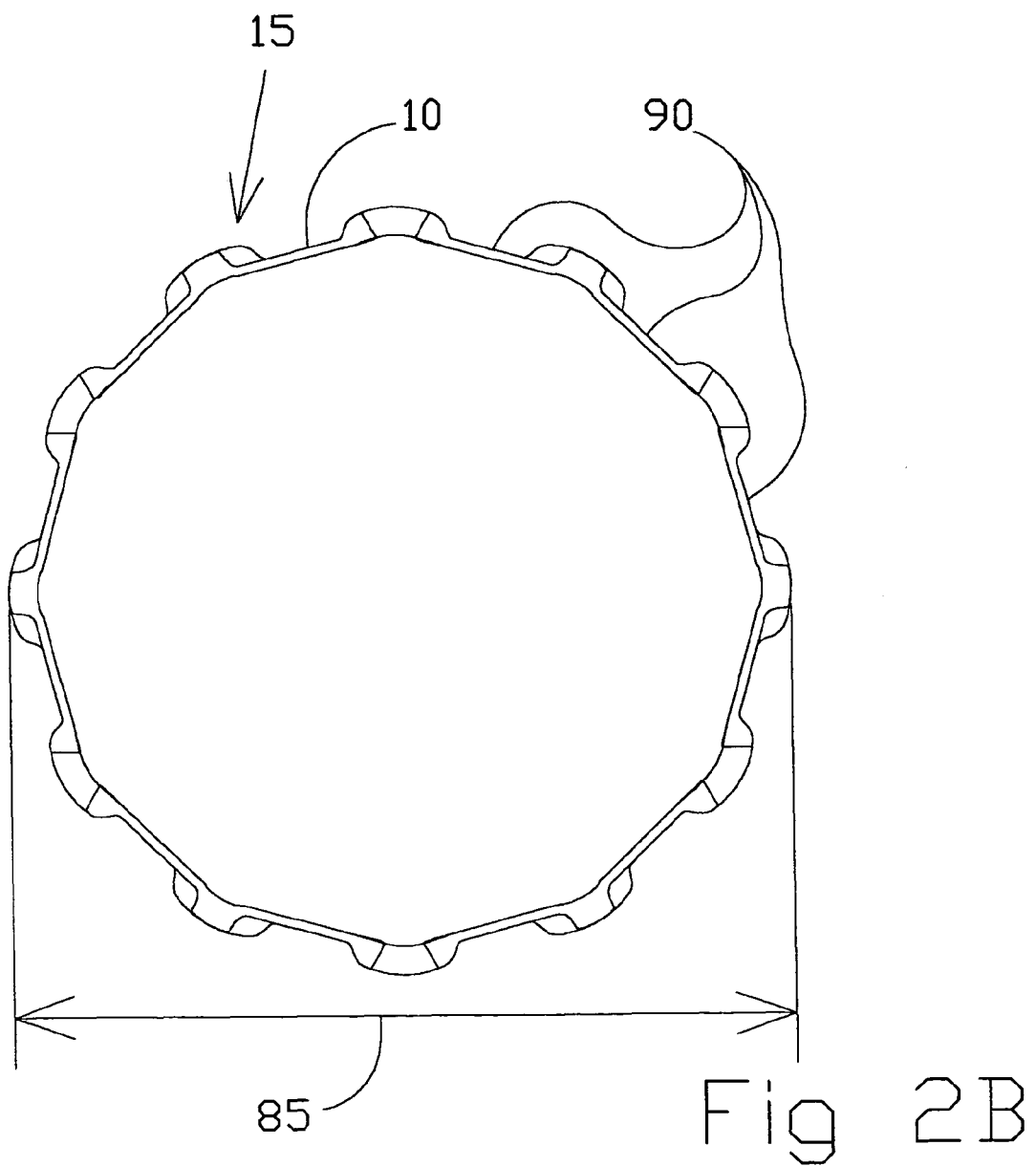
FIG. 2B is a sectional view of the hinge stent of FIG. 2A.

FIG. 2A is an isometric view of the hinge stent 5 in a deployed state showing a deployed repeat unit length 80. FIG. 2B is a sectional view of the hinge stent 5 shown in FIG. 2A showing the implanted diameter, expanded diameter, or deployed diameter 85. In the deployed state the hinge stent 5 has a generally cylindrical uniformly curved hinge stent surface 90. All reference numerals found in FIGS. 2A and 2B correspond to those elements previously or otherwise described.

The hinge stent 5 of the present invention is not required to have a uniform pattern of nodes 15 and struts 10 throughout its entire length as shown in this embodiment with a single stent section. The hinge stent 5 of the present invention can be formed of a stent section 20 that consists of a length of hinge stent 5 with more than one common pattern of nodes 15 and struts 10, and is made up entirely of nodes 15 and struts 10. The hinge stent 5 of the present invention can be formed of a single stent section 20 such as described in the embodiment of FIGS. 1A and 2A or the hinge stent 5 can be comprised of more than one stent section 20. A hinge stent 5 with more than one stent section 20 can be formed by joining one or more nodes 15 located at the end of one stent section 20 with one or more nodes 15 of another stent section 20 using one or more section connectors as described in more detail later. The section connectors can be themselves formed of nodes 15 and struts 10 or the section connectors can be a metal bar element. The nodes 15 on the end of one stent section 20 can be uniformly joined to the nodes 15 of another stent section 20 along their perimeters with section connectors formed of nodes 15 and struts 10. It is understood that a single stent section forms the preferred embodiment of the hinge stent of this embodiment. Section connectors can be used to allow individual stent sections to be brought together to form a longer hinge stent.

The hinge stent 5 of the present invention can be a balloon-expandable hinge stent 5 or a self-expandable hinge stent 5. As a balloon-expandable stent the hinge stent 5 can be mounted in its nondeployed state on a balloon of a balloon dilitation catheter for percutaneous delivery or insertion into the blood vessel that is to be treated. Upon reaching the site of vessel injury, the balloon of the balloon dilitation catheter can be expanded to apply a balloon expansion applied force onto the hinge stent 5. Once this applied force exceeds the inserted hinge stent compression yield force the hinge stent 5 will expand to the deployed diameter 85. In the deployed state the hinge stent 5 exerts an implanted stent expansion holding force outwards to balance the tissue compression applied force acting inward by the vessel wall. If the tissue compression applied force exceeds an implanted stent yield force, the stent will not be able to hold the native vessel outwards and it will reduce in diameter. The hinge stent 5 can be formed out of a metal that provides for plastic deformation of specific portions of the hinge stent 5 during the expansion from a nondeployed state to a deployed state. Such metals include titanium, tantalum, stainless steel, and other metals or alloys suitable for implant.

As a self-expandable stent the hinge stent 5 can be delivered or inserted into the vasculature with a delivery sheath that imparts a sheath compression applied force onto the hinge stent 5 which is being held elastically in a nondeployed state. The hinge stent 5 exerts an outward inserted stent expansion elastic force against the sheath. Once the hinge stent 5 is delivered to the site of the lesion, it can be removed from the sheath or other delivery means and allowed to expand outward and exert an implanted stent expansion elastic force against the vessel wall to hold the wall outwards with a force that balances the tissue compression applied force exerted by the vessel wall. The hinge stent 5 can be formed out of a metal that provides for elastic deformation including stainless steel, Nitinol, and other metals and metal alloys.

Figure 3:
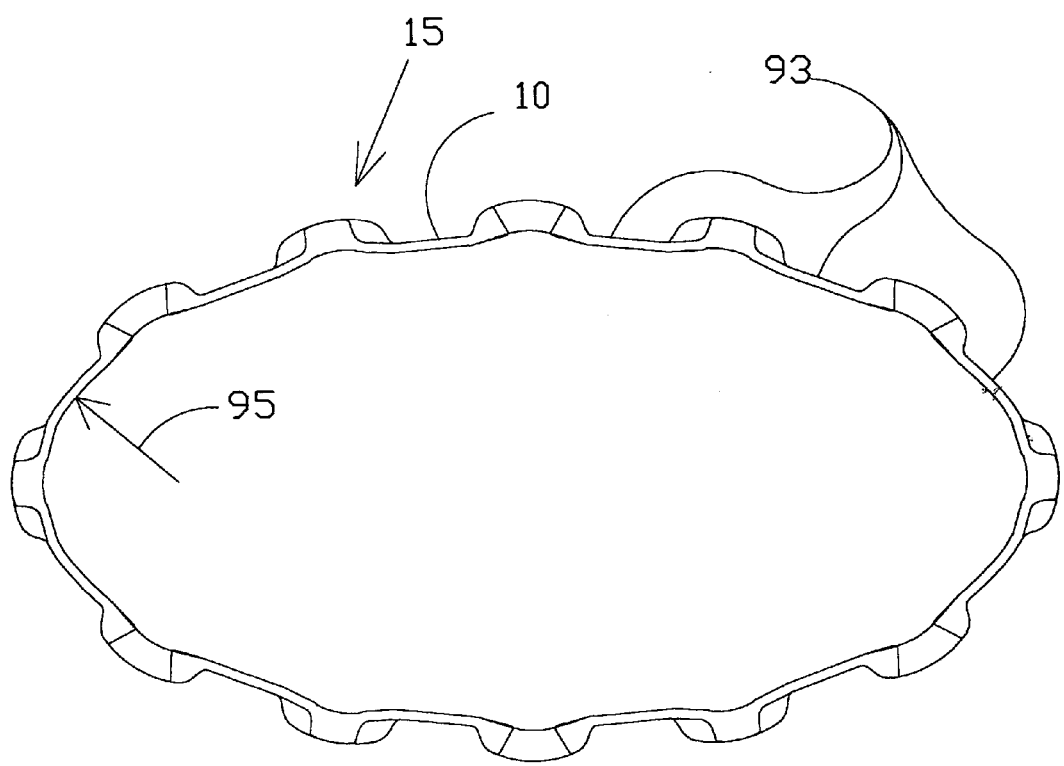
FIG. 3 is a sectional view of the hinge stent of FIG. 2A exposed to a crush deformation.

A balloon-expandable or self-expandable hinge stent 5 of the present invention in a deployed state will form an oval hinge stent surface 93 as shown in FIG. 3 when exposed to a tissue crush applied force. Such an applied force can occur when the hinge stent 5 is exposed to an externally placed side force or if patient or tissue movements can cause the hinge stent 5 to undergo a crush deformation or become oval. When the hinge stent 5 is exposed to a crush deformation, the struts 10 will bend elastically to a radial radius of curvature 95 that is smaller in the crushed portion of the stent perimeter. The hinge stent 5 exerts an outward implanted stent crush elastic force to resist the crush deformation. All reference numerals correspond to those elements previously or otherwise described.

Figure 4:
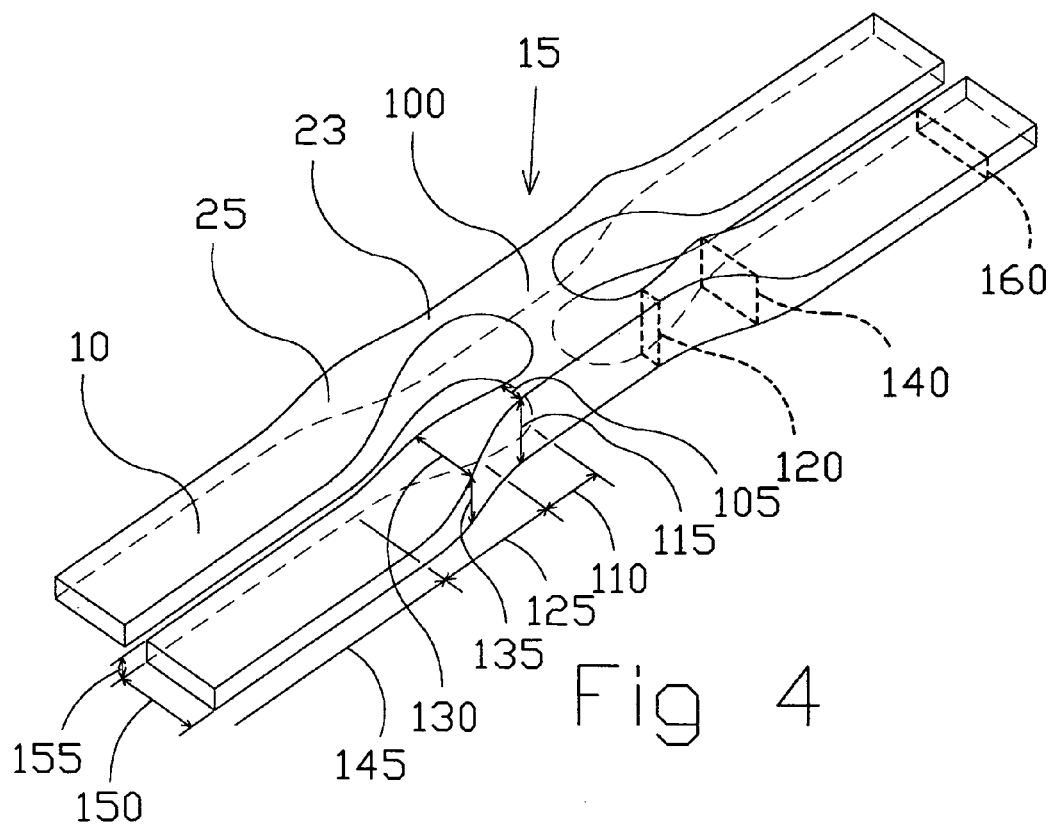
FIG. 4 is an enlarged detail view of a portion of the hinge stent shown in FIG. 1A.
Figure 5:
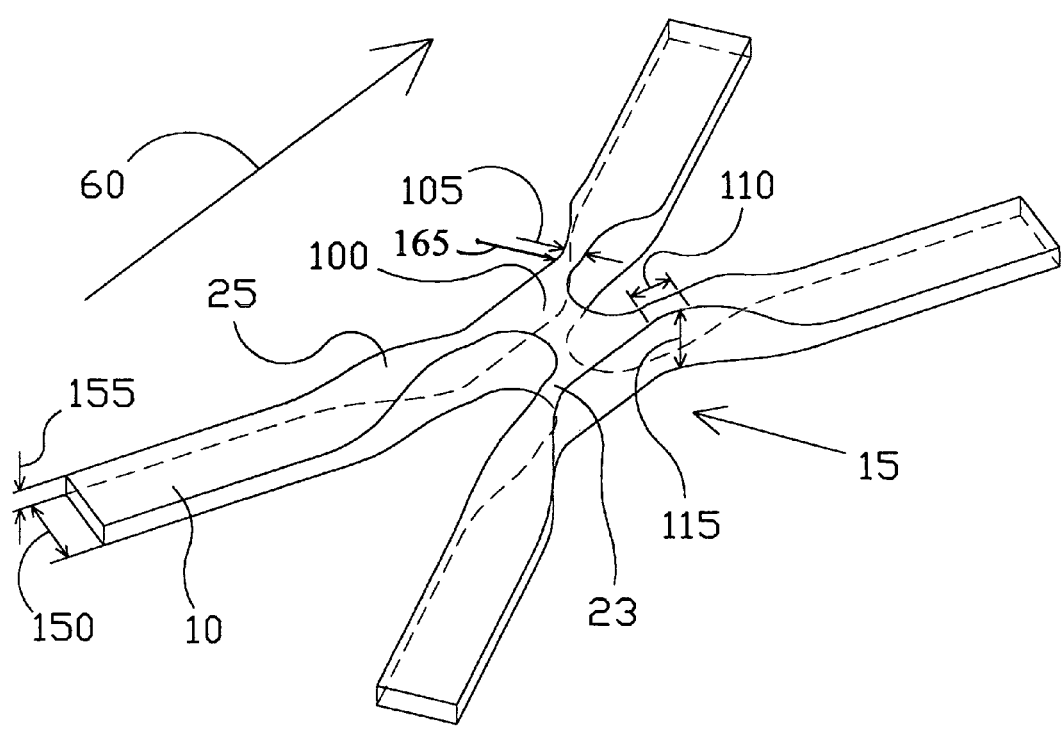
FIG. 5 is an enlarged detail view of a portion of the hinge stent shown in FIG. 2A.

FIG. 4 is an enlarged detail view of a portion of the hinge stent 5 shown in FIG. 1A in a nondeployed state and FIG. 5 is an enlarged detail view of a portion of the hinge stent 5 shown in FIG. 2A in a deployed state. In this embodiment four struts 10 are connected to a node which includes a hub 100, four hinges 23, and four transition regions 25. The hub 100 forms a region of the node that does not provide significant deformation during an expansion deformation from a nondeployed state to a deployed state or during a crush deformation as shown in FIG. 3. Each of the four hinges 23 is contiguously joined on one end to the hub 100. Each hinge has hinge dimensions which include a hinge width 105, a hinge length 110, a hinge radial dimension 115, and a hinge cross sectional area 120. The hinge is contiguously joined on another end to a transition region 25 which has a transition region length 125, transition region width 130, transition region radial dimension 135, and transition region cross sectional area 140. The transition region 25 is joined contiguously to a strut which has strut dimensions which include a strut length 145, a strut width 150, a strut radial dimension 155, and a strut cross sectional area 160. The hinge dimensions are such that they can provide the hinge stent 5 with a large outward expansion force yet not be subject to bending due to crush deformation. The strut dimensions are such that they provide the hinge stent 5 with a strong beam that can transfer the large outward expansion force of the hinge to the vessel wall to hold it open, yet allow elastic bending to occur due to crush deformation. The transition region 25 provides the appropriate transition between the hinge and the strut to allow the hinge and strut to perform their respective functions as described previously in the most efficient manner without allowing for bending of the transition region 25 due to crush deformation or bending of the transition region 25 due to expansion deformation from a nondeployed to a deployed state. The result is a hinge stent 5 that uncouples the expansion forces generated by the hinge from the bending characteristics generated by the strut in crush deformation. These characteristics will be further discussed in general terms and applied to the hinge stent 5 of the present invention.

The nodes and struts form a diamond shaped configuration to the hinge stent in a deployed state. This diamond shaped configuration is a closed configuration that ties the circumferential and axial movement within the stent section together. This closed structure forms a continuous configuration of struts and hinges that extends throughout the entire stent section. Forces exerted outward by the stent section are stabilized by the struts and hinges extending throughout the stent section.

The stress versus strain relationship for a metal beam such as a strut or a hinge can in general be estimated by Hooke's law which states that stress applied to the metal beam is equal to an elastic modulus times the strain or deformation to which the beam will deform. This elastic modulus or Young's modulus is a material property characteristic of the particular metal being used for the beam. The deformation can be a bending deformation that is characteristic of the expansion deformation encountered by the strut or the hinge, or it can be a bending deformation characteristic of a crush deformation. A beam in an unstressed state that is exposed to an applied stress below its elastic limit or yield stress will undergo an elastic flexure or elastic deformation which is reversible and the bar will return to its unstressed state upon removal of the applied stress. If the beam is exposed to an applied stress that is larger than its yield stress or if it is deformed to an inelastic flexure that is greater than its elastic limit or proportional limit, or if it is deformed beyond its yield point, plastic deformation will occur and the beam will not return to its original unstressed state with the original conformation or shape of the beam. The beam will generally return a fraction of the way back to its initial unstressed state due to the elastic portion of the deformation.

Exposing a beam to a torque or moment can result in bending the beam from a straight shape to a bent conformation with a radius of curvature. The relationship between the applied moment and the radius of curvature can be estimated by the equation that states that moment is equal to Young's modulus times moment of inertia divided by radius of curvature. The moment of inertia is different for different cross sectional shapes of the beam that is being bent. For a beam with a circular cross section and having a diameter, the moment of inertia is given by Pi time the diameter to the fourth power divided by 64. For a rectangular beam cross section with one side of magnitude B and another side of magnitude H, where B is the magnitude of the side in the radial direction of the radius of curvature and H is the magnitude of the side perpendicular to B, the moment of inertia is given by B to the third power times H divided by 12. Similarly, the beam can be bent from one radius of curvature to a second radius of curvature with a similar type of analysis as described above by examining the change in radius of curvature that is comparable to that of starting with a flat or straight shape and bending it to a curved shape.

A beam of a specific length and cross section that is exposed to a moment will undergo a bending deformation to a specific radius of curvature and one end of the beam will undergo a specific displacement with respect to other end. A beam of half the specific length but of the same cross section exposed to the same moment will undergo a bending deformation to the same radius of curvature but the displacement of one end with respect to the other end will be half of the original specific displacement. Although the localized deformation within each element of the beam is the same in both instances, the overall displacement of the longer beam was twice as great. Expanding upon this concept one finds that for a similar specific displacement of one end with respect to the other, a longer beam will have a smaller radius of curvature and each element of the beam will undergo a smaller localized deformation. Also expanding upon the concept one finds that a smaller moment is required to bend the larger beam to the same displacement of one end with respect to the other as the smaller beam. These concepts can be applied directly to the hinges 23 and struts 10 of the present invention. For example, a longer hinge can provide a greater displacement, corresponding to a greater deployment angle, without as much localized deformation of the hinge, than a shorter hinge. A shorter hinge that provides the same displacement, corresponding to the same deployment angle, will require a greater moment, than a longer hinge assuming that both the short and the long hinges 23 are behaving either elastically or plastically. A similar discussion can be applied to the strut length 145.

The hinge cross sectional area 120 is equal to the multiplication product of the hinge width 105 and the hinge radial dimension 115. Each hinge has a large hinge radial dimension 115 that does not allow for significant bending deformation along a radius of curvature with a radius aligned along the hinge radial dimension 115. The hinge radial dimension 115 is larger than the strut radial dimension 155. During an expansion deformation of the hinge stent 5, bending deformation for each hinge occurs to form a radius of curvature with the radius aligned along the hinge width 105, and this radius of curvature is referred to as the hinge width radius of curvature 165 (see FIG. 5). The moment of inertia for the hinge for expansion deformation can be estimated by using the hinge width 105 to correspond with the magnitude B and the hinge radial dimension 115 to correspond with the magnitude H. The strut cross sectional area 160 is equal to the multiplication product of the strut width 150 and the strut radial dimension 155. The moment of inertia for each of the struts 10 for bending due to crush deformation can be estimated using the strut radial dimension 155 to correspond with the magnitude B and the strut width 150 to correspond with the magnitude H. The radial dimension for the strut is small in comparison to the hinge radial dimension 115 to allow the strut to bend elastically to a radius of curvature with the radius in the direction of the strut radial dimension 155, this radius of curvature will be referred to as the strut radial radius of curvature 95 (see FIG. 3). In one preferred embodiment the strut radial dimensions 155 are preferably less than the radial thickness of prior art metal wire or uniform metal tubes that are formed into a prior art stent. The small strut radial dimension 155 allows the struts 10 to undergo a crush deformation with the strut deforming elastically and allowing the hinge stent 5 to return to its initial unstressed state once the tissue crush applied force has been removed. In the hinge stent 5 of the present invention the hinge cross sectional area 120 can be varied independently of the strut cross sectional area 160 to provide the hinged stent with a variety of expansion force characteristics and other properties. The hinge width 105 is small in comparison to the strut width 150 such that the hinge can bend more easily with a hinge width radius of curvature 165. During expansion deformation, the hinge can bend within the uniformly curved hinge stent surface 90. If, for example, the hinge radial dimension 115 were equal to the hinge width 105 and each were equal to the diameter of a round wire, the bending moment of the hinge would be approximately 1.67 times larger than the round wire based on the equation for moment stated earlier. Thus for a similar magnitude of hinge width 105 in comparison to the diameter of a round wire, the hinge stent 5 in a nondeployed state can provide a greater outward extension force by the hinge to the struts 10 than a circular cross sectional or round wire. The hinge radial dimension 115 can also be increased in magnitude to provide an even greater moment of inertia to the hinge such that even larger moment is generated to produce larger extensional forces by the hinge stent 5. The larger hinge radial dimension prevents significant bending of the hinge in the radial direction during a crush deformation imposed onto the hinge stent by an external crush force.

In one preferred embodiment for the design of the self-expandable hinge stent 5, the hinge radial dimension 115 can be formed such that it is approximately equal to the radial thickness of a prior art metal wire or uniform radial thickness metal tube that is formed into a stent. A larger hinge width 105 will supply a greater implanted hinge stent 5 expansion elastic force as long as the hinge remains reversibly elastic. For a self-expandable hinge stent 5 the hinge width 105 can be smaller than the uniform radial thickness of the prior art stent allowing the hinge stent 5 to undergo a smaller amount of localized deformation associated with a bend to a specific radius of curvature and remain elastic throughout the deformation. A relatively longer hinge length 110 is preferred to be used in the self-expandable hinge stent 5 in comparison to the hinge length 110 for a balloon-expandable hinge stent 5 in order to provide the smaller amount of localized deformation. The self-expandable hinge stent 5 is preferably formed out of a metal with a higher elastic modulus than the prior art stents to provide greater outward expansion force without undergoing plastic deformation. Other prior art stents cannot be formed out of such high elastic modulus metal as the present hinge stent without affecting the flexibility of these stents in a crush deformation. The present hinge stent 5 uncouples the outward expansion force of the hinge stent 5 from the hinge stent flexibility in a crush deformation by providing a thin strut radial dimension 155 and other hinge dimensions that can be varied as discussed earlier. The hinge stent 5 of the present hinge stent 5 can thus produce an equal or greater expansion moment than prior art stents that are formed of lower modulus material in order to balance expansion force with implanted stent crush elastic force. This embodiment for the hinge stent 5 is particularly useful for a self-expandable hinge stent 5.

The hinge length 110 for the self-expandable hinge stent 5 is preferably longer than the hinge length 110 for the balloon-expandable hinge stent 5. As mentioned earlier, the longer hinge length 110 allows the deformation in expanding from a nondeployed state to a deployed state to be spread out over a longer length and allows the localized deformation within the hinge to remain less than the yield point necessary for plastic deformation to occur. The longer hinge length 110 also allows the implanted stent expansion elastic force to drop off in magnitude less over the expansion deformation from a nondeployed state to a deployed state. This allows the outward expansion elastic force to be more similar over a wide range of deployed or expanded diameters to which the hinge stent 5 is deployed. Thus the hinge stent 5 exerts a more similar outward expansion force regardless of small variations in vessel diameter.

For a balloon-expandable hinge stent 5 the hinge length 110 can be shortened such that the bending deformation of the hinge associated with expansion from the nondeployed state to the deployed state exceeds the yield point of the metal used to form the hinge stent 5. Shortening the hinge length 110 can focus the deformation of the hinge to a smaller hinge length 110 that undergoes a greater bending deformation along a hinge width 105 radius of curvature during expansion deformation. Thus a balloon-expandable hinge stent 5 formed of a high modulus metal can be required to undergo a plastic deformation in the hinge in an expansion deformation. This focusing of the deformation with a short hinge length 110 reduces the amount of rebound or partial return of the deployed diameter 85 of the hinge stent 5 toward the nondeployed diameter 75 of the nondeployed state that can occur in a balloon-expandable stent following the deflation of the balloon. This partial return or rebound occurs due to elastic deformation that occurs in part during a predominantly plastic deformation of the hinge. The hinge length 110 or the hinge stent 5 of the present invention can range from significantly less than to several times greater than the radial thickness of prior art stents. For a bending deformation of the hinge from one hinge width radius of curvature 165 to another hinge width radius of curvature 165, an increase in the hinge width 105 will also serve to increase the amount of hinge material exposed to deformation beyond the yield point of the metal. A larger hinge width 105 that undergoes plastic deformation beyond its yield point will provide the balloon-expandable hinge stent 5 with a greater implanted stent expansion holding force to hold the blood vessel outwards. Both hinge length 110 and hinge width 105 can be adjusted to provide inelastic flexure of the metal and plastic deformation. The hinge radial dimension 115 can be further adjusted to control the amount of force that is required to expand the hinge stent 5 to a particular amount of deformation during deployment of the hinge stent 5 and to control the amount of force exerted by the hinge stent 5 against the vessel wall in its deployed diameter 85. The balloon-expandable hinge stent 5 is able to uncouple the implanted stent expansion yield force associated with deformation of the hinge from the implanted stent crush elastic force associated with crush deformation of the strut. The balloon-expandable hinge stent 5 is thus able to be balloon expandable and yet be noncrushable due to characteristics of the strut related to the strut dimensions.

The strut cross sectional area 160 can be different than the hinge cross sectional area 120 and can be varied independently from it. The strut width 150 is designed to be large enough such that during expansion of the hinge stent 5 the struts 10 do not bend or flex significantly within the generally cylindrical uniformly curved hinge stent surface 90 of the hinge stent 5 with a radius of curvature having a radius aligned with the strut width 150. The strut width 150 for the hinge stent 5 of the present invention can be approximately equal to or up to more than triple the stent radial thickness of prior art stents. The hinge can therefore transfer its moment to the strut which then exerts an outward force upon the vessel wall to hold it outwards. Since the strut width 150 and strut radial dimension 155 provide approximately a rectangular cross sectional shape for the strut, the strut width 150 can be similar to the diameter of prior art struts or bars with a circular cross section and provide a greater moment in resisting bending deformation to a radius of curvature having a radius in the direction of the strut width 150 in order to provide support to hold the blood vessel outwards.

The strut radial dimension 155 is designed in a preferred embodiment to be thin in comparison to the hinge radial dimension 115 such that it can flex to form a radius of curvature with a radius aligned with the strut radial dimension 155; this bending deformation is similar to a crush deformation that would cause the hinge stent 5 to form an oval shape (see FIG. 3) for the hinge stent 5 surface rather than the generally cylindrical hinge stent surface 90 that it normally has. The struts 10 would remain elastic due to the small strut radial dimension 155 and due to a choice of metal such that the struts 10 do not exceed the elastic limit of the metal. The metal chosen for forming the hinge stent 5 could be chosen from a high elastic modulus material and still remain flexible to allow this bending deformation to form an oval shape due to the thin radial dimension. Prior art stents formed of a round wire or a bar of high modulus could not provide a combination of a large outward extension force and a low or soft crushing force; furthermore they would be prone to plastic deformation in the crush deformation. The larger radial thickness of prior art struts or bars which leads to their tendency to plastic deformation is necessary in the prior art devices in order to provide the necessary expansion forces provided by the expansion deformation. With this embodiment of the present invention, a hinge stent 5 could be formed entirely out of a high modulus metal with the hinge providing a large moment for providing a large implanted balloon-expandable hinge stent expansion holding force or self-expandable hinge stent expansion elastic force, and the strut allowing the hinge stent 5 to be bent elastically to an oval shape to without plastic deformation and therefore not becoming permanently crushed. Thus one embodiment of the present invention is a balloon-expandable hinge stent 5 that is balloon-expandable and non crushable.

The strut cross sectional area 160 can be altered independently of the hinge cross sectional area 120. An increase in strut radial dimension 155 will provide the strut with a greater resistance to bending to a strut radial radius of curvature 95. Thus the hinge stent 5 of the present invention can be designed to resistant crush deformation that would cause the hinge stent 5 to form an oval shape. The strut radial dimension 155 required to provide this additional resistance to crush deformation is smaller than the hinge radial dimension 115 which does not provide any significant deformation due to exposure to crush deformation forces.

The hinge stent 5 of the present invention has a strut length 145 that provides a lever arm that is associated with expansion from a nondeployed state to a deployed state and that is associated with crush deformation or forming an oval shape. The hinge stent 5 of the present invention can be formed with any number of struts 10 and with any strut length 145 that is suited to a particular application. The hinge of the present invention can provide a greater moment to hold the vessel open in a deployed state than the moment provided by prior art circular cross sectional wire stents of similar width. As stated earlier, the hinge can be designed with a larger hinge radial dimension 115, a larger hinge width 105, and with a metal of higher elastic modulus in order to provide a greater expansion moment. Therefore the hinge of the present invention can transfer a torque to a strut of larger strut length 145 than the length of other prior art round wire stents and provide a greater outward force against the blood vessel to hold it outward than a round wire stent or other stents. A longer the strut length 145 will require a stronger hinge moment in order to hold the blood vessel outwards with a specific expansion force. This concept was discussed earlier in the discussion of bending moments. The hinge of the present hinge stent 5 can also be designed to provide a smaller bending moment during the expansion deformation by providing a smaller hinge width 105 and a smaller hinge radial dimension 115. This smaller bending moment can be better suited to provide the outward expansion force to a smaller strut in order to hold the vessel outwards. The hinge stent 5 of the present invention can therefore be used to provide a short or a long strut length 145 in comparison to other prior art stents. The strut length 145 for the hinge stent 5 also impacts the flexibility or ease of the hinge stent 5 to form an oval shape. A long strut length 145 provides a greater percentage of the perimeter of the hinge stent 5 in the deployed state to be associated with the struts 10 in comparison to the hinges 23 or transition regions 25. Since the struts 10 are more flexible in a crush deformation than the hinges 23 or transition regions 25, the hinge stent 5 with longer struts 10 will be more flexible in forming an oval shape. Crush deformation is therefore tied to strut length in addition to strut width and strut radial dimension. The strut width 150 and strut radial dimension 155 are therefore tied to the strut length 145 in order to provide a hinge stent 5 with an ability to flex in crush deformation. For example, if the strut length 145 were to be reduced in length while trying to maintain the same crush flexibility and expansion strength, the strut radial dimension 155 would have to be reduced to compensate for the reduced flexibility due to the strut length 145, and the strut width 150 would be altered to provide a bending moment in the direction of the strut width 150 in order to transfer the same expansion force provided by the hinge.

Figure 6:
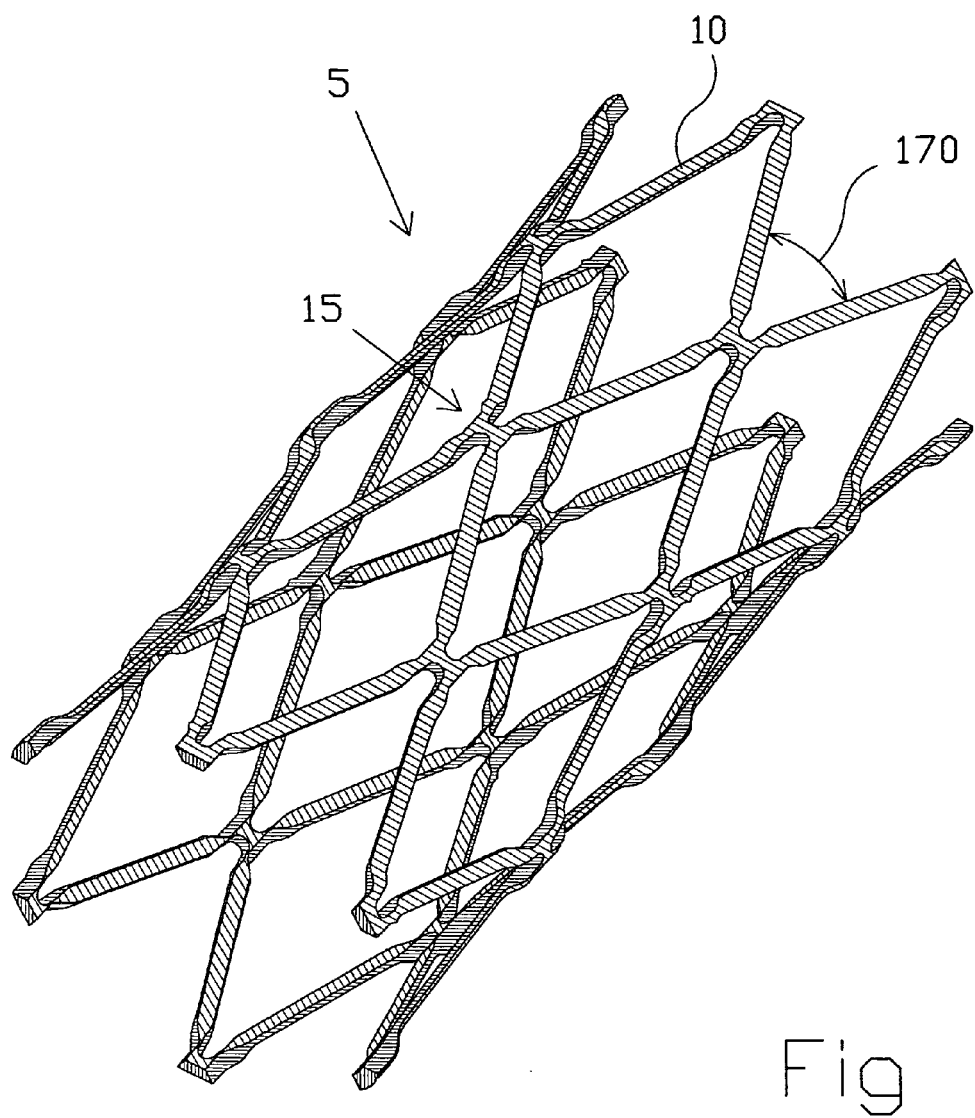
FIG. 6 is an isometric angled view of a hinge stent having a four strut per node body in a deployed state.

A deployment angle 170 (see FIG. 6) of the present hinge stent embodiment as shown in FIGS. 1A and 2A is preferred to remain small in the deployed state such that the deployed repeat unit length 80 (see FIG. 2A) is not significantly shorter than the nondeployed repeat unit length 65. A deployment angle 170 of less than approximately 50 degrees will provide a length reduction of less than 10 percent in going from a nondeployed state to a deployed state. A small percentage change in repeat unit length provides the hinge stent 5 with a capability for more accurate placement of the hinge stent 5 within the blood vessel under fluoroscopy.

The hinge stent 5 of the present invention can be designed such that the hinge will provide a large deployment angle 170 ranging from zero to over 190 degrees. The hinge of the present invention can be formed from a metal of large Young's modulus as stated earlier. The hinge can be formed of a thin hinge width 105 and a long hinge length 110 such that the moment maintained by the hinge will still be adequate even at a large bending deformation angle or deployment angle 170. Thus the hinge of the present invention can supply adequate outward force at a deployment angles 170 ranging from zero to over 190 degrees.

The transition regions 25 serve to join the hinges 23 to the struts 10. During the expansion of the hinge stent 5 from a nondeployed state to a deployed state the transition region 25 transfers the moment of the hinge to the strut without undergoing any significant transition region 25 bending. If the hinge stent 5 is exposed to a crushing deformation, the struts 10 will bend elastically to form a new strut radial radius of curvature 95 but the transition region 25 and the hinge will not bend in crush deformation. The transition region width 130, transition region radial dimension 135, and transition region cross sectional area 140 are such that the transition region 25 does not undergo significant bending deformation in either the direction of the transition region width 130 or transition region radial dimension 135. The transition region length 125 is preferably short or abrupt in order to maximize the length of the struts 10 or the hinge. The transition region width 130 ranges from the hinge width 105 to the strut width 150 and the transition region radial dimension 135 ranges from the hinge radial dimension 115 to the strut radial dimension 155. Stepped changes in hinge or strut cross sectional areas 160 are avoided to eliminate the possibility of metal fracture at that site. The transition region 25 is designed to transfer the moment generated by the hinge to the strut without bending in the direction of the transition region width 130 and to resist bending in the direction of the transition region radial dimension 135 when the hinge stent 5 is deformed with a crush deformation.

The hinge provides an outward expansion force against the vessel wall when the hinge stent 5 is in a deployed state. This outward force is an expansion holding force for a balloon-expandable hinge stent 5 and an expansion elastic force for a self-expandable hinge stent 5. As the balloon-expandable or self-expandable hinge stent 5 is exposed to a crush applied force that causes a crush deformation, the struts 10 of the hinge stent 5 exert a crush elastic force to resist crush deformation. It is preferred that the outward expansion force of the hinge is greater than the crush elastic force of the strut. Thus in a crush deformation, the deployment angle 170 does not undergo significant change. Other prior art stents tend to undergo local change in deployment angle 170 when exposed to crush deformation due to the high degree of coupling between expansion and crush characteristics provided by the prior art stents. The present hinge stent 5 uncouples the expansion characteristics from the crush characteristics. For a self-expandable hinge stent 5 the implanted hinge stent expansion elastic force provided by the hinge provides a larger outward force to hold the vessel outwards and maintains a constant perimeter in contact with the vessel wall without significant change in deployment angle 170, and allows the struts 10 of the hinge stent 5 to flex in a crush deformation to an oval shape elastically with a lower implanted stent crush elastic force. For a balloon-expandable hinge stent 5 the implanted hinge stent expansion holding force provided by the hinge provides a greater outward force to hold the vessel outwards with a constant perimeter without significant change in deployment angle 170, and allows the struts 10 of the hinge stent 5 to flex in a crush deformation to an oval shape elastically with a lower implanted stent crush elastic force.

The hinge length 110, hinge width 105, and hinge radial dimension 115 provide an outward expansion force to the hinge 23 as the hinge undergoes an expansion deformation in the uniformly curved hinge stent surface 90. The struts 10 transfer the expansion forces generated by the hinges 23 to the vessel wall. The struts 10 do not deform in the uniformly curved hinge stent surface 90 due in part to the larger strut width 150 in comparison to the hinge width 105. If the hinge stent 5 is subjected to a crush deformation such that it forms an oval hinge stent surface 93, the struts 10 have a strut length 145, strut width 150, and strut radial dimension 155 that will provide for bending of the struts 10 in the radial direction with an elastic deformation. The hinge 23 will not deform in the radial direction upon exposure to a crush deformation due in part to the large hinge radial dimension 115 in comparison to the strut radial dimension 155. A longer strut length 145 allows the hinge stent 5 to have a greater percentage of the hinge stent associated with the struts 10 in comparison to the hinges 23 and hence provides the hinge stent 5 with a greater flexibility in bending due to a crush deformation.

Figure 7:
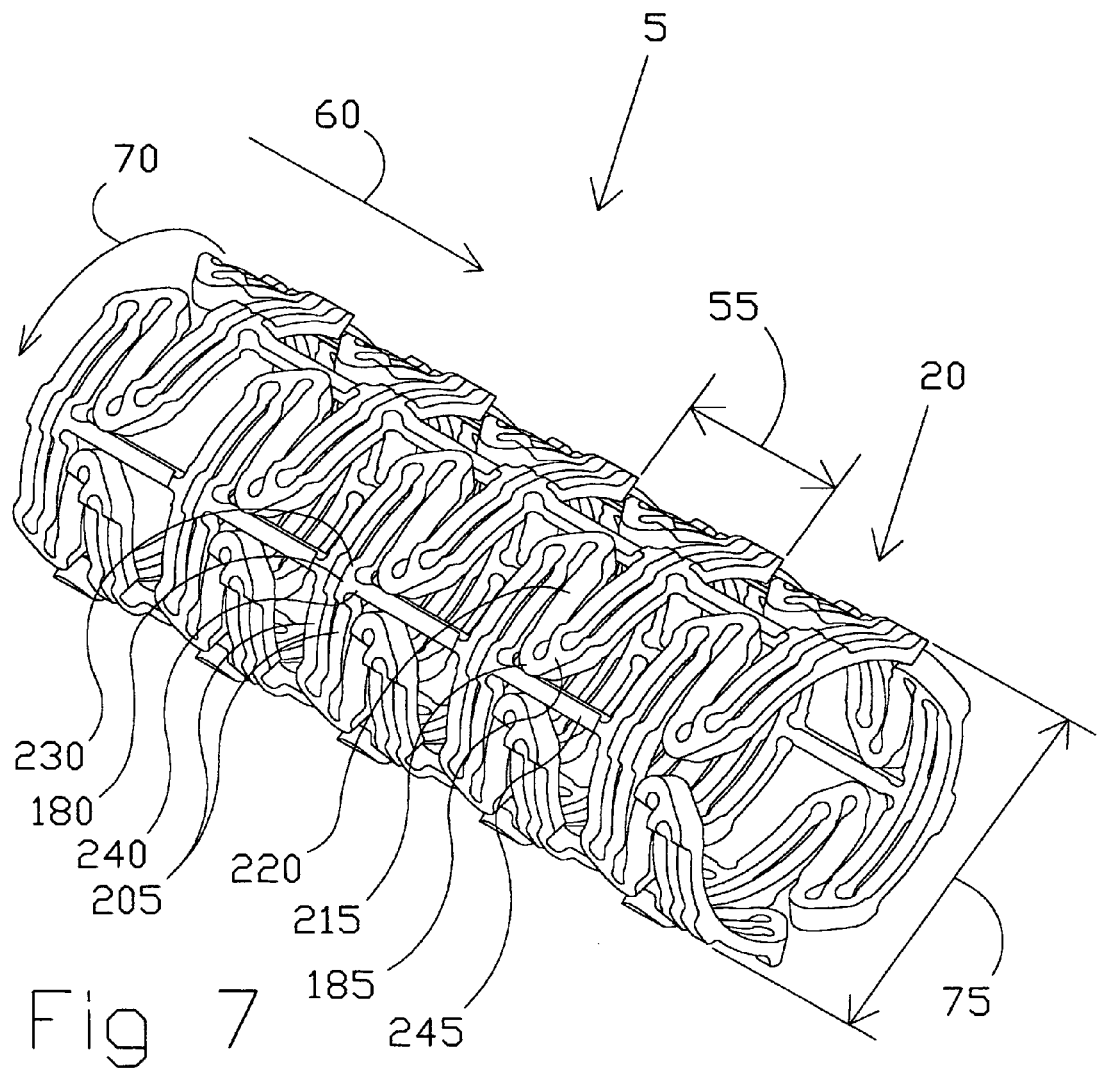
FIG. 7 is an isometric view of a hinge stent having a three strut per node body in a nondeployed state.
Figure 8:
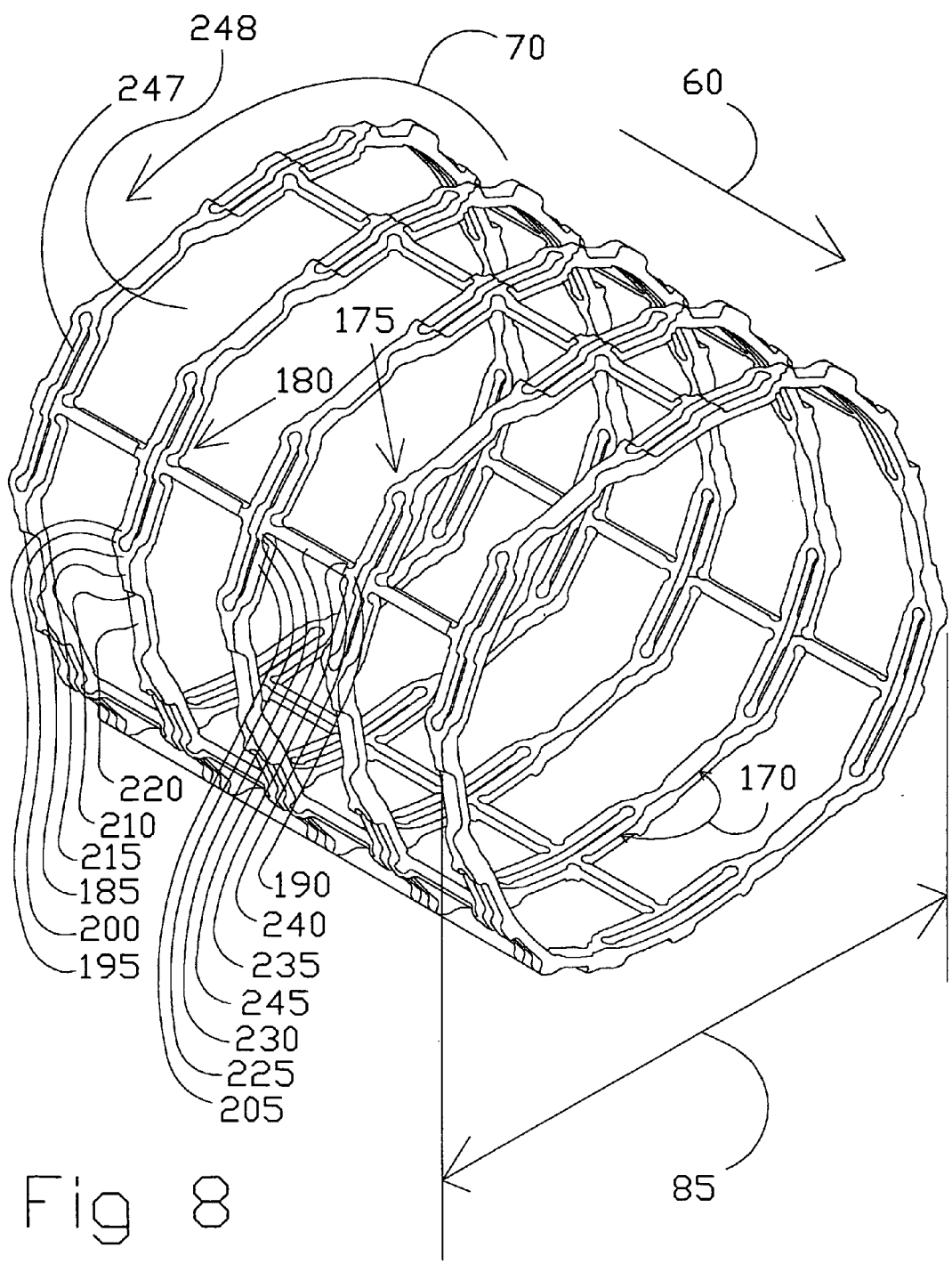
FIG. 8 is an isometric view of a hinge stent having a three strut per node body in a deployed state.
Figure 9:
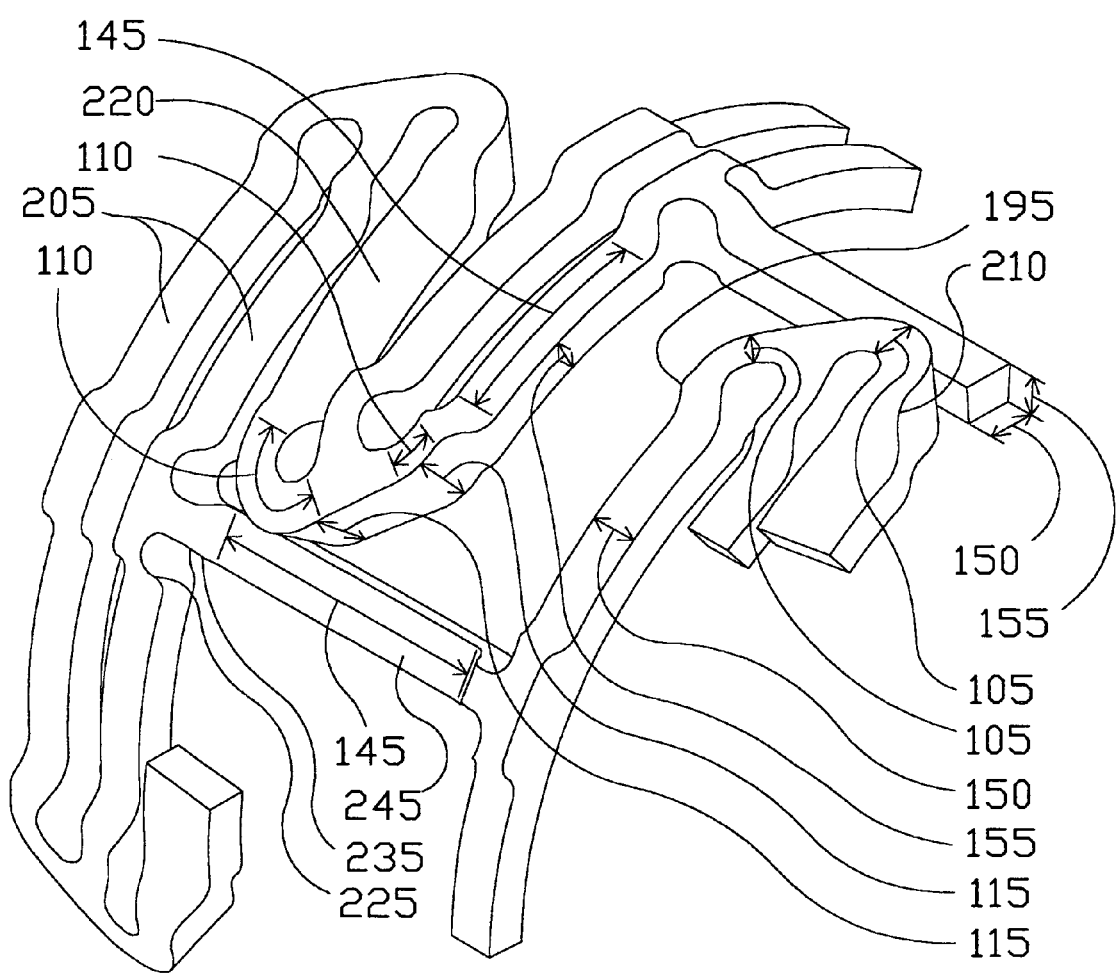
FIG. 9 is an enlarged detail view of a portion of the hinge stent shown in FIG. 7.
Figure 10:
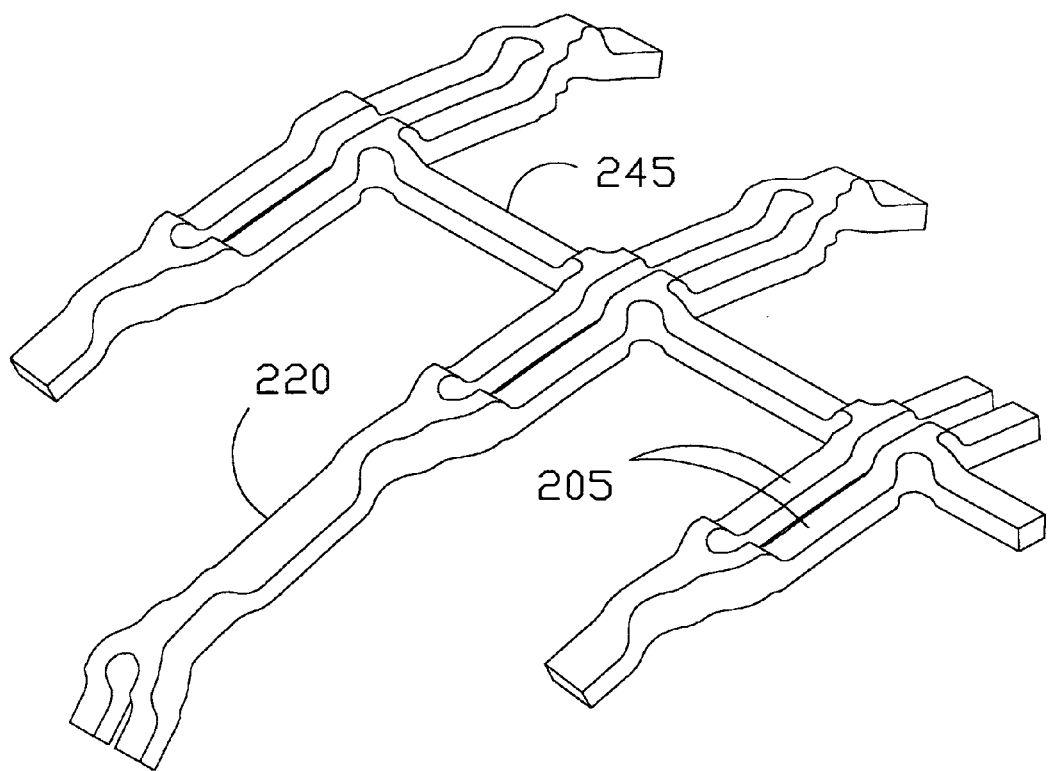
FIG. 10 is an enlarged detail view of a portion of the hinge stent shown in FIG. 8.

Another primary embodiment of the hinge stent 5 of the present invention is shown in FIG. 7 in a nondeployed state and in FIG. 8 in a deployed state. An enlarged detailed view of a portion of the hinge stent 5 shown in FIG. 7 is shown in FIG. 9 and an enlarged detailed view of a portion of the hinge stent 5 shown in FIG. 8 is shown in FIG. 10. Discussion of FIGS. 7-10 will occur together with reference numerals found collectively in these figures. In this embodiment three struts are joined to each node throughout the body of the hinge stent 5. Two different types of nodes 15 are found in this hinge stent 5, a Y node 175 and a T node 180. The Y node 175 has a small portion termed a Y hub 185 that does not deform significantly during an expansion deformation from the nondeployed state to the deployed state or during a crush deformation. Similarly the T node 180 has a small portion termed a T hub 190 that does not undergo a significant deformation. A node is not required to have a hub region and the T nodes 180 and Y nodes 175 of this embodiment could have been shown without the small T hub 190 and Y hub 185, respectively, without affecting the overall function of the hinge stent 5. The Y node 175 is joined via two Y arm transition regions 195 and via two Y arm hinges 200 to two arm struts 205, and the Y node 175 is also joined via a Y tail transition region 210 and via a Y tail hinge 215 to a tail strut 220. The T node 180 is joined via two T arm transition regions 225 and via two T arm hinges 230 to two arm struts 205, and the T node 180 is also joined via a T axial transition region 235 and via a T axial hinge 240 to an axial strut 245. The struts joined to the Y nodes 175 and T nodes 180 have strut widths 150, strut lengths 145, and strut radial dimensions 155; the hinges 215, 200, 240, & 230 associated with the Y nodes 175 and T nodes 180 have hinge widths 105, hinge lengths 110, and hinge radial dimensions 115 that bear the same reference numerals as described in FIG. 1A-6 in the first embodiment of the hinge stent 5 of the present invention. The dimensions for the transition regions for the present embodiment also bear the same reference numerals as described in FIGS. 1A-6. The arm struts 205, tail struts 220, axial struts 245, Y arm hinges 200, Y tail hinges 215, T arm hinges 230, T axial hinges 240, Y arm transition regions 195, Y tail transition regions 210, T arm transition regions 225, and T axial transition regions 235 found in this embodiment as shown in FIGS. 7-10 behave in the same manner as the struts 10, hinges 23, and transition regions 25, respectively described earlier for the first embodiment shown in FIGS. 1A-6. Specific differences between this embodiment shown in FIGS. 7-10 will be further discussed.

The hinge stent 5 of the embodiment shown in FIGS. 7-10 has a generally cylindrical shape with a deployed diameter 85 and a nondeployed diameter 75. The hinge stent 5 of this embodiment is made up of a stent section 20 formed of a single common pattern of struts and hinges throughout the entire length. Repeat units 55 are joined contiguously together and allow the stent section 20 to extend in an axial direction upon addition of additional repeat units. In this embodiment the nodes and struts form a closed structure to provide integrity to the structure and strength in the axial direction 60 and circumferential direction 70 of the hinge stent 5. The continuous structure of struts and hinges extend along the perimeter and throughout the length of the stent section. This continuous structure does not allow abrupt changes in stent diameter to occur as one portion of the stent is expanded to a deployed diameter, and does not allow stress risers to occur in the vessel wall.

This embodiment as shown in FIGS. 7-10 can be a self-expandable hinge stent 5 or a balloon-expandable hinge stent 5. In a nondeployed state and with a nondeployed diameter 75 the balloon-expandable hinge stent 5 can be mounted on a balloon of a balloon dilitation catheter for percutaneous delivery to the site of a vascular lesion. Once the hinge stent 5 has reached the site of the lesion the balloon of the balloon dilitation catheter can be expanded to expand the hinge stent 5 from a nondeployed state to a deployed state. The hinge stent 5 of this embodiment has significant axial flexibility in passing along a tortuous pathway to reach the site of the lesion.

Figure 11:
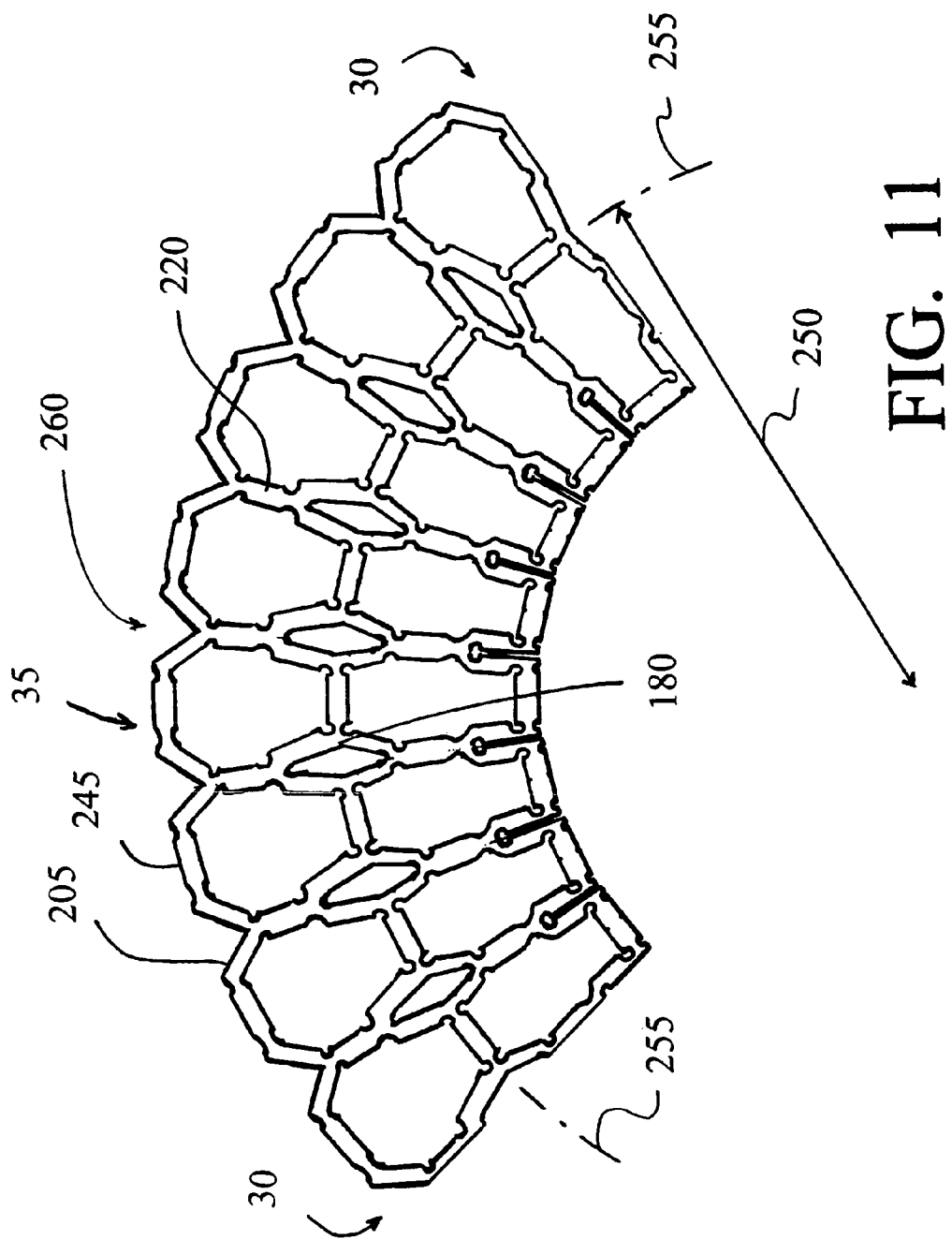
FIG. 11 is an illustration of a hinge stent having three struts per node similar to the hinge stent of FIG. 8 in a curved conformation in a deployed state.

The self-expandable hinge stent 5 of this embodiment can be contained in a delivery sheath that applies a compression applied force to maintain the hinge stent 5 in a nondeployed state for percutaneous delivery to the site of vessel lesion. The self-expandable hinge stent 5 also is very flexible in a nondeployed state such that it can be easily delivered through tortuous vessels to reach the lesion site. For a tubular shaped hinge stent 5 such as that shown in FIGS. 7-10 to pass along a tortuous pathway or around a curve requires that the portion of the stent on the outside of the curve be able to extend in length, or that the portion of the stent on the inside of the curve be able to compress in length, or that both can occur. Both the balloon-expandable and self-expandable hinge stent 5 of this embodiment obtain this axial flexibility by allowing the portion of the stent on the outside of the curve to extend in length and allow some compression along the inside of the curve. This extension in length can occur by allowing two T nodes 180 which are adjacent to each other to move apart from each other in an axial direction 60. Once the hinge stent 5 of this embodiment has reached the site of the vascular lesion, it is important that the hinge stent 5 remain flexible in an axial direction 60 in a deployed state. Often the vascular lesion can be located on a curved portion of a blood vessel and requires that the hinge stent 5 can extend along the outside radius of curvature of the curved vessel or compress along the inside radius of curvature. An illustration of a hinge stent with three struts per node, similar to that shown in FIGS. 7-10 is shown in a bent or curved configuration in FIG. 11. All reference numerals correspond to those elements previously or otherwise described.

The Y arm hinges 200 and T arm hinges 230 each have a hinge length 110, hinge width 105, and hinge radial dimension 115. The hinge radial dimension 115 can generally have a magnitude similar to the radial thickness of a standard prior art stent. In order to provide a greater flexibility to the hinge stent 5 in traversing around a tortuous path, the hinge radial dimension 115 for the Y arm hinges 200 and the T arm hinges 230 can be reduced in order to provide a greater flexibility to these hinges. For a balloon-expandable hinge stent 5 the hinge width 105 can be reduced to reduce the amount of force necessary to generate deformation of Y arm hinges 200 and T arm hinges 230 and allow the two adjacent T nodes 180 to move apart easily while traversing around a corner. This movement of the T nodes 180 away from each other can occur in a nondeployed state during insertion of the hinge stent 5 or after implantation of the hinge stent 5 in a curved portion of the blood vessel. For a self-expandable hinge stent 5 the hinge width 105 can be reduced and the hinge length 110 can be increased to reduce the amount of force necessary to generate deformation of the Y arm hinges 200 and T arm hinges 230 and allow the two adjacent T nodes 180 to move apart as the hinge stent 5 traverses around a corner. Therefore, this embodiment for a self-expandable or balloon-expandable hinge stent 5 can be made flexible in traversing around corners of a tortuous path in both the nondeployed state and the deployed state. The hinge stent 5 of this embodiment has a Y tail hinge 215 that is designed to provide a large expansion force to ensure that the hinge stent 5 is provided with a large hoop strength in a deployed state to hold the vessel outwards with adequate force. This Y tail hinge 215 is joined via a Y tail transition region 210 to a tail strut 220 with a large strut width 150 that transfers the large expansion force of the Y tail hinge 215 to the vessel wall. Increased hinge expansion force can be generated as discussed earlier in previous embodiments and include enlarging the hinge width 105 and hinge length 110. The Y arm hinges 200 and the Y arm struts 205 are connected in a closed loop 247 to ensure that a large hoop strength is maintained. This closed loop includes a Y node 175 connected to an arm strut, to a T node 180, to an arm strut, to a Y node 175, to an arm strut, to a T node 180, to an arm strut and back to the original Y node 175. The hinge stent also has a closed configuration 248 that provides integrity and stability in both the circumferential and axial direction. This closed configuration 248 consists of struts and hinges joined to form an enclosed space. Such a closed configuration 248 is formed by the tail struts 220, Y nodes 120, arm struts 205, T nodes 180, and axial struts 245. The geometry of the closed loop 247 along with having a long hinge radial dimension 115 for the hinges 200 & 230 of the closed configuration 248 allows the closed configuration 248 to maintain a large hoop strength. The flexibility of the hinges of the closed loop 247 allows the T nodes 180 to move apart easily during bending of the hinge stent 5 around a curved path. Thus the hinge stent 5 of the present invention can be flexible around corners and provide a large outward force to hold the vessel outwards. The closed configuration provides a structure of nodes and struts that extends both circumferentially as well as axially and is therefore continuous throughout the stent section. The closed configuration of this embodiment is a continuous configuration of nodes and struts with struts connected via hinges to the nodes forming the stent section of this embodiment. The continuous configuration of hinges and struts substantially along the perimeter and throughout the length of the stent section provide this hinge stent with hoop strength in the circumferential direction that is supported throughout the stent section including in the axial direction. The forces supplied by the hinge stent to hold the vessel outward are distributed through the nodes and struts throughout the entire stent section. The continuous structure of struts and hinges does not allow the stent section to undergo an abrupt change in diameter which could lead to stress concentration points in the tubular vessel being treated.

Stents in general and the hinge stent 5 of this invention can be exposed to a bending moment applied by the tissue of the blood vessel and surrounding tissue as they traverse through a tortuous vessel or are implanted in a curved portion of a blood vessel. This applied bending moment causes the hinge stent 5 as shown in FIGS. 7-10 to form a curved shape as shown in an illustration of a three strut per node hinge stent in FIG. 11. The hinge stent 5 as well as other prior art stents in general that are bent into a curved shape by a vessel will exert a bending moment outward against the blood vessel that is equal and opposite to the tissue applied bending moment. Boundary conditions imposed upon the ends of the hinge stent 5 require that the hinge stent radius of curvature 250 found along the stent axis 255 in the stent mid-length 260 is very often not the same as the hinge stent radius of curvature 250 at the ends 30 of the hinge stent 5. As a result, the stent exerts a lateral force against the side of the blood vessel as the stent tries to move back to an equilibrium shape that has a generally straighter stent axis than the curved stent axis imposed on the stent by the curved blood vessel. This lateral force imposed onto the vessel wall can generate a hyperplastic tissue growth at the ends of the stent and can lead to stenosis and eventual occlusion of the stent. This potential problem can be addressed with the hinge stent 5 of the present embodiment as shown in FIGS. 7-10 by providing a greater amount of flexibility to the Y arm hinges 200 and T arm hinges 230 located near the stent ends 30 in comparison to those located near the stent mid-length 260. Hinge flexibility can be increased by reducing the hinge width 105 and hinge radial dimension 115. Hinge flexibility can be gradually tapered such that those T arm hinges 230 and Y arm hinges 200 near the stent ends 30 have the greatest flexibility and they become gradually more stiff as the hinges get nearer to the stent mid-length 260. In a deployed state a hinge stent 5 of this design can provide enhanced healing at the ends of the stent. The outward expansion force exerted by the stent to hold the blood vessel outwards is independent of its flexibility or ability to bend around a curve. The outward expansion force exerted outward to hold the blood vessel outward is generated by the Y tail hinge 215 along with the geometry of the closed configuration. Thus, this embodiment of the hinge stent 5 can be very flexible in traversing around a corner of a blood vessel and have large expansion force to hold the vessel outwards. The hinges can provide tapered flexibility such that the stent is more flexible in bending around a curved passage near the ends of the stent. This tapered flexibility provided by the dimensions of the hinges can be equally well applied to the hinge stent embodiments shown in FIGS. 1A-6 as well as the hinge stent embodiments shown later in FIGS. 17A-27.

In a crush deformation, the embodiment of the hinge stent 5 shown in FIGS. 7-10 behaves very similarly to the hinge stent 5 shown in FIGS. 1A-6. The tail struts 220, and arm struts 205 have thin radial dimensions in comparison to the radial dimensions of the Y tail hinges 215, Y arm hinges 200, and T arm hinges 230. In a crush deformation, the tail struts 220 and arm struts 205 can bend elastically to a strut radial radius of curvature 95 (see FIG. 3) as the hinge stent 5 forms an oval shape. The strut lengths 145 for the tail struts 220 and the arm struts 205 also affect the ability of the hinge stent 5 to form an oval shape when subjected to a crush deformation. A longer strut length 145 will allow a greater percentage of the perimeter of the hinge stent 5 in a deployed state to be occupied by the struts 220 & 205 as opposed to hinges 215, 200 & 230 and transition regions 210, 195 & 225. Since the struts 220 & 205 are more flexible in a crush deformation than either the hinges 215, 200 & 230 or the transition regions 210, 195 & 225 longer struts tend to provide the hinge stent 5 with an increased flexibility to form an oval shape due to a crush deformation. The hinges will not bend to form a radius of curvature in the direction of the hinge radial dimension 115 due to the larger hinge radial dimension 115. During expansion from a nondeployed state to a deployed state the Y tail hinges 215, Y arm hinges 200, and T arm hinges 230 undergo a deformation. For a balloon expandable hinge stent 5 this deformation involves plastic deformation that was described in the embodiment shown in FIGS. 1A-6. The hinge width 105, hinge length 110, and hinge radial dimension 115 are all involved in determining the amount of expansion holding force applied by the stent in holding the blood vessel outwards. A short hinge length 110 helps to focus the deformation of the metal hinge to create a greater amount of plastic deformation. This focusing of the deformation reduces the amount of rebound effect or partial return of the deployed diameter 85 of the hinge stent 5 toward the nondeployed diameter 75 due to elastic deformation that accompanies the plastic deformation. A larger hinge width 105 serves to increase the amount of localized plastic deformation within the hinge for a particular deployment angle 170. A larger hinge radial dimension 115 provides a greater magnitude of stent expansion holding force for the balloon-expandable hinge stent 5 to exert against the vessel wall in a deployed state. For a self-expandable hinge stent 5 the deformation of the hinges 215 in going from a nondeployed state to a deployed state is elastic. A longer hinge length 110 provides the hinge stent 5 with less localized hinge deformation for a deployment to a particular deployment angle 170. The longer hinge also allows the drop off of expansion elastic force to be less during its deployment from a nondeployed state to a deployed state. The smaller drop off of expansion elastic force allows the hinge stent 5 to exert a more similar expansion elastic force for a wider range of vessel diameters. A smaller hinge width 105 and hinge radial dimension 115 will provide a smaller magnitude of stent expansion elastic force exerted by the hinge stent 5 against the vessel wall.

The tail struts 220 and arm struts 205 have a larger strut width 150 than any of the hinge widths 105. The strut width 150 allows the expansion force and moments generated by the Y tail hinges 215, Y arm hinges 200, and T arm hinges 230 to be delivered to the vessel wall to hold it outwards.

The T nodes 180 provide a contiguous junction between the axial struts 245 and the arm struts 205. Each T node 180 includes a T axial hinge 240 and a T axial transition region 235 that is joined contiguously to the axial strut 245. The T axial hinge 240 is similar to other hinges described and it has a hinge width 105 that is small in comparison to the axial strut width 150. The T axial hinge 240 ensures that the hinge stent 5 of this embodiment maintains a continuous stent axis without shifting due to possible misalignment of repeat units 55 along the hinge stent axial direction 60. The axial struts 245 maintain an axial length for the stent that does not change from its nondeployed state to its deployed state. Maintaining a constant axial length from the nondeployed state to the deployed state provides the hinge stent 5 of this invention with the additional advantage of accurate placement of the hinge stent 5 into the vasculature under fluoroscopy.

The balloon-expandable hinge stent 5 of the embodiment shown in FIGS. 7-10 is a noncrushable hinge stent 5. The advantages of a balloon-expandable stent provide the hinge stent 5 of this invention with an ability to position the stent accurately at the site of the lesion prior to deploying it to its expanded or deployed diameter 85. The maintenance of a constant axial length during deployment further enhanced the capability of this stent to be positioned accurately within the vasculature. This hinge stent 5 is balloon-expandable due to the plastic deformation which occurs in the Y tail hinges 215, the Y arm hinges 200, and the T arm hinges 230 during the deployed from a nondeployed diameter 75 to a deployed diameter 85. The balloon-expandable hinge stent 5 of this invention will not form a plastic deformation if exposed to a crush deformation. The tail struts 220 and the arm struts 205 will bend elastically during a crush deformation due to their thin radial dimension in comparison to the hinge radial dimensions 115. The larger hinge radial dimensions 115 for the Y tail hinges 215, the Y arm hinges 200, and the T arm hinges 230 will not allow these hinges to deform in a radial direction during exposure to a crush deformation. Exposure of the hinge stent 5 to crush deformation will also not cause the hinges to change in deployment angle 170. The Y tail hinge 215 has enough strength due to its hinge dimensions and the metal of construction. The Y arm hinges 200 and T arm hinges 230 are stabilized by the geometry of the closed construction as described earlier. This hinge stent 5 is ideally suited for placement in the carotid artery of the body where placement of a stent is important and the stent cannot be crushed due to externally applied forces to the neck of the individual. Then balloon-expandable hinge stent 5 of the present invention is therefore balloon-expandable and non-crushable.

The self-expandable hinge stent 5 of the embodiment shown in FIGS. 7-10 and other embodiments of the present invention provide a stent with the property that the inserted stent expansion elastic force with which the hinge stent 5 pushes out against the sheath during stent insertion and the stent expansion elastic force with which the hinge stent 5 exerts outwards against the vessel wall are independent and uncoupled from the implanted stent crush elastic force with which the hinge stent 5 exerts against crush deformation. The advantage of this property is that the hinge stent 5 can hold a vessel outward with a very large force and yet be very soft or easily flexible in a crush deformation. This property can help reduce hyperplastic growth and stenosis that can occur at or near the ends of the stent and within the blood vessel near the ends of the stent. Since the expansion elastic force is uncoupled from the crush elastic force, it is equally possible to form a hinge stent 5 with very low expansion elastic force and a very large crush elastic force. A hinge stent 5 of this character would be very difficult to crush or form an oval shape and yet the force that it exerted outwards against the vessel wall could be very low. A hinge stent 5 of this character would be well suited to a vessel of the body with a thin wall that did not require a large outward expansion elastic force to hold it open, but could be exposed to a large crushing force. Some veins of the body may be suitable candidates for a hinge stent 5 of this character. The Y tail hinges 215, the Y arm hinges 200, and the T arm hinges 230 with hinge widths 105 smaller than strut widths 150 and radial dimensions larger than strut radial dimensions 155 provide the expansion elastic force for the self-expandable hinge stent 5. These hinges 215, 200, & 230 undergo elastic deformation as the hinge stent 5 expands from the nondeployed diameter 75 to the deployed diameter 85. The hinge lengths 110 can be long enough to provide elastic deformation of the hinges 215 during the expansion deformation. Due to the larger hinge radial dimension 115 the hinges 215, 200 & 240 will not undergo deformation in the radial direction associated with a crush deformation. The hinges 215, 200 & 240 will also not change in their deployment angle 170 as the hinge stent 5 is exposed to a crush deformation. The tail struts 220 and arm struts 205 have a thin radial dimension to provide for elastic bending to a radial radius of curvature 95 when exposed to crush deformation or forming an oval shape. A longer length for the struts provides the hinge stent 5 with a greater percentage of the stent perimeter associated with struts 220 & 205 as opposed to hinges 215, 200 & 230 or transition regions 210, 195 & 225. This can provide a more flexible hinge stent 5 in a crush deformation in forming an oval shape due to elastic bending of the struts. The large strut width 150 provides the hinges 215, 200 & 230 with a beam that will transfer the elastic expansion force outward against the vessel wall without bending in the direction of the strut width 150. The self-expandable hinge stent 5 therefore has the Y tail hinges 215, the Y arm hinges 200, and the T arm hinges 230 for providing expansion elastic force, and has tail struts 220 and arm struts 205 for providing crush elastic force.

Figure 12:
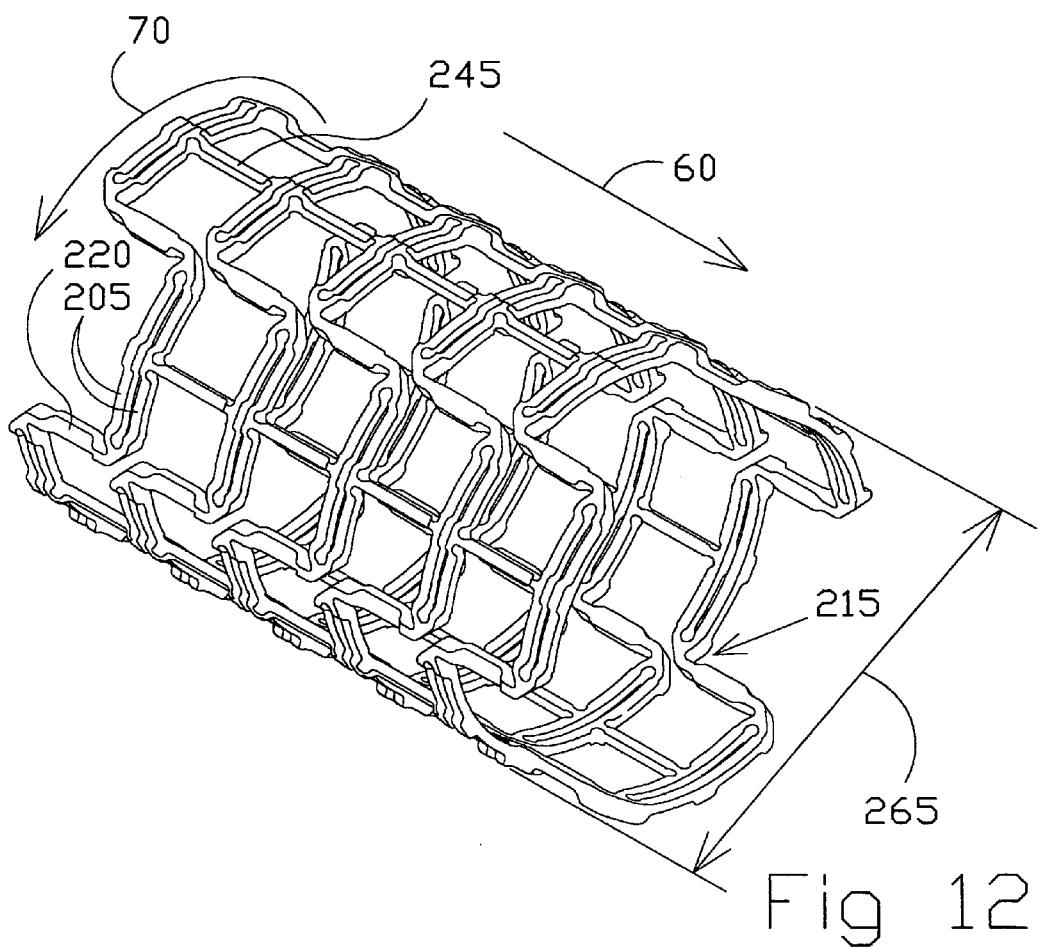
FIG. 12 is an isometric view of a hinge stent having a three strut per node body in an intermediate state.

The embodiment of the hinge stent 5 shown in FIGS. 7-10 can be machined using machining techniques described for the embodiment shown in FIGS. 1A-6. For the balloon-expandable hinge stent 5 a metal tube with an intermediate diameter 265 as shown in FIG. 12 between the nondeployed diameter 75 and the deployed diameter 85 can be used as a starting material. Standard mechanical machining of the outer surface of the tube can be performed to form the outer contour of all the hinges, transition regions, and struts of the hinge stent. Laser machining, chemical etching, electro-chemical machining, mechanical machining, or other machining techniques can then be used to remove metal material and leave the structure as shown in FIG. 12. The tubular structure shown in FIG. 12 could then be compressed down to a smaller nondeployed diameter 75 such as shown in FIG. 7 forming the hinge stent 5 in a nondeployed state. Machining the balloon-expandable hinge stent 5 in an intermediate state with an intermediate diameter 265 allows the outer contour of the Y nodes 175, T nodes 180, arm struts 205, tail struts 220, and axial struts to be easily machined in either an axial or circumferential direction 70. The laser, chemical, electro-chemical, or other machining techniques used to form the strut widths 150, hinge widths 105, and other dimensions of the Y and T nodes (175 & 180) and the arm, tail, and axial struts (205, 220, & 245) can also be more easily performed with respect to an axial or circumferential direction 70. The deformation performed on the Y tail hinges 215 in going from the intermediate state to the nondeployed state is less than the deformation that the Y tail hinge 215 encounters during its deployment from the nondeployed state to the deployed state. As the Y tail hinge 215 is deformed from the nondeployed state as shown in FIG. 7 during the deployment of the hinge stent 5 it will pass through the intermediate state as shown in FIG. 12 and will continue to be deformed until it reaches the deployed state as shown in FIG. 8. The deformation of the Y tail hinge 215 in going from the intermediate state to the nondeployed state is in the opposite direction as the deformation in going from the nondeployed state to the deployed state. Alternately, it is understood that the balloon-expandable hinge stent 5 of this embodiment can be machined in the nondeployed state as shown in FIG. 7. In this case the hinge stent 5 would not require significant further compression to a smaller diameter prior to deployment to the deployed diameter 85. A small amount of compression of the nondeployed hinge stent 5 can be performed in order to enhance the attachment of the hinge stent 5 to the balloon of a balloon dilitation catheter for insertion into the vasculature. All reference numerals correspond to those elements previously or otherwise described.

The self-expandable hinge stent 5 of the present invention can be machined using the same techniques described for the balloon-expandable hinge stent 5 using a metal tube with a deployed diameter 85 as shown in FIG. 8. The hinge stent 5 could then be machined with a deployed diameter 85 and folded to form a nondeployed diameter 75 as shown in FIG. 7. The hinge stent 5 is placed within a sheath which holds the hinge stent 5 in the nondeployed diameter 75 and allows the hinge stent 5 to be delivered to the site of the vessel lesion where it is allowed to expand out to its deployed diameter 85. The self-expandable hinge stent 5 can also be machined with a smaller diameter than the deployed diameter 85. Metal hardening techniques, metal elastic memory techniques such as those known in the art of working with Nitinol or other alloys, or other techniques can be employed to provide elastic behavior to all the hinges of the hinge stent 5 of the present invention.

Embodiments of the hinge stent 5 of the present invention have been described which have four struts per node and three struts per node throughout the stent section body 35. The four strut per node embodiment and the three strut per node embodiment each were formed of a stent section 20 having a strut and hinge conformation with a uniform pattern along the perimeter and extending throughout the axial length of the stent section body 35. The hinge stent 5 of the present invention can include a stent section which includes a varying number of struts per node ranging from two struts per node to approximately six struts per node. A hinge stent structure could be formed of a single stent section with a varying number of nodes and struts that extends throughout the stent section body 35. Such a hinge stent can be formed, for example, by joining a portion of a stent section of the embodiment shown in FIGS. 1A-6 with a portion of a stent section of the embodiment shown in FIGS. 7-10. The end nodes of each portion, for example, can be shared or form common nodes between each portion. The hinge stent 5 of the present invention can also be formed of stent sections 20 which are joined with uniformly spaced junctions along the perimeters of each stent section 20, with a first section having a specific number of struts per node and being joined to a second section that has another number or a varying number of struts per node and positioned generally axially from the first section. A hinge stent 5 of this structure would be comprised of more than one stent section with struts and hinges extending along a perimeter and also throughout the stent section body 35. The hinge stent 5 of the present invention can additionally be formed of two or more stent sections 20, each stent section 20 being joined together with an adjacent section by one or more section connectors, each section being comprised of repeat units. Such section connectors can be formed of nodes and struts which are similar to the nodes and struts with hinges connecting the nodes with the struts described thus far in this disclosure or the section connectors can be formed of a metal element as will be described later in this disclosure.

Figure 13A:
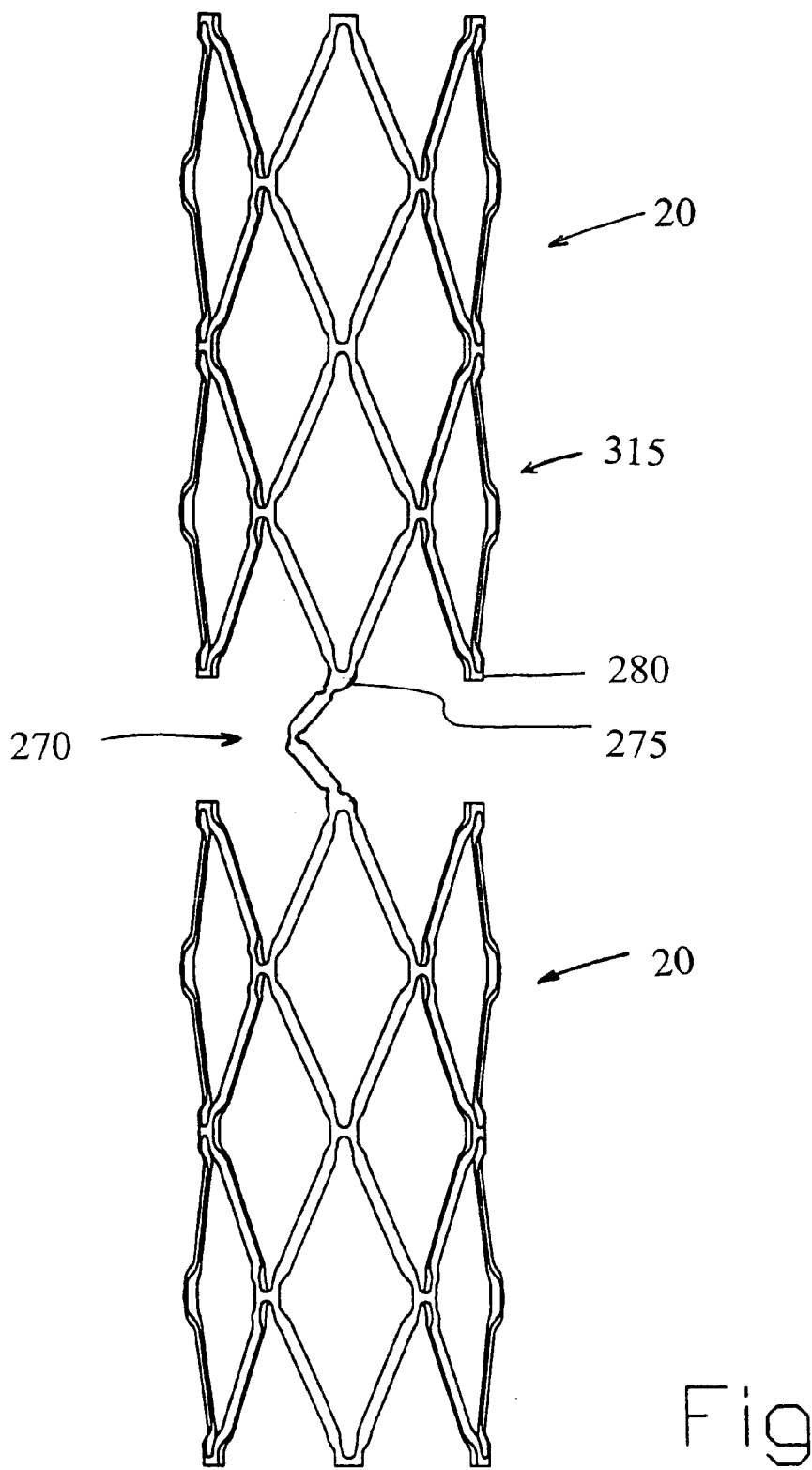
FIG. 13A is a frontal view of two stent sections joined by a hinged interconnector.
Figure 13B:
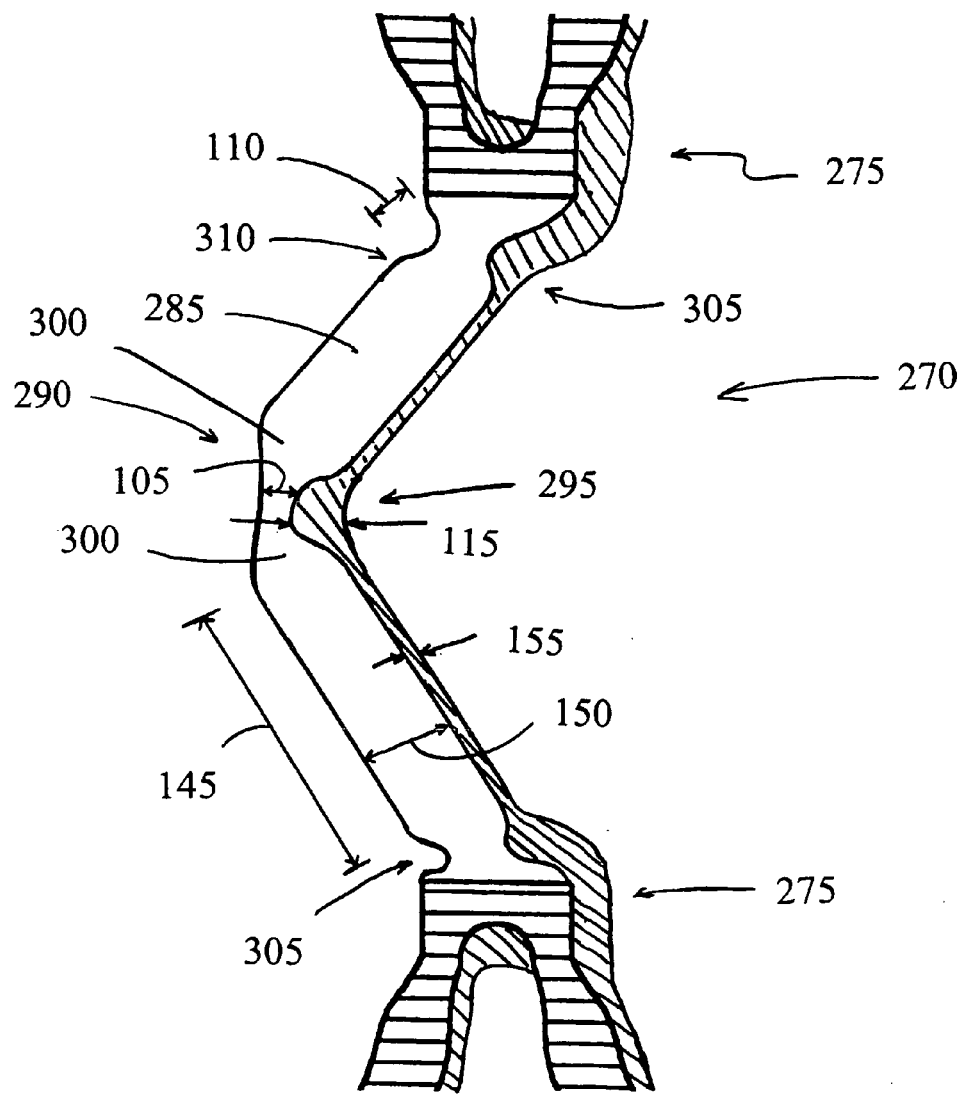
FIG. 13B is an enlarged detail view of a hinged interconnector.

FIGS. 13A and 13B show an embodiment of the hinge stent 5 of the present invention with two stent sections 20 being joined contiguously together by a hinged interconnector 270. The hinged interconnector 270 is comprised of at least one strut and is joined to at least one connecting node 275 from each of the sections to which it is joined, each node having a hinge that is connected and providing flexure with respect to a strut of the hinged interconnector. Nodes and struts which form a hinged interconnector 270 have a structure that is similar to the node and strut structure that has been described in the embodiment of FIGS. 1A-6 and FIGS. 7-10. A hinged interconnector 270 can have several nodes and struts joined together and joined to connecting nodes 275 of each section. This hinge stent 5 does not form a single stent section 20 as described earlier in the embodiment shown in FIGS. 1A-6 or the embodiment shown in FIGS. 7-10, but instead has more than one stent section 20. The stent sections 20 being joined in this embodiment are similar in structure to the stent section 20 shown in the embodiment of FIGS. 1A-6 although stent sections of the embodiment shown in FIGS. 7-10 could equally have been shown joined by the hinged interconnector 270. Other end nodes 280 at the end of the stent section 20 are shown not joined to an hinged interconnector 270. The hinged interconnector 270 is joined to a connecting node 275 of each stent section 20. The hinged interconnector 270 of this embodiment has two connecting struts 285 that are joined together by a flex node 290 that consists of a flex hinge 295 and two flex transition regions 300. The connecting node 275 of each stent section 20 that is to be joined has a connecting hinge 305 that is joined to a connecting transition region 310. The connecting transition region 310 of the connecting node 275 is joined to one connecting strut of the hinged interconnector 270. The hinged interconnector 270 of this embodiment of the hinge stent 5 provides an ability of the hinge stent 5 to be more flexible in traversing around a curved blood vessel during insertion as well as more flexibility during implant in a curved vessel. The hinged interconnector 270 also supplies axial length stability and transfer of expansion and crush forces in the axial direction. The hinged interconnector 270 allows the portion of the hinge stent 5 located in the outside of the curve to extend in axial length and the portion of the hinge stent 5 on the inside of the curve to compress in axial length. The hinged interconnector 270 can increase or decrease in length along the axial direction of the hinge stent due to flexure from one or more of its hinges.

The connecting hinges 305 and the flex hinge 295 have a small hinge width 105 in comparison to the strut width 150 such that these hinges can deform easily either plastically or elastically as the hinge stent 5 is placed into a curved blood vessel pathway. A longer hinge length 110 for the connecting hinge 305 or the flex hinge 295 allows a greater amount of hinged interconnector 270 deformation to occur while remaining elastic. A shorter hinge length 110 can be used to focus the deformation into a smaller region of the connecting hinge 305 or the flex hinge 295 and generate a greater percentage of localized plastic deformation within the hinge with less rebound or partial return to the initial hinge shape or initial hinge conformation. The strut radial dimension 155 is small in comparison to the hinge radial dimension 115 to allow for ease of elastic deformation of the strut to undergo a bending deformation in the direction of its radial dimension in passing around a curved vessel. The large hinge radial dimension 115 and large strut width 150 provide a torque characteristic in the circumferential direction 70 that can be transmitted from one stent section 20 to the adjacently joined stent section 20. A longer strut length 145 will provide a greater percentage of the hinged interconnector 270 to be associated with the connecting struts 285 in comparison to the flex hinges 295, connecting hinges 305, connecting transition regions 310, or flex transition regions 300. An increased strut length 145 will allow the hinged interconnector 270 to provide a greater flexibility to the hinge stent 5 in passing around curved vessels.

Figure 14:
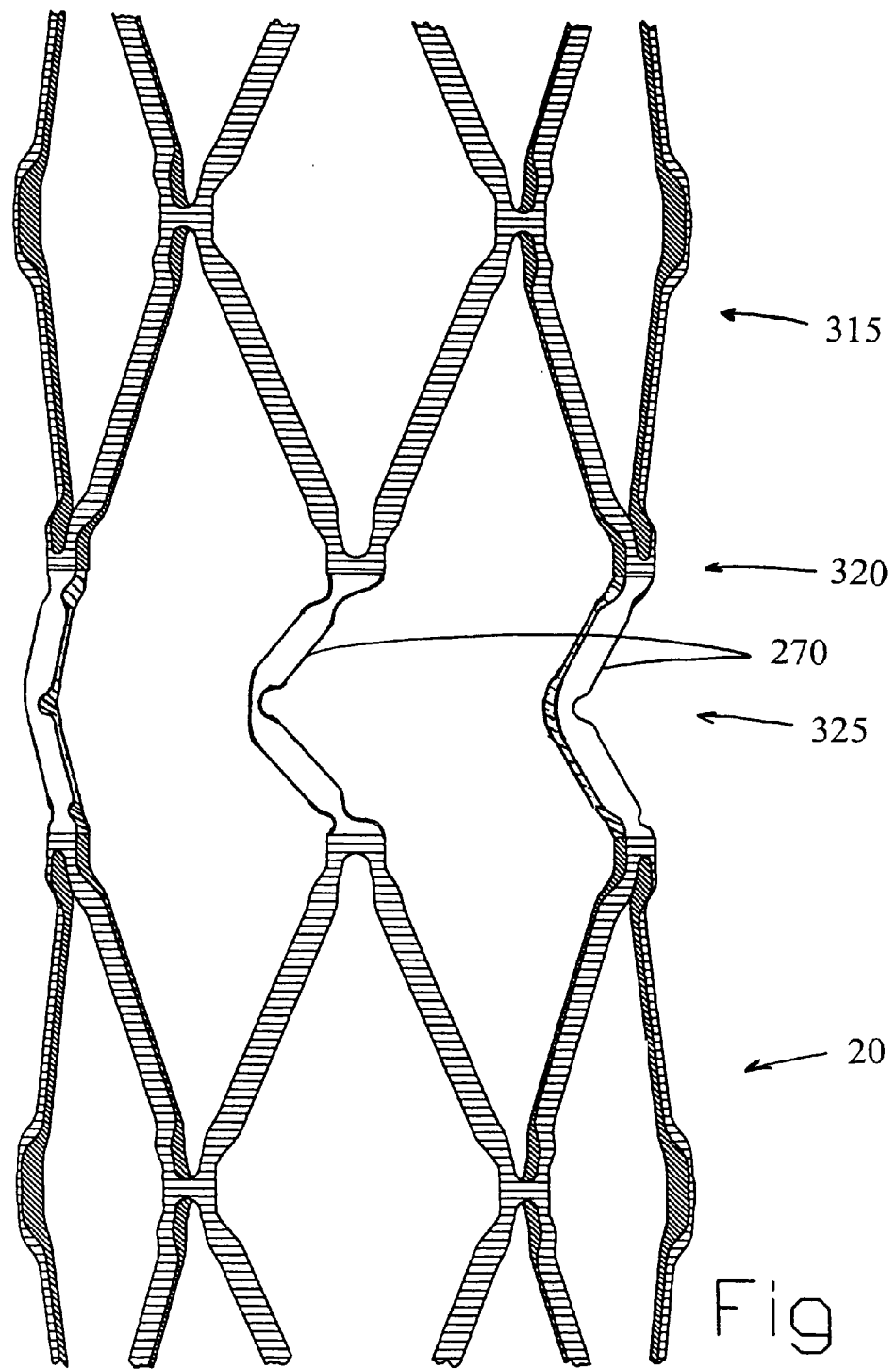
FIG. 14 is an isometric view of two stent sections joined by several hinged interconnectors.

Each end node 280 (see FIG. 13A) of a stent section 20 can be formed into a connecting node 275 and connected via an hinged interconnector 270 to another stent section 20 to form an embodiment of the hinge stent 5 of the present invention. This embodiment is shown in FIG. 14 where two sections similar to the embodiment shown in FIGS. 1A-6 are connected in a contiguous and a uniform manner along the perimeters of each stent section 20. The interconnectors 270 comprised of nodes and struts used in this embodiment are the same as the interconnectors 270 shown and described in FIGS. 13A and 13B although other types of interconnectors 270 can be used. The hinge stent 5 of this embodiment has four strut per node portions 315 that are similar to the stent section body 35 shown in the embodiment of FIGS. 1A-6. The hinge stent 5 also has a three strut per node portions 320 and two strut per node portions 325. This hinge stent 5 embodiment will be very flexible in an axial direction 60 due to the three strut per node portions 320 and two strut per node portions 325. As the hinge stent 5 of this embodiment is placed into a curved portion of a blood vessel, these portions can extend and compress as described in the embodiment shown in FIG. 13 providing this hinge stent 5 with great flexibility.

Figure 15:
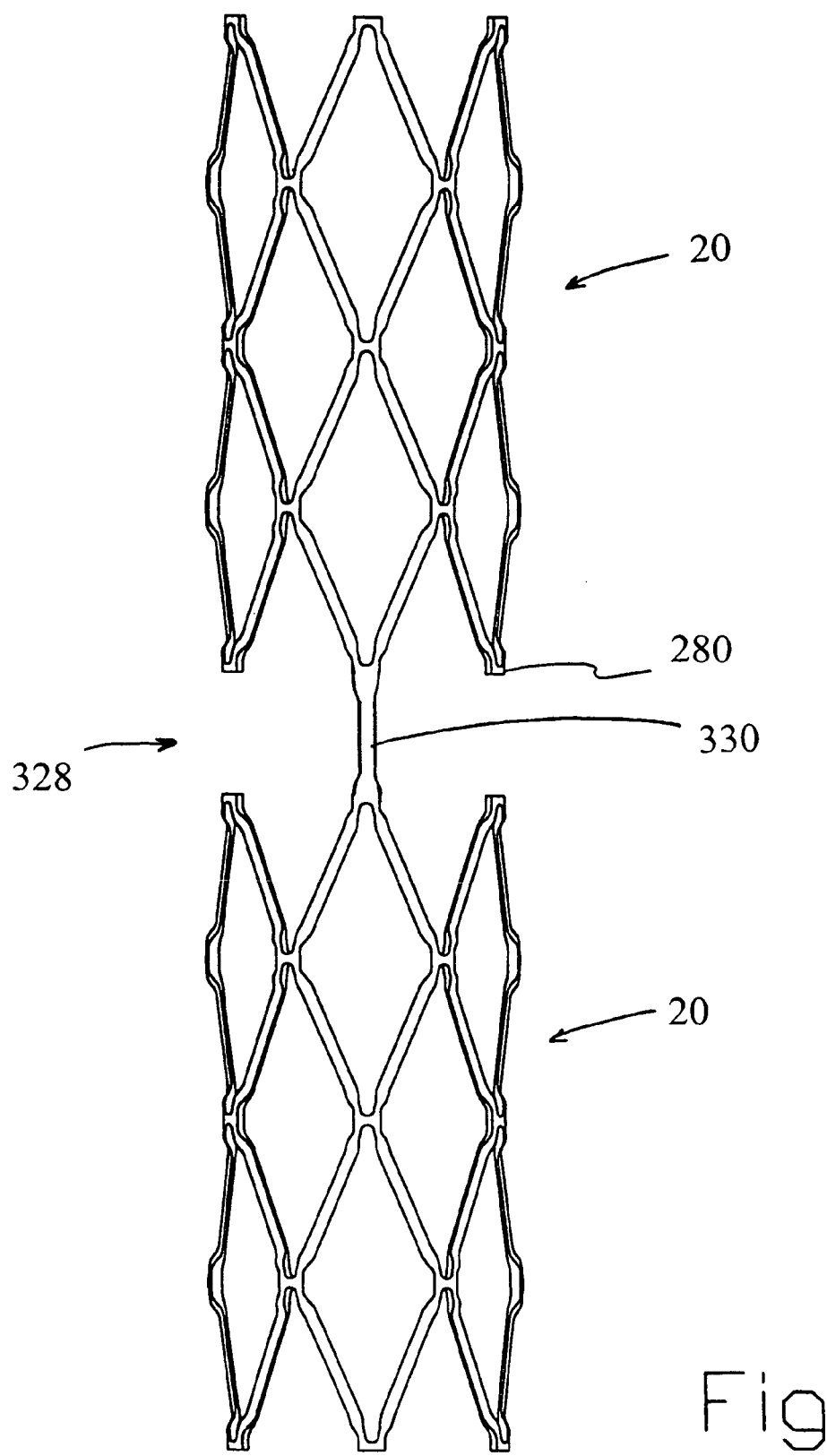
FIG. 15 is a frontal view of two stent sections joined by a straight leg element.
Figure 16:
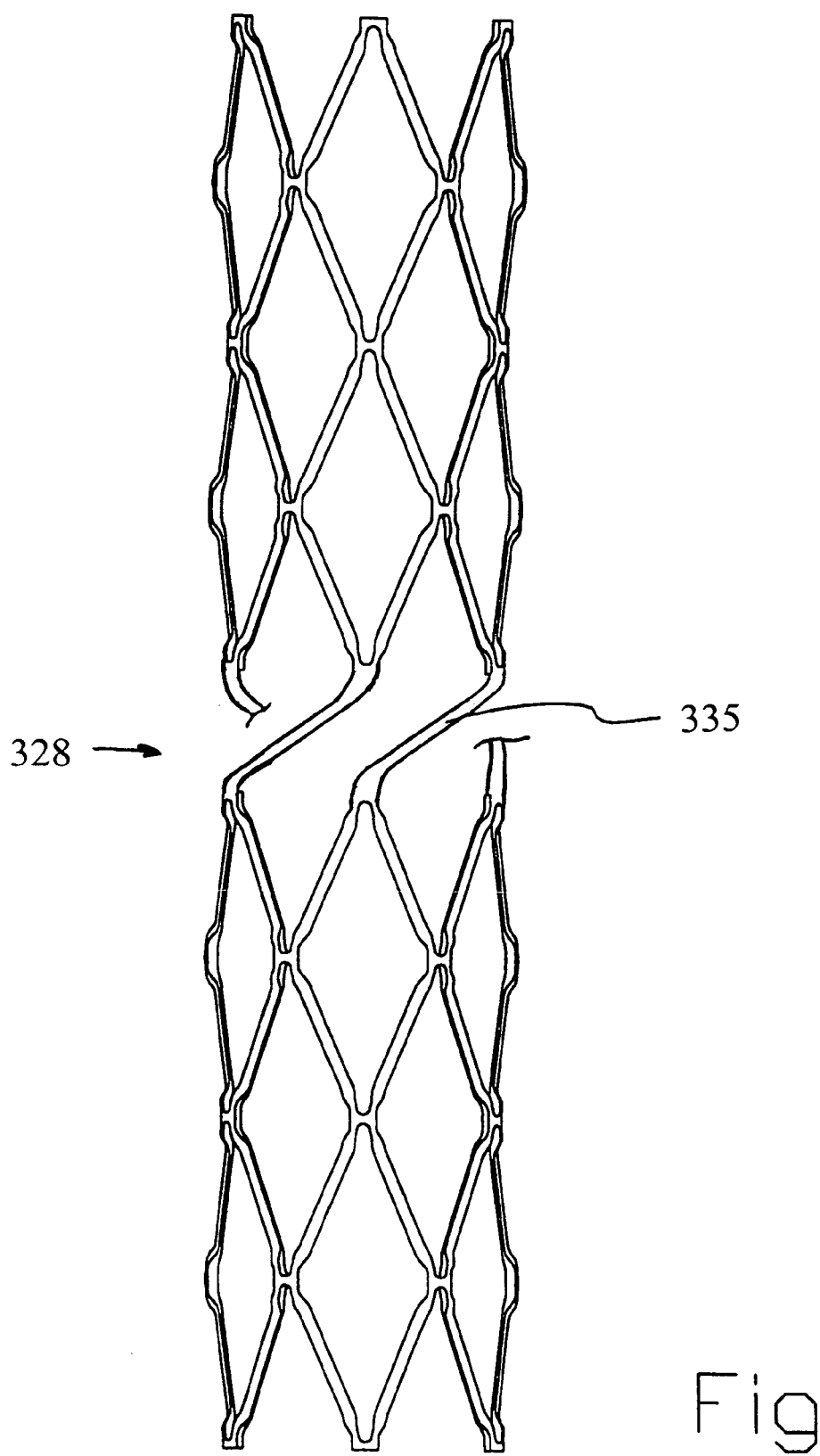
FIG. 16 is a frontal view of two stent sections joined by a curved leg element.

Another embodiment of the hinge stent 5 of the present invention can be formed by connecting stent sections 20 together with a connecting element 328. The connecting element 328 does not contain struts or nodes as shown in the embodiments of FIGS. 1A-6 or 7-10 or described for the interconnector 270. The connecting element 328 is not joined to each stent section via a hinge that is joined or directed toward the connecting element 328. Such an embodiment is shown in FIG. 15 where a straight leg element 330 is used to join two stent sections 20 together. The stent sections 20 shown in this embodiment are similar to the stent section 20 shown in the embodiment of FIGS. 1A-6 although stent sections of another embodiment of this invention could equally have been shown. The straight leg element 330 is shown connecting an end node 280 of one stent section 20 with an end node 280 of another stent section 20. The connecting element 330 could connect directly to a hinge portion of end node 280 although this structure would not provide the flexibility of the hinged interconnector 270 found in FIG. 13B. The hinged interconnector 270 shown in FIG. 13B has a connecting hinge 305 that provides for specific movement of the interconnector 270 in the uniform surface of the hinge stent and not bend in the radial direction of the hinge stent. The connecting element 328 provides the hinge stent 5 with axial flexibility such that the hinge stent 5 can easily traverse a tortuous path in a nondeployed or deployed state. The straight leg element 330 is not required to align with the axial direction 60 of the hinge stent 5 in order to provide extension or compression properties to the appropriate outside or inside portions, respectively, of the hinge stent 5 in traversing a curved vessel. The connecting element 328 can also have the form of a curved leg element 335 as shown in FIG. 16. A curved leg element 335 provides the necessary extension along the outside of a curve or compression along the inside of a curve to the hinge stent 5 as it traverses along a curved path within a blood vessel. The curved leg element 335 can be place between end nodes 280 (FIG. 13A) of individual stent sections 20 that are aligned in a generally axial direction 60 or can be placed between end nodes that have been offset as shown in FIG. 16. It is understood that any embodiment of the hinge stent 5 of the present invention can be used with interconnectors 270 or connecting element 328 to join stent sections 20.

Figure 17A:
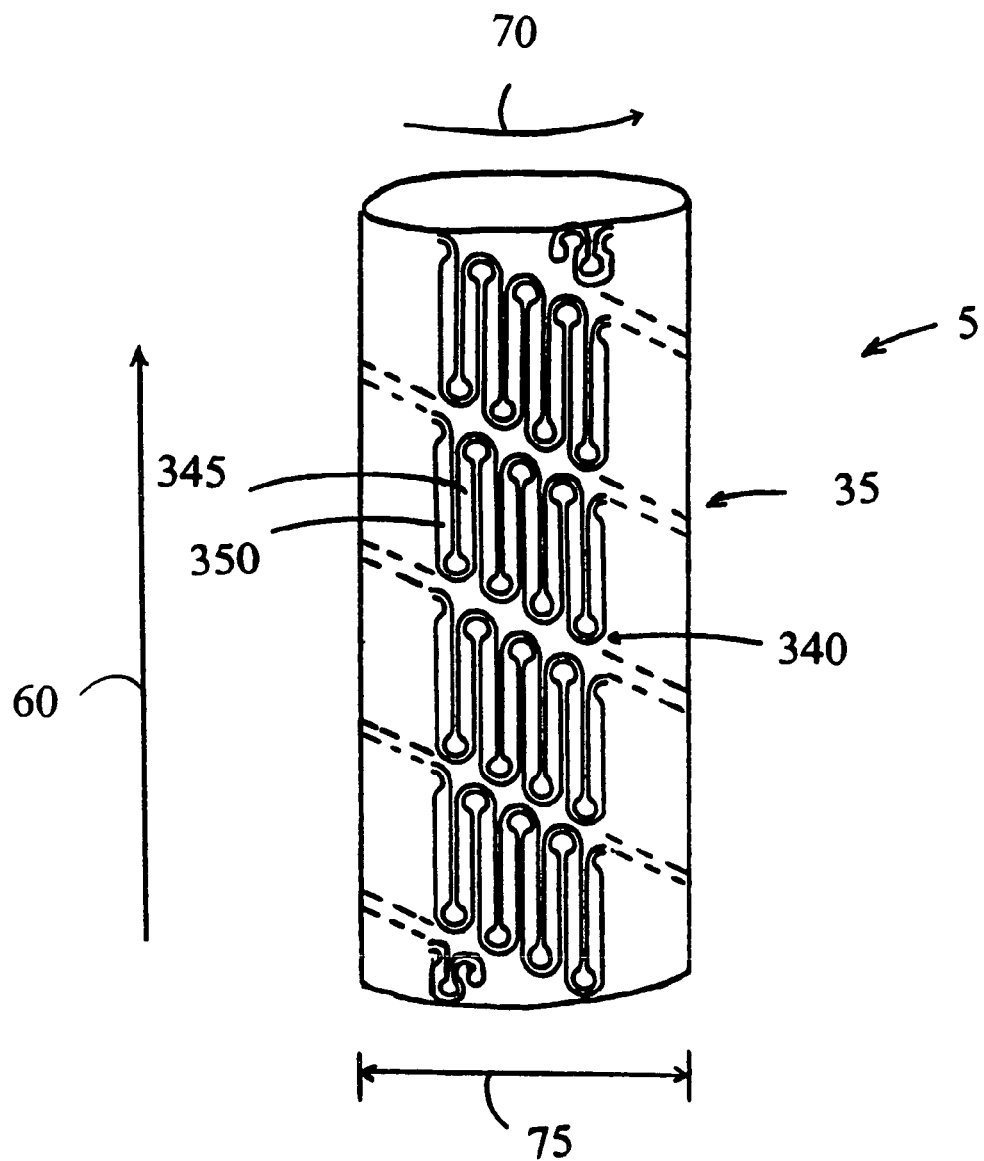
FIG. 17A is an isometric view of a hinge stent in a nondeployed state.
Figure 17B:
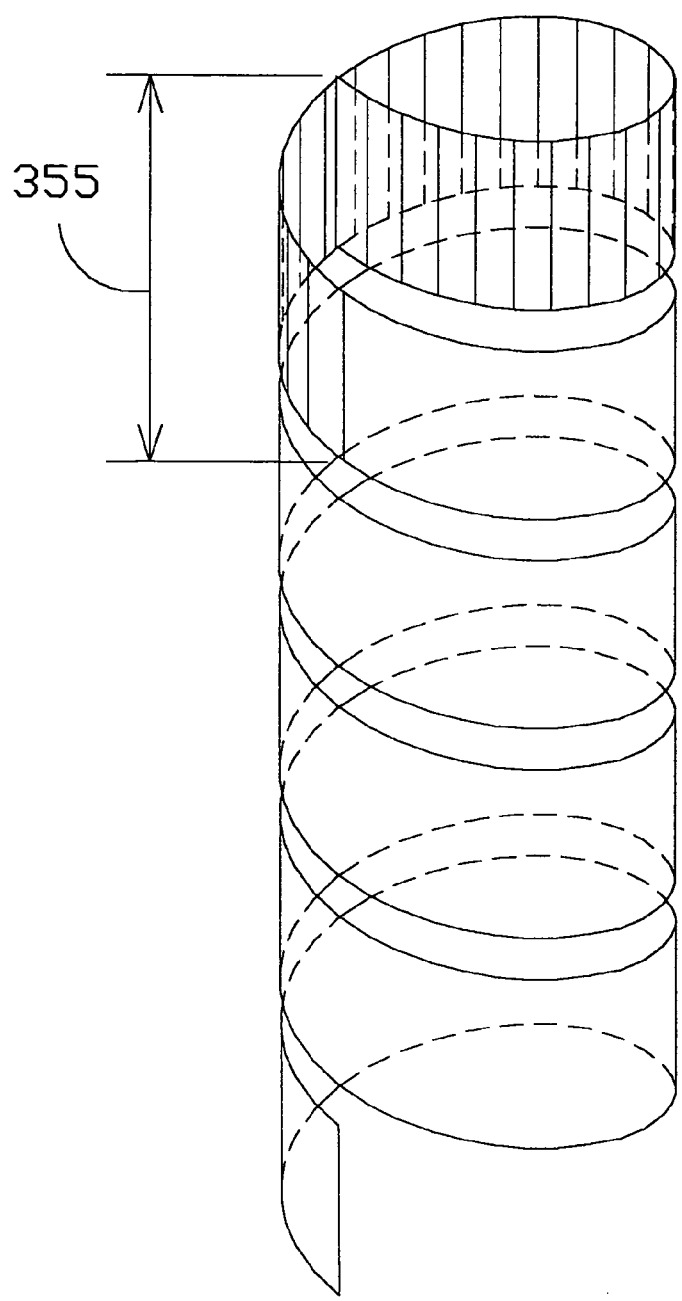
FIG. 17B is an illustration of a repeat unit for a helical hinge stent.
Figure 18:
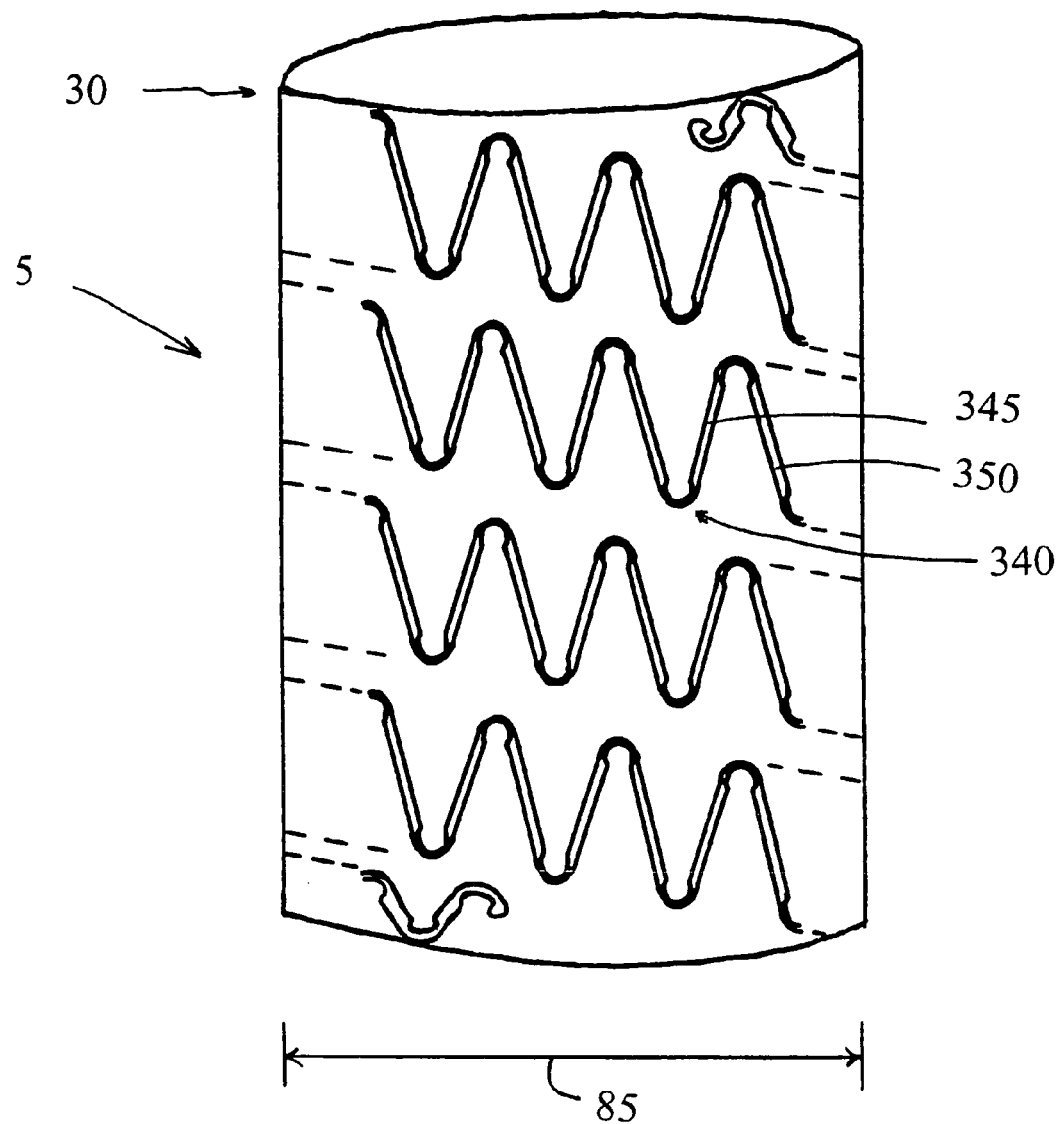
FIG. 18 is an isometric view of a hinge stent having in a deployed state.

In still another embodiment of the hinge stent 5 of the present invention, a series of nodes 340, upper struts 345, and lower struts 350 can be formed into a helical shape that extends throughout the entire length of the hinge stent 5 forming a continuous structure as shown in FIGS. 17A and 18. A frontal view of a portion of a helically shaped hinge stent 5 is shown in a nondeployed state and with a nondeployed diameter 75 in FIG. 17A and in a deployed state with a deployed diameter 85 in FIG. 18. FIG. 17B is an illustration of a repeat unit 355 formed from a helical stent similar to that shown in FIGS. 17A and 18. The stent section body 35 of this embodiment has two struts 345 & 350 per each node 340. A single continuous series of nodes 340, upper struts 345, and lower struts 350 extends in a helical configuration throughout the entire length of the hinge stent 5 forming a cylindrically shaped hinge stent 5. This embodiment of a hinge stent 5 forms a continuous configuration of nodes and struts that extend with a helical wind in a circumferential 70 and axial 60 direction as the helix forms a continuous spiral. The circumferential expansion of this embodiment of hinge stent is coupled in the axial direction 60 of a stent section since a single series of nodes and struts extends throughout the length of the stent section 20. Expansion forces directed in the circumferential direction are distributed and shared in the axial direction also. This distribution of forces in both the axial and circumferential direction serves to prevent abrupt change in the diameter of the stent section that could otherwise lead to localized high stress regions in the vessel being treated. The hinge stent 5 of this embodiment can either be a balloon-expandable hinge stent 5 or a self-expandable hinge stent 5. As a balloon-expandable hinge stent 5 it can be mounted onto the balloon of a balloon dilitation catheter in its nondeployed state and delivered percutaneously to the site of the lesion. Each repeat unit 355 is connected to the adjacent repeat unit with struts and hinges. As the helical structure winds continuously throughout the helical length of the stent section, this continuous structure provides a continuous uniform surface without abrupt changes in diameter. This embodiment of the hinge stent 5 as shown in FIGS. 17A and 18 is comprised of helical repeat units formed entirely of nodes and struts joined to each other contiguously to form a single stent section 20. In traversing around a curve in a tortuous vessel one helical repeat unit 355 can move away in an axial direction 60 from an adjacent helical repeat unit 355 along the outside portion of the curve in which the hinge stent is being placed. Once the hinge stent 5 has reached the site of the lesion the balloon can be expanded to expand the hinge stent 5 to the larger deployed diameter 85 shown in FIG. 18. In its expanded or deployed state the hinge stent 5 is also very flexible axially and can be easily implanted around a curved vessel as adjacent helical repeat units 355 of the hinge stent 5 are not connected or joined to each other. The upper struts 345 can be of equal length and shape to the lower struts 350 or the upper struts 345 can differ from the lower struts 350. If the upper struts 345 and lower struts 350 are of an equal length, then the struts 345 & 350 will not align parallel with the axial direction 60 in the nondeployed state.

Figure 19:
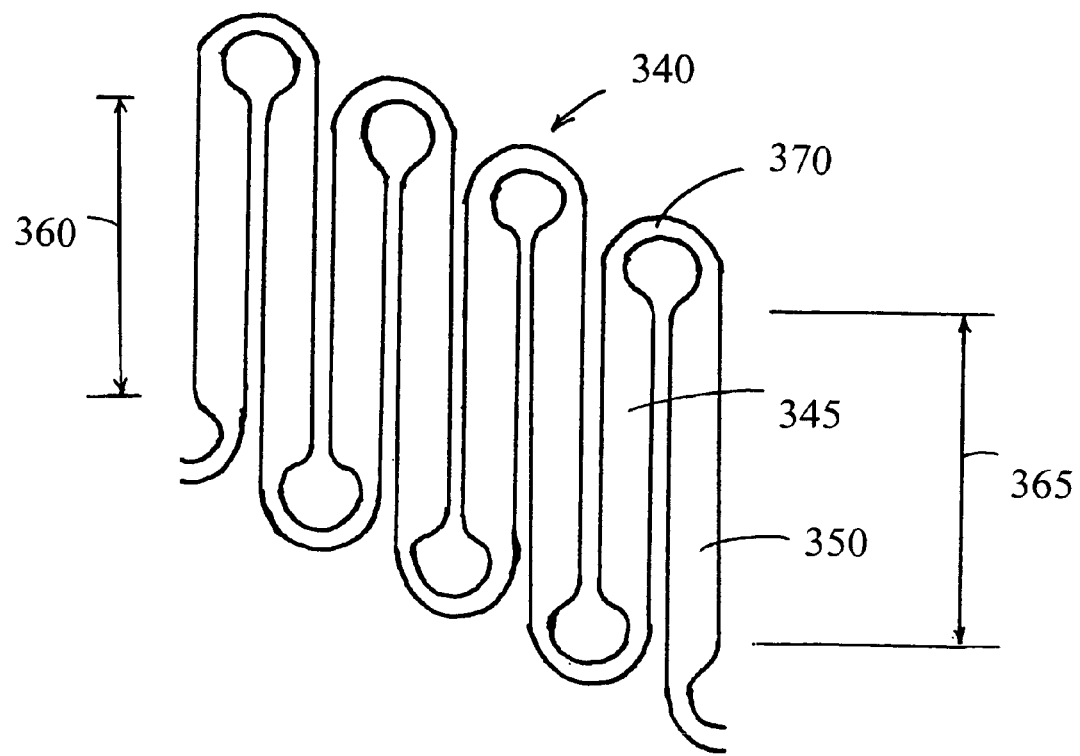
FIG. 19 is a portion of a helical repeat unit having one hinge per node in a nondeployed state.
Figure 20:
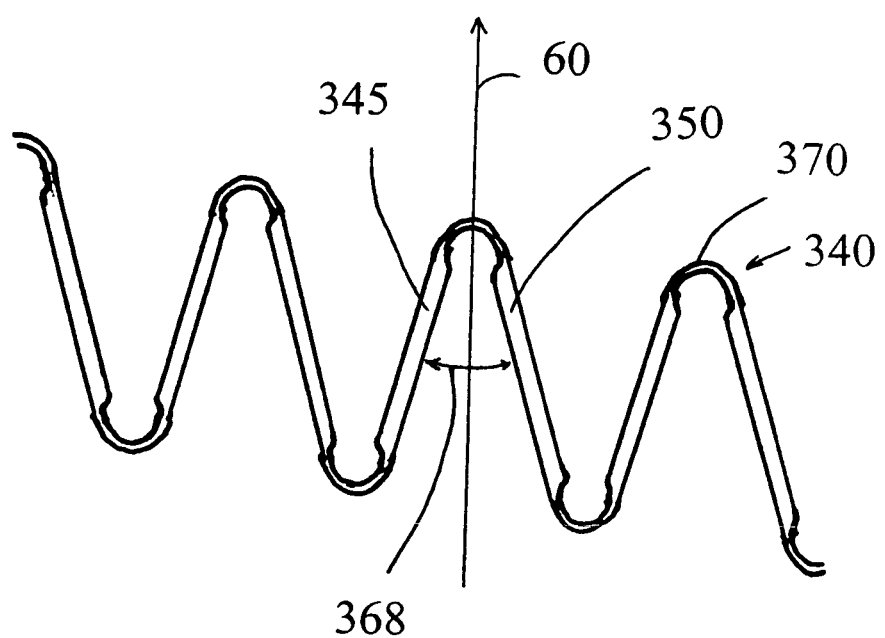
FIG. 20 is a portion of a helical repeat unit having one hinge per node in a deployed state.

FIGS. 19 and 20 show an enlarged view of a portion of a helical repeat unit 355 (see FIG. 17B) of the embodiment of the helical hinge stent 5 shown in FIGS. 17A and 18, respectively. The upper 345 and lower 350 struts are aligned parallel to each other and in the axial direction 60 in a nondeployed state shown in FIG. 19. The nodes 340, upper struts 345, and lower struts 350 are joined contiguously together in series as they form a helical repeat unit 355 of the hinge stent 5. In this embodiment the upper 345 and lower 350 struts are of two different sizes or lengths, the upper strut 345 having an upper strut length 360 that is shorter than the lower strut length 365 of the lower strut 350. Each strut is aligned parallel to each other and in the axial direction 60 in a nondeployed state providing the closest packing configuration for the struts. In a deployed state as shown in FIG. 20 the upper 345 and lower 350 struts of this embodiment form a deployment angle 368 that is symmetrical with respect to the axial direction 60. Positioning the upper 345 and lower 350 struts parallel to each other in a nondeployed state provides this embodiment with the greatest expansion ratio of deployed diameter to nondeployed diameter. Ease of machining a balloon-expandable hinge stent 5 in a nondeployed state with the struts parallel to the axis provides an additional advantage for forming the hinge stent 5 as shown in FIG. 19 although it is understood that the struts are not required to be parallel in the nondeployed state. For a self-expandable hinge stent 5 the machining can occur in an expanded or deployed state as shown in FIG. 19. Following machining the self-expandable hinge stent 5 can be folded to form the smaller nondeployed state and held in a sheath at its smaller nondeployed diameter 75 for percutaneous insertion into the blood vessel. The node of this embodiment as shown in FIGS. 19 and 20 can consist of a single hinge that is joined to each of two struts. Hinge and strut dimensions will affect the stent function in a manner consistent with the discussion made earlier for the embodiments or FIGS. 1A-6 and FIGS. 7-10.

Figure 21:
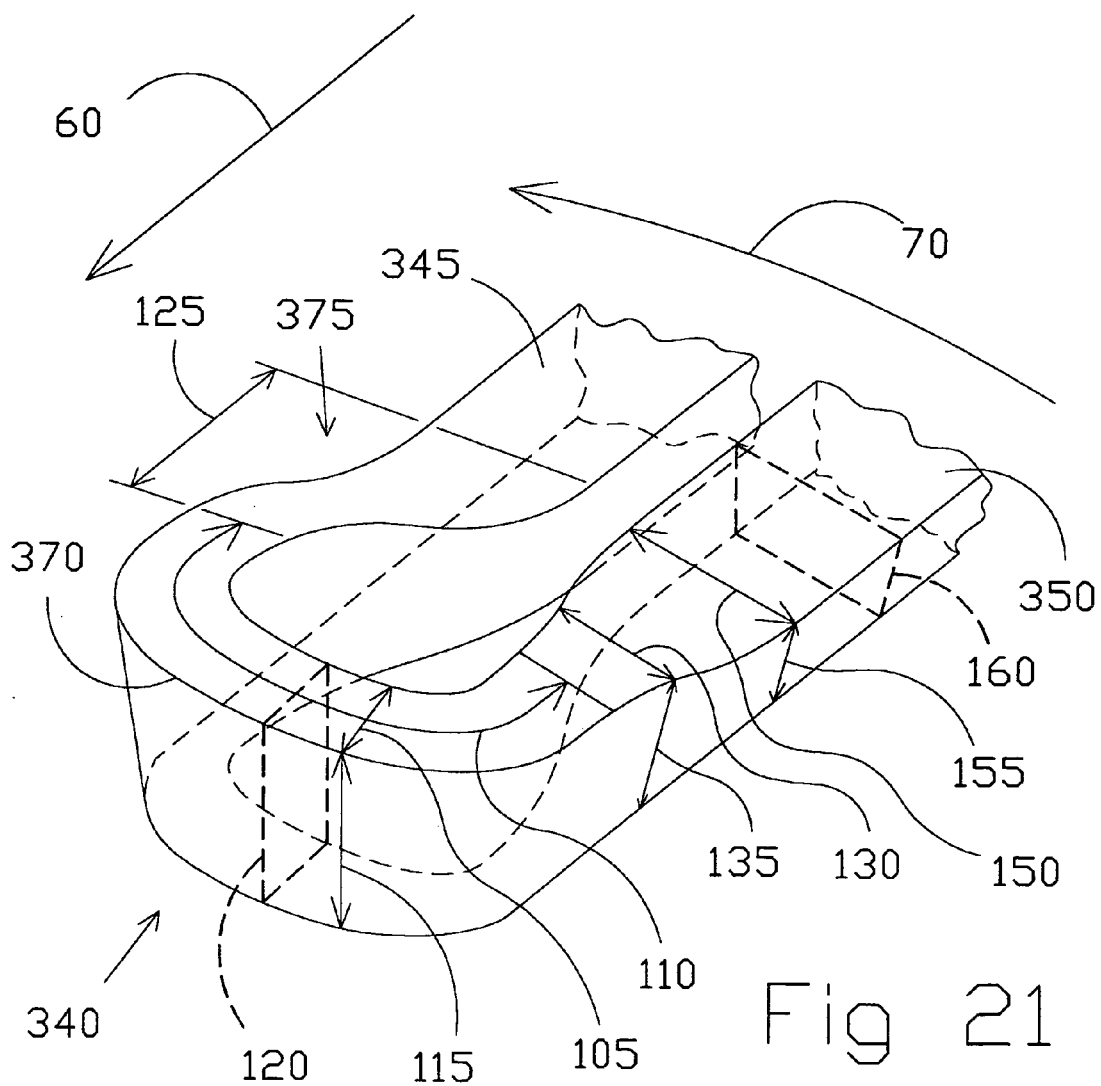
FIG. 21 is an enlarged detail view of a node having one hinge.

FIG. 21 shows an enlarged isometric view of a portion of the helical hinge stent 5 of the embodiment of FIG. 19 in a nondeployed state. The node 340 of this embodiment includes a hinge 370 joined contiguously to two transition regions 375. Each transition region 375 is contiguously joined to an upper 345 or lower 350 strut. The hinge has a hinge width 105, a hinge length 110, and a hinge radial dimension 115. The transition region 375 has a transition region width 130, a transition region length 125, and a transition region radial dimension 135. The upper strut 345 and lower strut 350 each have a strut width 150, a strut length 145, and a strut radial dimension 155. The description of the hinges, the struts, the transition regions 375 of this embodiment along with their dimensions and functions is similar to the descriptions that have been presented for the preceding embodiments of the hinge stent 5. All reference numerals correspond to those elements previously or otherwise described.

An abbreviated discussion of the present embodiment will follow, referring collectively to FIGS. 17A-21. The hinge stent 5 of this embodiment can be a balloon-expandable hinge stent 5 or a self-expandable hinge stent 5. The hinge width 105 is significantly smaller than the strut width 150 for either the upper strut 345 or lower strut 350 to allow the hinge to deform the hinge width radius of curvature 380 in going from a nondeployed state to a deployed state. The hinge radial dimension 115 can be lengthened to increase the amount of expansion holding force for a balloon-expandable hinge stent 5 or expansion elastic force for a self-expandable hinge stent 5 is provided by the hinge stent 5 to hold the blood vessel open in a deployed state. The strut radial dimension 155 is significantly smaller than the hinge radial dimension 115 to allow the strut to deform elastically as the hinge stent 5 is exposed to a crush deformation that causes the hinge stent 5 to form an oval shape. The strut width 150 is significantly greater than the hinge width 105 such that the moment provided by the hinge to hold the blood vessel outward is transferred via the strut to the vessel wall without bending in the direction of the strut width 150. A longer strut length 145 will allow the hinge stent 5 to bend easier when exposed to a crush applied force that tends to form the hinge stent 5 into an oval shape. A longer hinge will increase the percentage of the perimeter of the hinge stent 5 that is associated with the struts in comparison to the nodes. Since the upper struts 345 and lower struts 350 are formed with a thin radial dimension that will deform elastically in the radial direction and the nodes are formed with a larger radial dimension that does not provide for significant deformation in the radial direction, a longer strut length 145 will allow the hinge stent 5 to deform more easily in crush deformation.

For a balloon-expandable hinge stent 5 of this embodiment the hinge length 110 can be preferably short to focus the deformation of the hinge into a smaller volume of hinge and require that the hinge undergo a greater amount of plastic deformation. Focusing of the plastic deformation will provide a greater percentage of plastic deformation in comparison to elastic deformation and provide less rebound following balloon expansion of the balloon-expandable hinge stent 5. The balloon-expandable hinge stent 5 of this embodiment provides an advantage of balloon expandability for accuracy of placement within the vasculature but non crushability such that the hinge stent 5 deforms elastically in the crush deformation mode. The upper 345 and lower 350 struts will deform elastically in a crush deformation and will return to their original conformation found in the deployed state. The use of hinges 370 to provide a moment to the upper 345 and lower 350 struts allows the hinge stent 5 to provide an expansion holding force that is as large or as small as desired and provide a crush strength that is as large or as small as desired. The expansion holding force is controlled independently from the crush elastic force. The expansion holding force is established by the hinge dimensions and the crush elastic force is established by the strut dimensions. For example, a large hinge width 105 and a large hinge radial dimension 115 along with a hinge length 110 that ensures primarily plastic deformation will provide a large expansion holding force for the hinge stent 5. A thin strut radial dimension 155 and a long strut length 145 along with the smallest strut width 150 that will still transfer the outward expansion force of the hinge to the vessel wall will provide the hinge stent 5 with the most flexible structure in a crush deformation.

For a self-expandable hinge stent 5 the hinge can have a longer hinge length 110 in order to better allow for an elastic deformation of the hinge without plastic deformation by reducing the amount of localized deformation of the hinge for a specific deployment angle 368 & 170. A longer hinge length 110 also provides the self-expandable hinge stent 5 with a reduced drop off of expansion elastic force in going from a nondeployed state to a deployed state. This allows the hinge stent 5 of this embodiment to provide a more uniform outward force regardless of small variations in the diameter of the vessel in which it is deployed. The expansion elastic force provided by the self-expandable hinge stent 5 of this embodiment is controlled independently from the crush elastic force.

The expansion elastic force is determined by the hinge dimensions and the crush elastic force is controlled by the strut dimensions. Thus the self-expandable hinge stent 5 of this embodiment can have a large or a small expansion elastic force to hold the vessel outward, and it can have a large or a small crush elastic force to resist forming an oval shape when exposed to a crush deformation. For example, to provide a large expansion elastic force the hinge width 105 is enlarged to its greatest extent without allowing for plastic deformation. The hinge length 110 is adjusted in conjunction with the hinge width 105 to ensure that only elastic deformation will occur. A shorter hinge length 110 will provide a greater expansion elastic force for the same deployment angle 368 & 170. A longer hinge length 110 will provide less drop off of expansion elastic force from a nondeployed state to a deployed state. For a longer hinge length 110 the hinge width 105 can be increased to provide a large expansion elastic force without allowing plastic deformation. A longer hinge radial dimension 115 will further increase the magnitude of the expansion elastic force provided by the hinge. The strut dimensions can be adjusted as described for the balloon-expandable hinge stent 5 to provide for flexibility in crush deformation. This discussion for adjusting the expansion elastic force for the self-expandable hinge stent 5, the expansion holding force for the balloon-expandable hinge stent 5, and the crush elastic force for either the self-expandable hinge stent 5 or the balloon-expandable hinge stent 5 applies equally well to the embodiments shown in FIGS. 1A-6, FIGS. 7-10, as well as the embodiments shown in FIGS. 17A-24.

The metal used in the formation of the embodiments shown in FIGS. 17A-24 can be the same as described earlier for other embodiments. The choice of elastic modulus and yield point for the metal will also influence the choice of hinge length 110 and hinge width 105 in order to obtain a deformation that provides elastic deformation for the self-expandable hinge stent 5 or plastic deformation for the balloon-expandable hinge stent 5. The choice of elastic modulus will also directly influence the hinge radial dimension 115 that used to provide the appropriate expansion elastic force for the self-expandable hinge stent 5 or the expansion holding force for the balloon-expandable hinge stent 5. It is preferred that a high elastic modulus material be chosen such that the radial thickness for the hinge stent is smallest and that the expansion forces and crush forces be determined by the dimensions of the hinges and struts.

Figure 22:
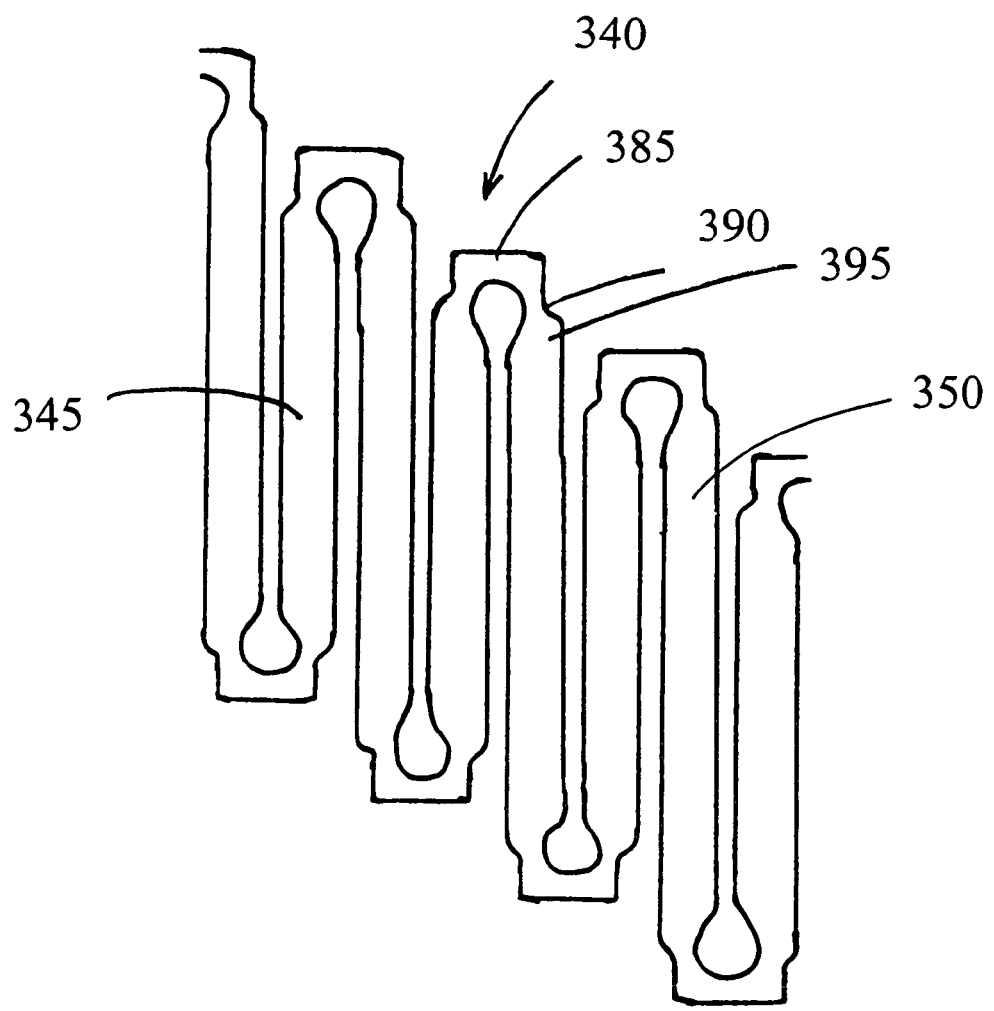
FIG. 22 is a portion of a helical repeat unit having two hinges per node in a nondeployed state.
Figure 23:
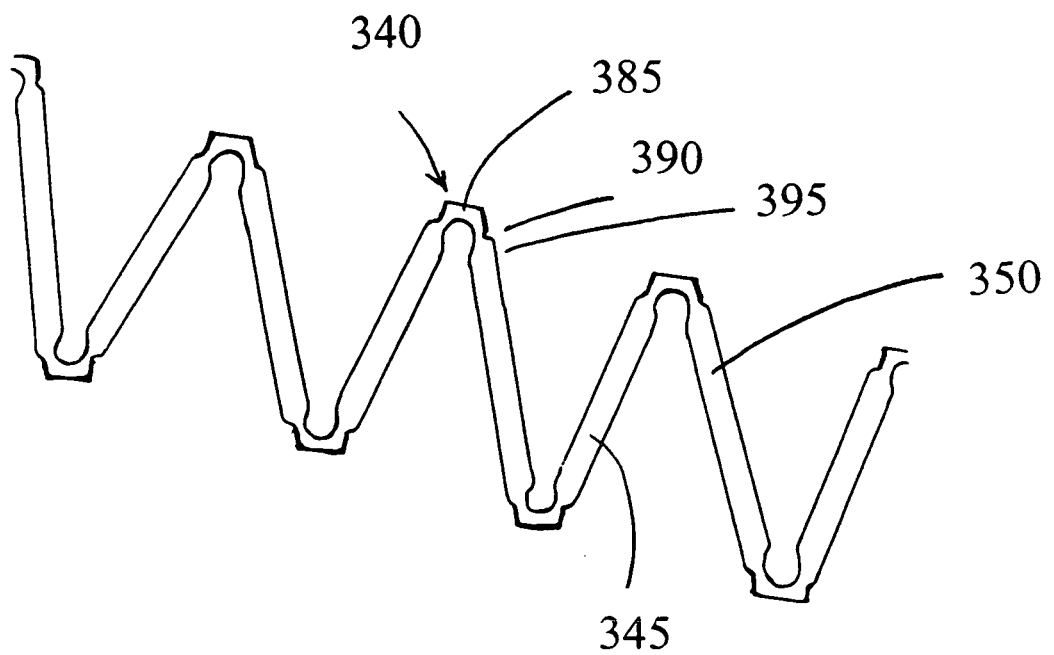
FIG. 23 is a portion of a helical repeat unit having two hinges per node in a deployed state.
Figure 24:
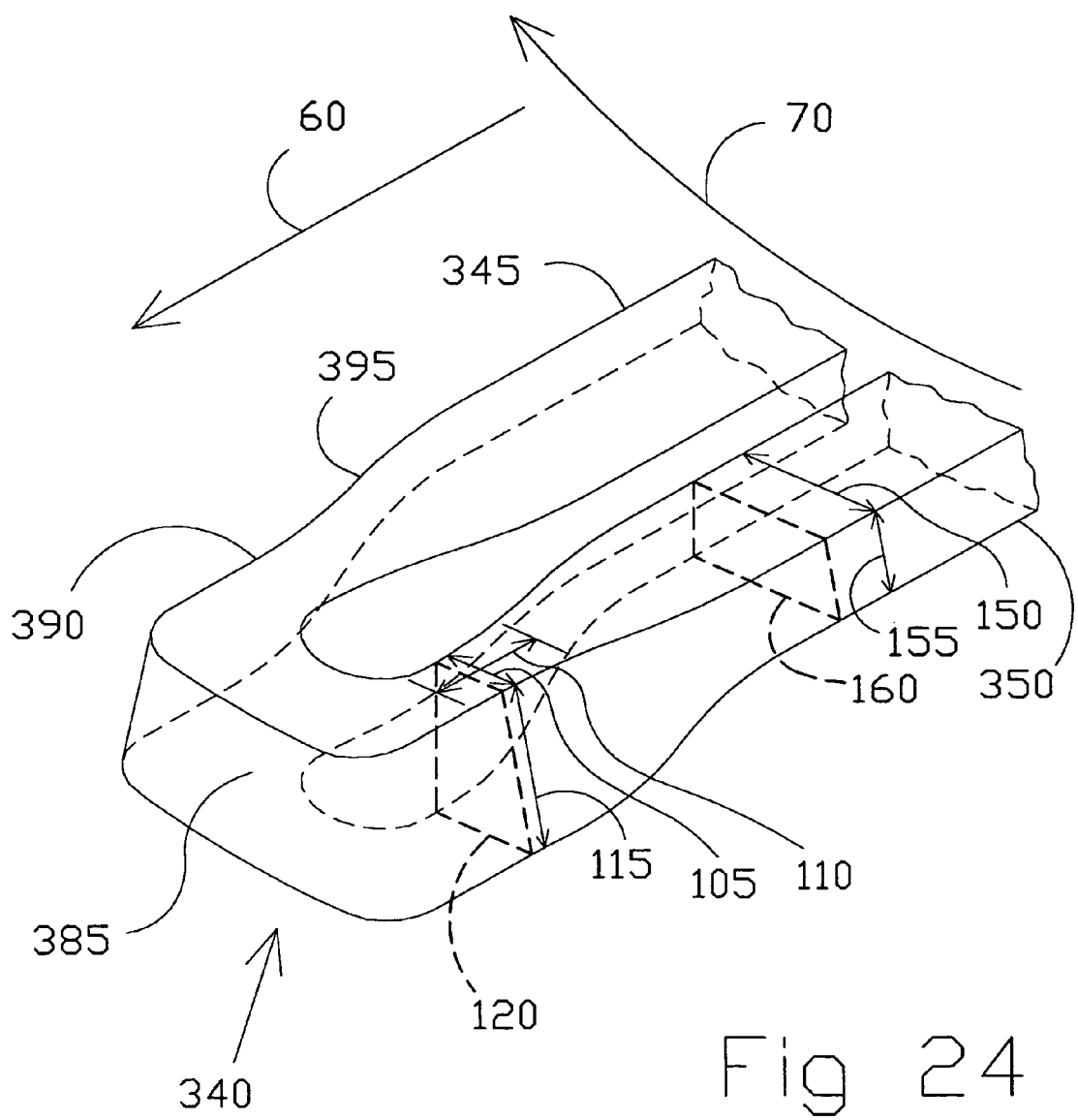
FIG. 24 is an enlarged detail view of a node having two hinges.

An alternate embodiment for the node structure for the helical hinge stent 5 shown in FIGS. 17A and 18 is shown in FIGS. 22-24. FIG. 22 shows a portion of a repeat unit having a node 340, upper 345, and lower 350 strut structure in a nondeployed state of an embodiment of the helical hinge stent 5 of FIG. 17A. FIG. 23 shows a portion of a repeat unit having a node 340 and upper 345 and lower 350 strut structure in a deployed state for an embodiment of FIG. 18. FIG. 24 shows a close-up isometric view of a node 340 and a portion of the upper 345 and lower 350 struts joined to the node. Referring collectively to FIGS. 22-24 this embodiment will be briefly described. This embodiment is very similar to the embodiment described in FIGS. 19-21. The main difference found in this embodiment is that the node 340 contains a hub 385, two hinges 390, and two transition regions 395 rather than a hinge 370 and two transition regions 375 as shown in FIGS. 19-21. The upper 345 and lower 350 struts are the same as those shown in the embodiment of FIGS. 19-21. The hub 385, as described in earlier embodiments does not undergo significant deformation during the expansion of the hinge stent 5 from a nondeployed state to a deployed state or during exposure to crush deformation. Each hinge 390 as shown in this embodiment in FIGS. 22-24 is similar to the hinge 370 shown in FIGS. 19-21 except that the hinge length 110 for each of the two hinges 390 has a shorter hinge length 110 than the embodiment shown in FIGS. 19-21. The presence of two smaller hinges 390 can help to focus the deformation of the hinge for a balloon-expandable hinge stent 5 and can provide a greater expansion elastic force for a self-expandable hinge stent 5. This embodiment with two hinges 390 can also provide advantages from an ease of machining standpoint. The presence of a hub can provide a suitable site for attaching an interconnecting means or a barb attachment means as will be discussed later. The function of the hinges 390, upper 345 and lower 350 struts and transition regions 395 are similar to what has been described previously for the embodiments of the hinge stent 5 shown in FIGS. 17A-21. All reference numerals correspond to those elements previously or otherwise described.

Figure 25:
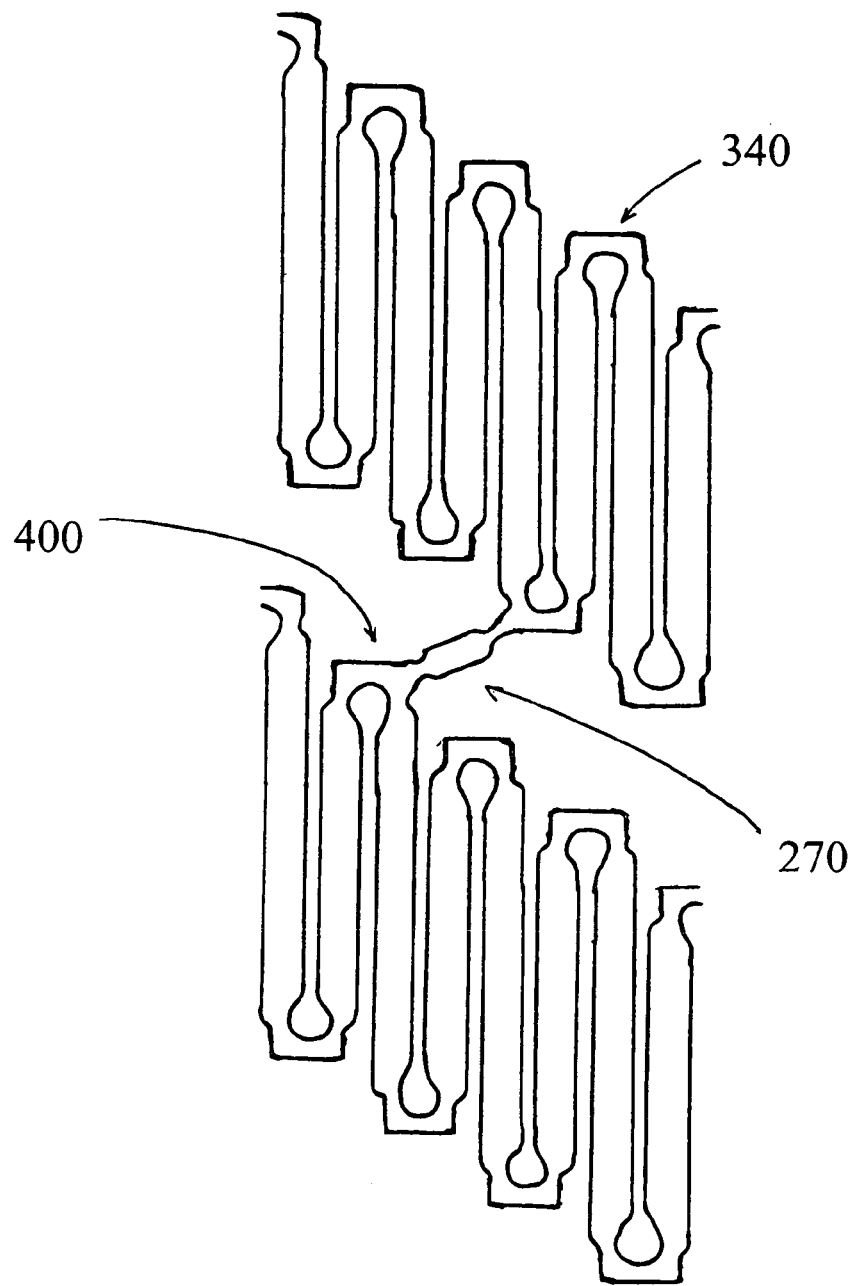
FIG. 25 is a portion of two helical repeat units joined by a hinged interconnector.
Figure 26:
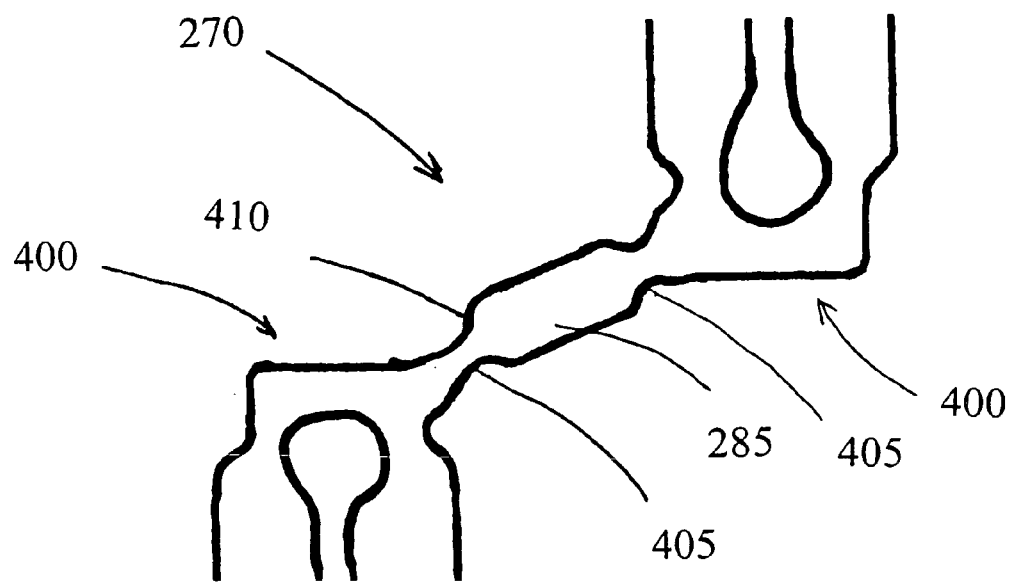
FIG. 26 is an enlarged detail view of a hinged interconnector joining two helical repeat units.
Figure 27:
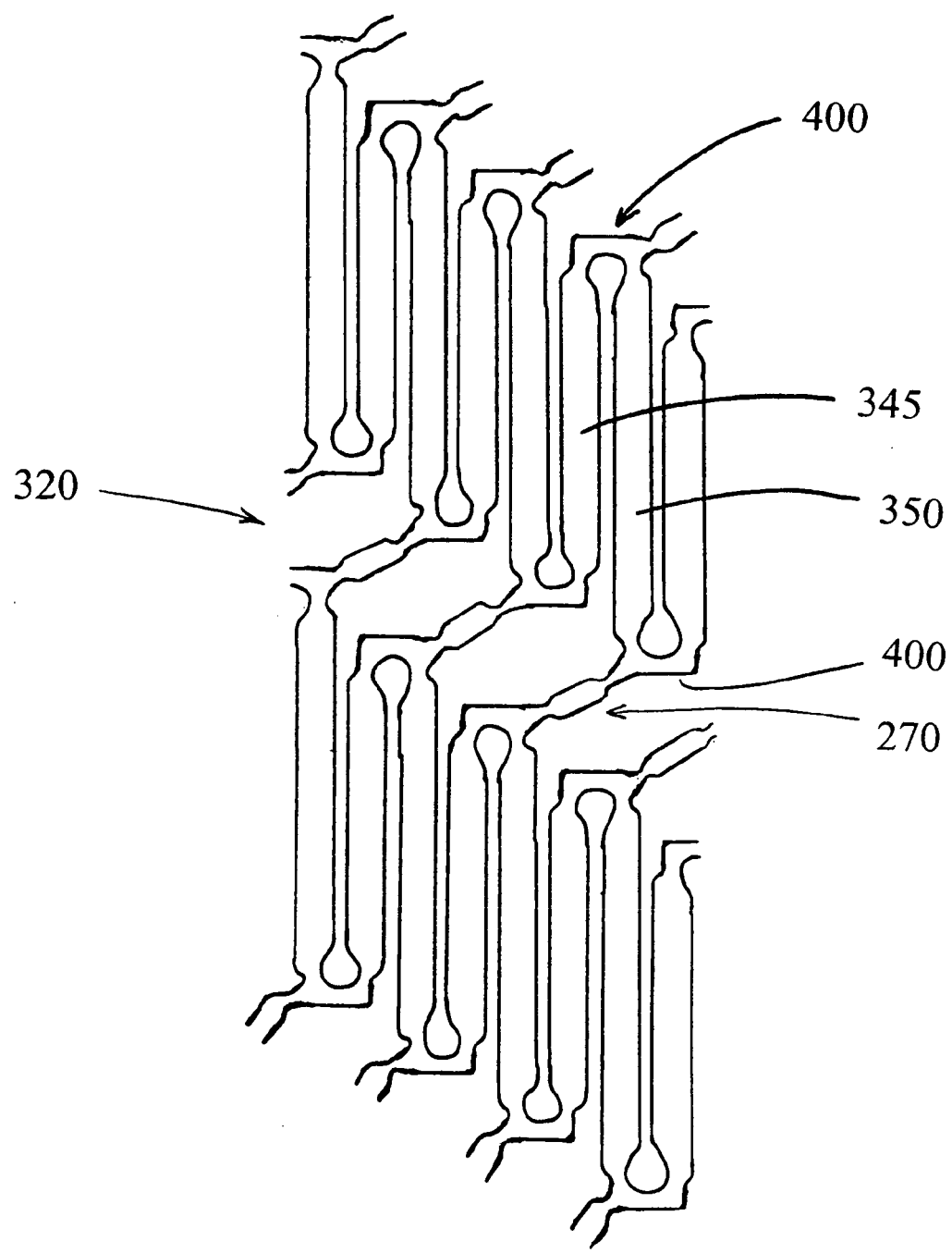
FIG. 27 is a portion of two helical repeat units joined by several hinged interconnectors.

FIGS. 25 and 26 show yet another embodiment of the hinge stent 5 of the present invention. This embodiment is similar to the embodiments shown in FIGS. 17A-24. To ensure that the adjacent helical repeat units 355 of the node and strut structure maintain a relative approximation with each other in an axial direction during the insertion of the hinge stent 5 and after implantation of the hinge stent 5 a hinged interconnector 270 or connecting element 328 (not shown) can be used to axially join to two separate nodes of adjacent helical repeat units 355. Preferably the hinged interconnector 270 comprised of nodes and struts is used to join nodes from adjacent helical repeat units 355 that are axially displaced as shown in FIG. 25. The resultant stent has advantageous properties discussed earlier for the hinge stent including uncoupling of expansion force from crush force and having an elastic crush deformation associated with strut bending in a radial direction that provides this hinge stent with being noncrushable. This embodiment for the helical hinge stent 5 has properties which are similar to those described for other embodiments of the present invention formed from nodes and struts. The embodiment shown in FIGS. 25 and 26 can have approximately one interconnector 270 to join each helical repeat unit 355 of the hinge stent 5. In this embodiment the hinged interconnector 270 has one connecting strut 285 joined by two connecting transition regions 410 and two connecting hinges 405 to connecting nodes 400 from two adjacent helical repeat units 355. Details of the function of this hinged interconnector 270 comprised of nodes and struts have been described previously in FIG. 13. The two connecting hinges 405 have a thin hinge width 105 that allows for ease of flexing in the direction of the hinge width 105 as the hinge stent 5 is placed into a tortuous or curved blood vessel. The connecting strut 285 has a thin radial dimension to allow ease of flexing in the direction of their radial dimension. The hinged interconnector 270 of this embodiment provides axial flexibility to the hinge stent 5 such that flexibility in traversing tortuous vessels will not be significantly affected by the hinged interconnector 270. The connecting hinges 405 will bend to provide this hinge stent 5 with flexibility in tortuous vessels. Multiple interconnectors 270 can be placed between connecting nodes 400 of adjacent helical repeat units 355 (FIG. 17B) of the hinge stent 5. Each node 340 of each helical repeat unit 355 of the helical hinge stent 5 can be formed into a connecting node 400 and joined to an adjacent connecting node 400 on an adjacent helical repeat unit 355 to form a stent section with three struts per node portion 320 as shown in FIG. 27. This embodiment has a closed configuration. This closed configuration provides additional axial and circumferential stability to the helical hinge stent beyond that found in FIGS. 17A and 18. the closed configuration is comprised of the nodes and struts of the hinged interconnector 270, the connecting nodes 400, the upper struts 345, and the lower struts 350. All reference numerals correspond to those elements previously or otherwise described. It is understood that the straight 330 or curved 335 leg elements as shown in FIGS. 15 and 16 can be used to join adjacent connecting nodes 400 from adjacent helical repeat units 355 of the hinge stent 5 to form an alternate embodiment.

The nodes and struts of the embodiments of the present invention provide for an expansion deformation of the hinge stent from a nondeployed diameter to a deployed diameter. The hinges undergo an elastic or a plastic expansion deformation in the uniformly curved surface of the stent. The expansion deformation forces generated by the hinges are independent of the crush deform forces generated by the struts as they bend in a radial direction due to a crush deformation. In traversing along curved or tortuous vessels the nodes and struts of a hinge stent can also provide the hinge stent with an ability to elongate in an axial direction on the outside of the curved vessel and compress in an axial direction along the inside of the curved vessel. The hinges allow for bending to occur in the uniformly curved hinge stent surface as the stent is required to elongate or compress axially in passing along a curved passage. Struts can provide axial alignment for the stent to ensure that the stent lies flat against the vessel wall without ridges that can cause stress risers between the stent and the vessel wall are avoided. Axial alignment of the stent with the vessel wall can provide enhanced healing of the vessel wall in contact with the stent. Hinged interconnectors with a similar node and strut structure as that described for the structure of each stent section can similarly provide the hinge stent of the present invention with an ability to elongate or compress axially when passing along a curved or tortuous vessel. The structure of the present invention includes hinges and struts extending in both a generally circumferential and generally axial direction from one repeat unit to another repeat unit throughout the entire structure of the stent section. One embodiment has hinged interconnectors that connect one stent section with another. Axial extension of the stent along the outside of a curved vessel or axial compression along the inside of a curved vessel is controlled by extension deformation of the hinge. An extension deformation force of the hinge generated by the extension deformation due to passage along a curved passage is determined by the hinge length, hinge width, and hinge radial dimension. These hinge dimensions affect the extension deformation force of the hinge in the same way that they affect the expansion deformation force of the hinge as described for the expansion deformation from the nondeployed state to the deployed state. The hinge does not bend in the radial direction during extensional deformation in passing along a curved passage due in part to the large hinge radial dimension. Struts can provide bending in the radial direction as the stent is bending along a curved passage. The strut width, strut length, and strut radial dimension allow the struts to bend elastically in the direction of the strut radial dimension with a strut elastic bending force that is independent of the extension deformation force of the hinge. Expansion forces exerted outward by the hinge stent against the vessel wall to hold it outwards and extensional forces exerted axially during bending of the hinge stent along a curved passage are shared throughout the node and strut structure that extends continuously throughout the hinge stent of this invention. These expansion and extension forces are controlled by the hinge dimensions. The hinge stent of the present invention can be formed of a metal with an elastic modulus that provides hinges with appropriate expansion deformation forces to hold the vessel open, provides struts with appropriate elastic crush deformation forces, and provides hinges with extensional forces to allow bending in a curved passage.

All of the embodiments of the hinge stent 5 can be used as a stent to help hold the blood vessel open at the site of a vessel lesion, stenosis, or other vessel injury. The hinge stent 5 of the present invention can also be used to hold an intravascular graft or other tubular member outwards against the vessel wall at or near the site of vessel injury. When used in this manner, the hinge stent 5 can be placed into the vessel and into at least a portion of the lumen of the intravascular graft. The hinge stent 5 can then be allowed to expand either by balloon expansion or by self expansion such that it holds the intravascular graft outwards against the vessel wall. Alternately, the hinge stent 5 of the present invention can be attached to the intravascular graft prior to implant and both the intravascular graft along with the hinge stent 5 are delivered to the site of the vessel injury together where they are deployed to a larger deployed diameter 85. One form of attaching the hinge stent 5 to the intravascular graft could involve sutures or other securing means that serve to tie the elements together. Another form of attaching the hinge stent 5 of the present invention to the intravascular tubular member could involve forming a physical encapsulation of the hinge stent 5 with the material of the intravascular graft. Here the material of the intravascular graft could surround some or all of the struts or some or all of the hinges of any of the embodiments of the hinge stent 5. For example, the hinge stent 5 could be physically contained within a portion of or all of an expanded polytetrafluoroethylene tubular member to form a stent graft for treatment of vessel injury. Attachment of the hinge stent 5 to the intravascular graft can also include physical or chemical bonding between the metal of the hinge stent 5 and the material of the intravascular graft.

Figure 28:
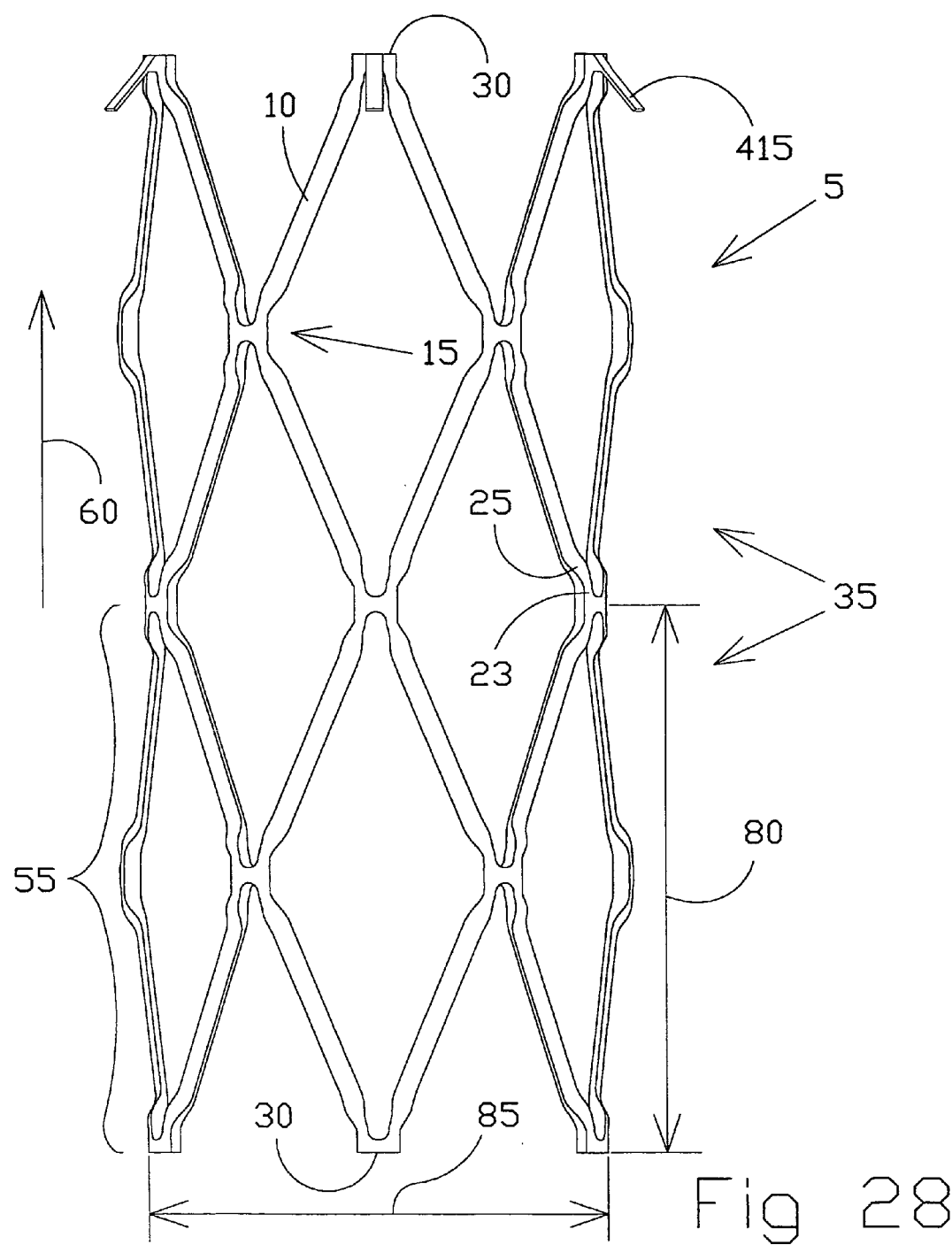
FIG. 28 is an isometric view of a hinge stent having a four strut per node body in a deployed state with barbs.
Figure 29:
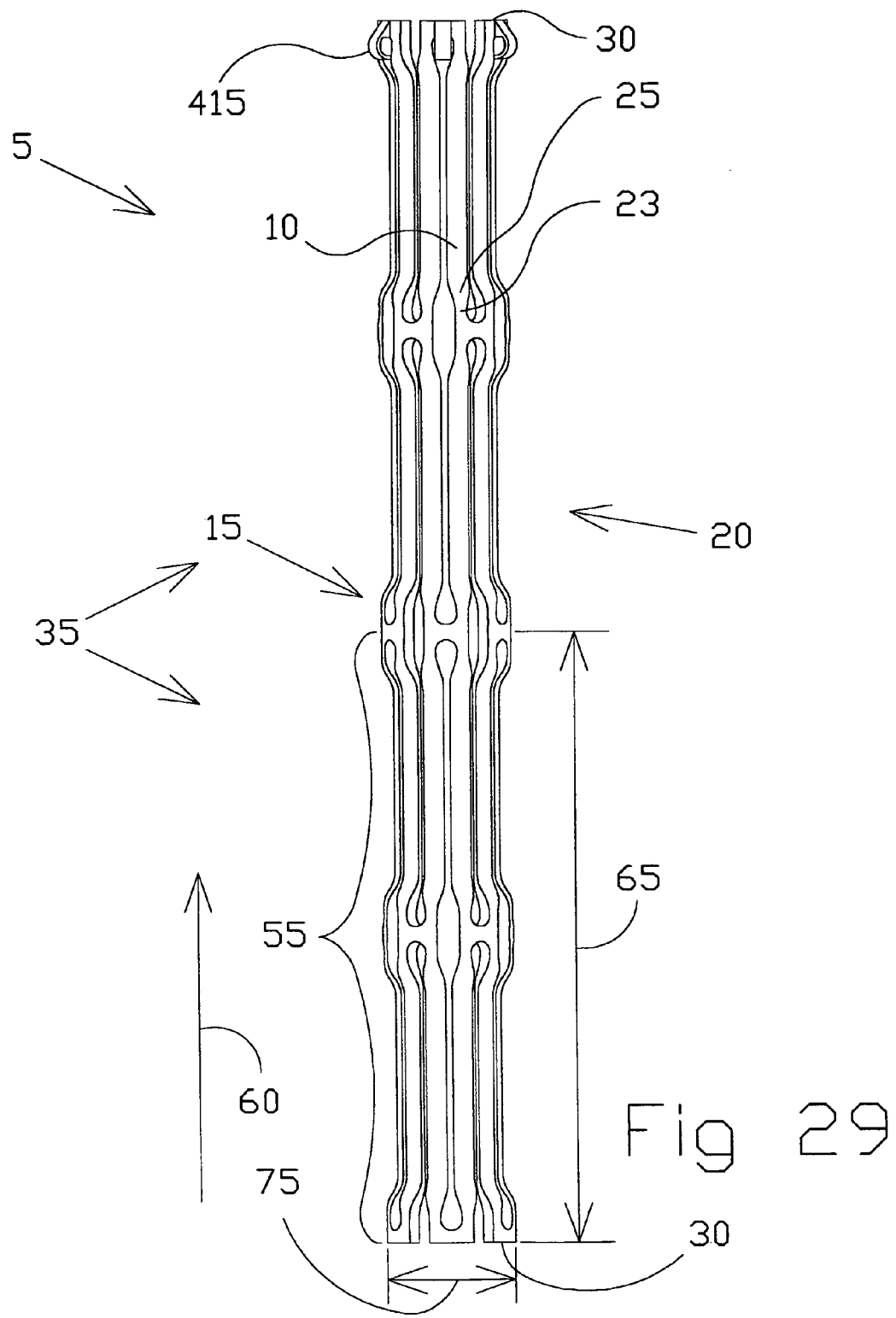
FIG. 29 is an isometric view of a hinge stent having a four strut per node body in a nondeployed state with barbs.

An embodiment of the hinge stent 5 of the present invention can be formed with a barb attachment means or barbs 415 as a component of one or more nodes 420 of the hinge stent 5 and extended as shown in FIG. 28 in a deployed state of the hinge stent 5 with a deployed diameter 85. Each barb is contiguously joined to the hinge or hub of a node. Each barb 415 can be machined contiguously with the node of the hinge stent using mechanical, laser, chemical, electrochemical, or other appropriate machining methods. This contiguous junction of the barb with the hinge stent reduces any tendency for fracture of the barb from the hinge stent to occur. The barbs 415 are shown joined to one stent end 30 of a hinge stent 5 similar to the embodiment shown in FIGS. 1A-6. The barbs 415 can just as well be placed on both ends of the hinge stent 5 or can be a component of any of the nodes 420 located throughout the stent section body 35. Barbs 415 can similarly be a component of the nodes of other embodiments of the hinge stent 5 of the present invention. For example, barbs 415 can be a component of any of the Y tail nodes of the hinge stent 5 shown in FIGS. 6-10. Similarly, barbs 415 can be a component of any of the nodes of the embodiments of the hinge stent 5 found in FIGS. 17A-24. The barbs 415 can serve to hold the hinge stent 5 in place within the blood vessel without significant possibility for stent migration. Additionally, the hinge stent 5 can be attached as described earlier to an intravascular graft to hold the intravascular graft outward against the vessel wall and ensure that the intravascular graft does not migrate. FIG. 29 shows the hinge stent 5 of the present invention with barbs 415 retracted and the hinge stent 5 in a nondeployed state with a nondeployed diameter 75. As the stent is expanded to a specific diameter, the struts separate and allow the barb 415 to deploy fully. Barb deployment is not gradual and is not proportional to the amount of strut deployment.

Figure 30:
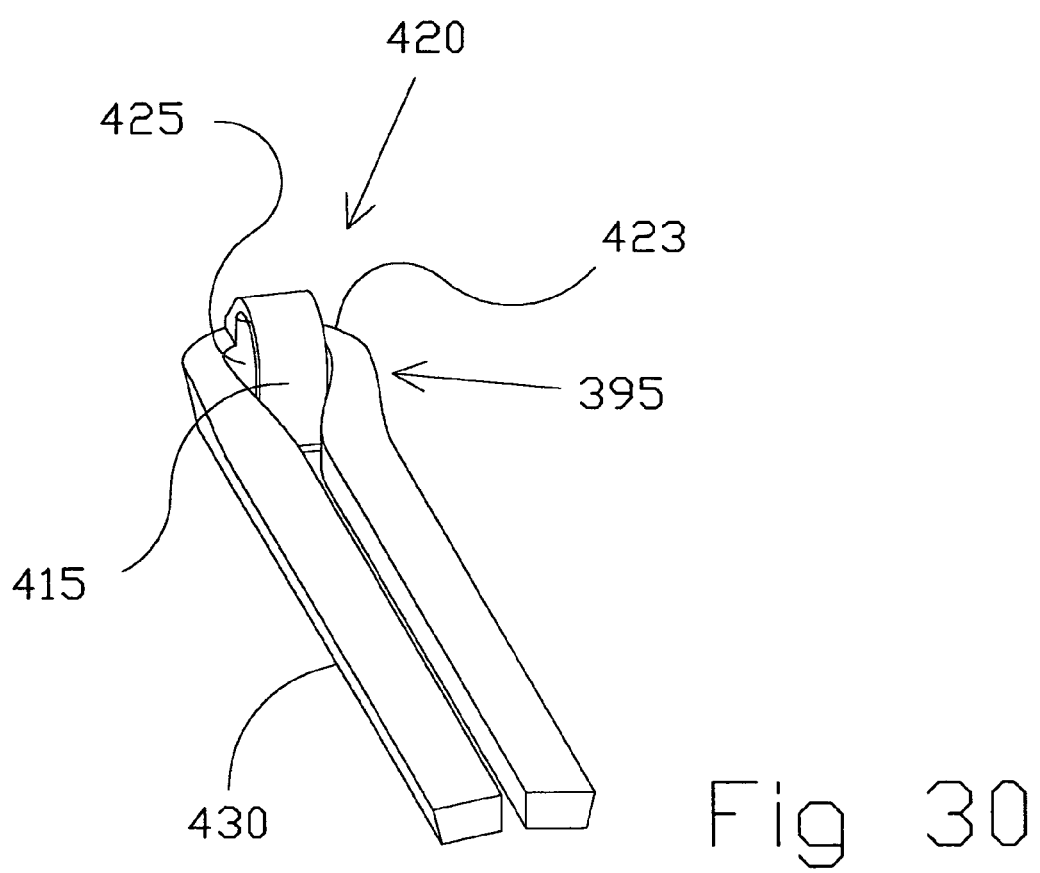
FIG. 30 is an enlarged detail view of a portion of a hinge stent in a nondeployed state with a barb.
Figure 31:
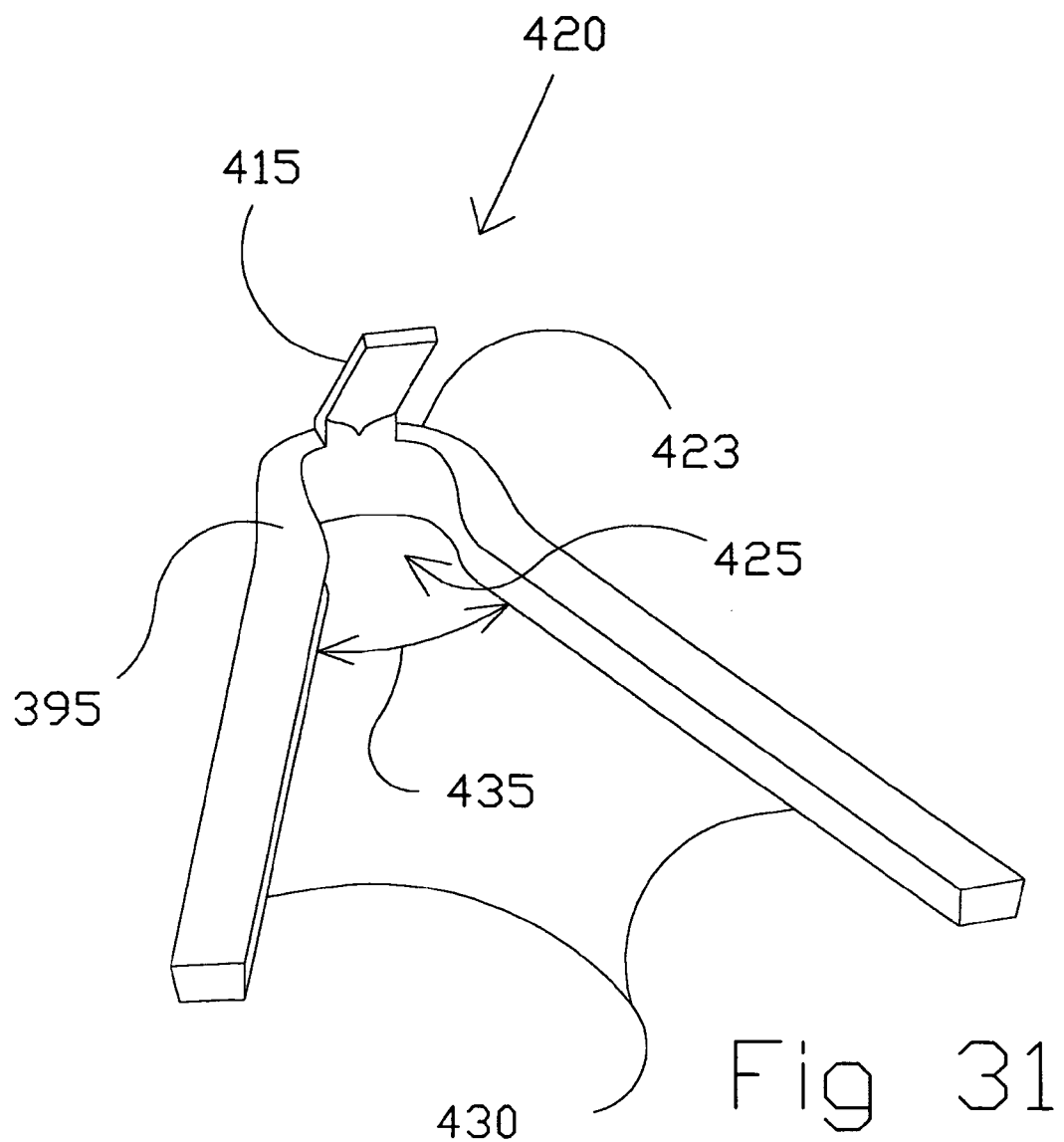
FIG. 31 is an enlarged detail view of a portion of a hinge stent in a deployed state with a barb.

FIGS. 30 and 31 show a close-up view of a portion of a hinge stent 5 with the barbs 415 retracted and extended, respectively. The node 420 shown in FIGS. 30 and 31 can be a node 15 from an embodiment of FIGS. 1A-6, the Y node 175 of an embodiment or FIGS. 7-10, or a node 340 from an embodiment of FIGS. 17A-24. The node 420 has a hinge 423 which can be the hinge from any of the previously mentioned embodiments. In a retracted state the barbs 415 are folded over and deformed elastically into an intranodal opening 425 and held by the struts 430 or transition regions 395. The struts 430 are intended to represent struts 10 found in the embodiments of FIGS. 1A-6, arm struts 205 and tail struts 220 of FIGS. 7-10, or upper and lower struts 345 and 350 found in FIGS. 17A-24. The barb 415 can be attached directly to the hinge 423 as shown in FIGS. 30 and 31 or can be attached to a hub 100 (see FIG. 4) as identified in prior embodiments and shown in FIGS. 28 and 29. Upon deployment of the hinge stent 5 the struts move apart to form a deployment angle 435 and allow the barbs 415 to elastically return to an extended position as shown in FIG. 31. The barb do not extend in proportion to the amount of deployment angle as with other barb attachment means of other prior art stents. The present hinge stent 5 has barbs 415 that extend fully once they have been released by the movement of the struts to a specific deployment angle.

REFERENCE NUMERALS IN THE DRAWINGS

5. Hinge Stent
10. Struts
15. Nodes
20. Stent Section
23. Hinge
25. Transition Region
30. Stent End
35. Stent Body
40. Interstrut Openings
45. Internodal Openings
50. Intranodal Openings
55. Repeat Units
60. Axial Direction
65. Nondeployed Repeat Unit Length
70. Circumferential Direction
75. Nondeployed Diameter
80. Deployed Repeat Unit Length
85. Deployed Diameter
90. Uniformly Curved Hinge Stent Surface
93. Oval Hinge Stent Surface
95. Radial Radius of Curvature
100. Hub
105. Hinge Width
110. Hinge Length
115. Hinge Radial Dimension
120. Hinge Cross Sectional Area
125. Transition Region Length
130. Transition Region Width
135. Transition Region Radial Dimension
140. Transition Region Cross Sectional Area
145. Strut Length
150. Strut Width
155. Strut Radial Dimension
160. Strut Cross Sectional Area
165. Hinge Width Radius of Curvature
170. Deployment Angle
175. Y Node
180. T Node
185. Y Hub
190. T Hub
195. Y Arm Transition Region
200. Y Arm Hinges
205. Arm Struts
210. Y Tail Transition Region
215. Y Tail Hinge
220. Tail Strut
225. T Arm Transition Regions
230. T Arm Hinges
235. T Axial Transition Region
240. T Axial Hinge
245. Axial Strut
247. Closed Loop
248. Closed Configuration
250. Hinge Stent Radius of Curvature
255. Stent Axis
260. Stent Mid-Length
265. Intermediate Diameter
270. Hinged Interconnector
275. Connecting Node
280. End Node
285. Connecting Struts
290. Flex Node
295. Flex Hinge
300. Flex Transition Regions
305. Connecting Hinge
310. Connecting Transition Region
315. Four Strut per Node Portions
320. Three Strut per Node Portions
325. Two Strut per Node Portions
328. Connecting Element
330. Straight Leg Element
335. Curved Leg Element
340. Nodes
345. Upper Struts
350. Lower Struts
355. Helical Repeat Unit
360. Upper Strut Length
365. Lower Strut Length
368 Deployment Angle
370. Hinge
375. Transition Regions
380. Hinge Width Radius of Curvature
385. Hub
390. Hinges
395. Transition Regions
400. Connecting Node
405. Connecting Hinge
410. Connecting Transition Region
415. Barbs
420. Node
425. Intranodal Space
423. Hinge
430. Struts
435. Deployment Angle

We claim:

1. A method of use for a tubular member having a nondeployed state and capable of undergoing an expansion deformation to a deployed state within a tubular vessel of the body that is exposed to an external force, said method comprised of, A. expanding said tubular member to the deployed state by deforming hinges of said tubular member plastically by an expansion device, B. exposing said tubular member to the external force wherein struts of said tubular member remain below their elastic limit and therefore flex elastically and not plastically in the radial direction during a crush deformation that places said tubular member into an oval shape, C. said hinges having a radial dimension that is greater than a radial dimension of said struts thereby not deforming said hinges during exposure of said tubular member to the external forces, D. said hinges having a hinge length, said hinge length extending along a path that undergoes bending during the expansion deformation, said hinge length being shorter than three times a hinge width, said hinge being bounded by two surfaces that lie in the radial direction, said hinge width being equal to the distance between said surfaces.

2. The method of claim 1 wherein upon removal of the external force said tubular member recovers from the oval shape and returns to its original tubular shape.

3. The method of claim 1 wherein said hinges have a hinge length that deforms during the expansion deformation, said hinge length being short in comparison to a strut length such that the expansion deformation is focused in order to provide a plastic deformation of said hinge.

4. The method of claim 1 wherein said hinges have a hinge length that deforms during the expansion deformation, said hinge length being short in comparison to three times a hinge width such that the expansion deformation is focused in order to provide a plastic deformation along said hinge length during expansion of said tubular member.

5. A method of use for a tubular member having a nondeployed state and capable of undergoing an expansion deformation to a deployed state within a tubular vessel of the body that is exposed to an external force, said method comprised of, A. expanding said tubular member having hinges and struts to the deployed state by deforming hinges of said tubular member plastically, said hinges having a smaller hinge width than a strut width, B. exposing said tubular member to the external forces such that said struts having a thinner radial dimension than a hinge radial dimension remain below their elastic limit and therefore flex elastically and not plastically in the radial direction during a crush deformation, C. said hinges having a hinge length, said hinge length extending along a path that deforms during the expansion deformation, said hinge length being shorter than three times a hinge width, said hinge being bounded by two surfaces that lie in the radial direction, said hinge width being equal to the distance between said surfaces.

6. The method of claim 5 wherein upon removal of the external force said tubular member elastically returns to its original tubular shape.

7. The method of claim 5 wherein said hinges have a hinge length that deforms during the expansion deformation, said hinge length being short in comparison to a strut length such that the expansion deformation is focused in order to provide a plastic deformation of said hinge.

8. The method of claim 5 wherein said hinges have a hinge length that deforms during the expansion deformation, said hinge length being short in comparison to three times a hinge width such that the expansion deformation is focused in order to provide a plastic deformation along said hinge length during expansion of said tubular member.

* * * * *